United States Patent
Ho et al.

(10) Patent No.: US 12,122,843 B2
(45) Date of Patent: Oct. 22, 2024

(54) HIGH AFFINITY MONOCLONAL ANTIBODIES TARGETING GLYPICAN-1 AND METHODS OF USE

(71) Applicant: The U.S.A., as represented by the Secretary, Department of Health and Human Services, Bethesda, MD (US)

(72) Inventors: Mitchell Ho, Urbana, MD (US); Nan Li, Laurel, MD (US); Jiajia Pan, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 758 days.

(21) Appl. No.: 17/422,609

(22) PCT Filed: Jan. 15, 2020

(86) PCT No.: PCT/US2020/013739
§ 371 (c)(1),
(2) Date: Jul. 13, 2021

(87) PCT Pub. No.: WO2020/154150
PCT Pub. Date: Jul. 30, 2020

(65) Prior Publication Data
US 2022/0098323 A1 Mar. 31, 2022

Related U.S. Application Data

(60) Provisional application No. 62/795,415, filed on Jan. 22, 2019.

(51) Int. Cl.
| | | |
|---|---|---|
| C07K 16/30 | (2006.01) | |
| A61K 39/00 | (2006.01) | |
| A61K 47/68 | (2017.01) | |
| A61K 47/69 | (2017.01) | |
| A61P 35/04 | (2006.01) | |
| C07K 14/47 | (2006.01) | |

(52) U.S. Cl.
CPC ........ *C07K 16/303* (2013.01); *A61K 47/6829* (2017.08); *A61K 47/6929* (2017.08); *A61P 35/04* (2018.01); *C07K 14/4725* (2013.01); *A61K 2039/505* (2013.01)

(58) Field of Classification Search
None
See application file for complete search history.

(56) References Cited

U.S. PATENT DOCUMENTS

| | | |
|---|---|---|
| 7,744,874 B2 | 6/2010 | Korytko et al. |
| 9,409,994 B2 | 8/2016 | Ho et al. |
| 10,077,316 B2 | 9/2018 | Naka et al. |
| 2018/0230230 A1 | 8/2018 | Yaguchi et al. |
| 2019/0046659 A1 | 2/2019 | Wang et al. |

FOREIGN PATENT DOCUMENTS

| | | | |
|---|---|---|---|
| CN | 101646457 A | 2/2010 | |
| CN | 104520331 A | 4/2015 | |
| CN | 106397593 A | 2/2017 | |
| EP | 3617231 | 3/2020 | |
| WO | WO 2015/098112 A1 | 7/2015 | |
| WO | WO 2016/061608 | 4/2016 | |
| WO | WO 2016/112423 | 7/2016 | |
| WO | WO 2016/168885 | 10/2016 | |
| WO | WO-2016196726 A1 * | 12/2016 | ......... A61K 39/3955 |
| WO | WO 2018/046879 | 3/2018 | |
| WO | WO 2018/175988 | 9/2018 | |
| WO | WO 2018/199318 | 11/2018 | |

OTHER PUBLICATIONS

Cho et al., "Universal Chimeric Antigen Receptors for Multiplexed and Logical Control of T Cell Responses," *Cell*, vol. 173:1426-1438, 2018.
Davies et al., "Distribution and Clinical Significance of Heparan Sulfate Proteoglycans in Ovarian Cancer," *Clin. Cancer Res.*, vol. 10:5178-5186, 2004.
Frampton et al., "Glypican-1 is Enriched in Circulating-Exosomes in Pancreatic Cancer and Correlates with Tumor Burden," *Oncotarget*, vol. 9:19006-19013, 2018.
International Search Report and Written Opinion, dated Apr. 24, 2020, for PCT/US2020/013739 (11 pages).
Kato et al., "Glypican-1 (GPC-1) Specific CAR-T Cells Eradicate Established Solid Tumor Without Adverse Effects and Synergize with Anti-PD1 Antibody Therapies," *J. Immunother. Cancer*, vol. 6:P249, p. 127, 2018.
Kayed et al., "Correlation of Glypican-1 Expression with TGF-β, BMP, and Activin Receptors in Pancreatic Ductal Adenocarcinoma," *Int. J. Oncol.*, vol. 29:1139-1148, 2006.
Kleeff et al., "The Cell-surface Heparan Sulfate Proteoglycan Glypican-1 Regulates Growth Factor Action in Pancreatic Carcinoma Cells and is Overexpressed in Human Pancreatic Cancer," *J. Clin. Invest.*, vol. 102:1662-1673, 1998.
Li et al., "The Clinical Significance of Circulating GPC1 Positive Exosomes and its Regulative miRNAs in Colon Cancer Patients," *Oncotarget*, vol. 8:101189-101202, 2017.

(Continued)

*Primary Examiner* — Daniel E Kolker
*Assistant Examiner* — Maureen Varina Driscoll
(74) *Attorney, Agent, or Firm* — Klarquist Sparkman, LLP

(57) ABSTRACT

Monoclonal antibodies that specifically bind glypican-1 (GPC1) are described. Chimeric antigen receptor (CAR) T cells, immunotoxins and other antibody conjugates based on the GPC1-specific antibodies are also described. The disclosed CAR T cells, immunotoxins, GPC1-specific antibodies and conjugates thereof can be used, for example, in the diagnosis or treatment of GPC1-positive pancreatic cancer and other cancers.

40 Claims, 29 Drawing Sheets

Specification includes a Sequence Listing.

(56) References Cited

OTHER PUBLICATIONS

Matsuda et al., "Glypican-1 is Overexpressed in Human Breast Cancer and Modulates the Mitogenic Effects of Multiple Heparin-binding Growth Factors in Breast Cancer Cells," *Cancer Res.*, vol. 61:5562-5569, 2001.

Melo et al., "Glypican1 Identifies Cancer Exosomes and Facilitates Early Detection of Cancer," *Nature*, vol. 523:177-182, 2015.

Su et al., "Glypican-1 is Frequently Overexpressed in Human Gliomas and Enhances FGF-2 Signaling in Glioma Cells," *Am. J. Pathol.*, vol. 168:2014-2026, 2006.

Zhao et al., "Universal CARs, Universal T Cells, and Universal Car T Cells," *J. Hematol. Oncol.*, vol. 11:1-9, 2018.

\* cited by examiner

FIG. 9A  2B9 (GPC1 overexpression in KLM1 cells)
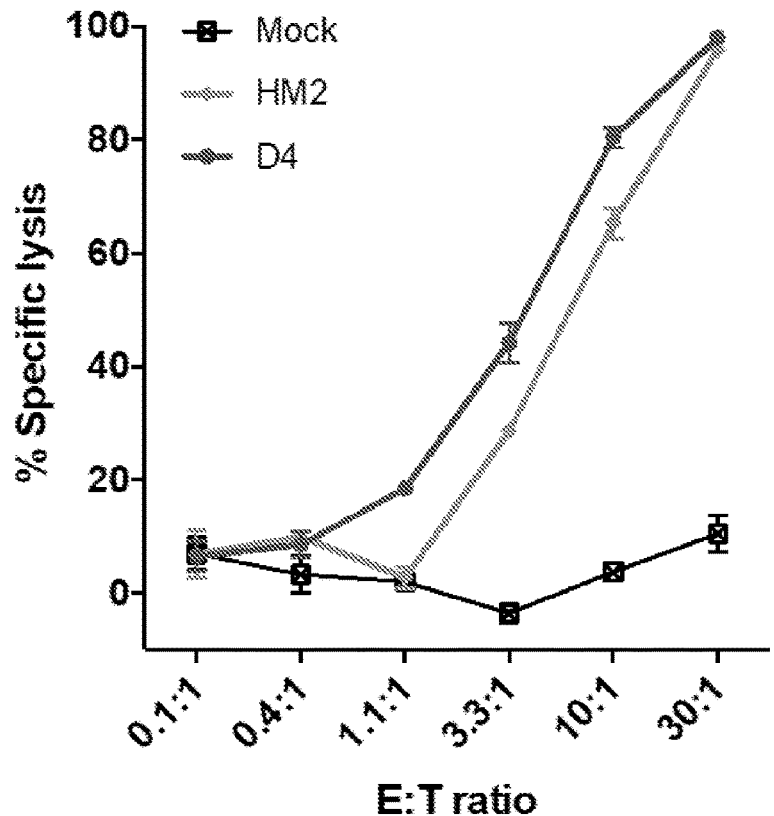
FIG. 9B  H8 (GPC1 overexpression in A431 cells)
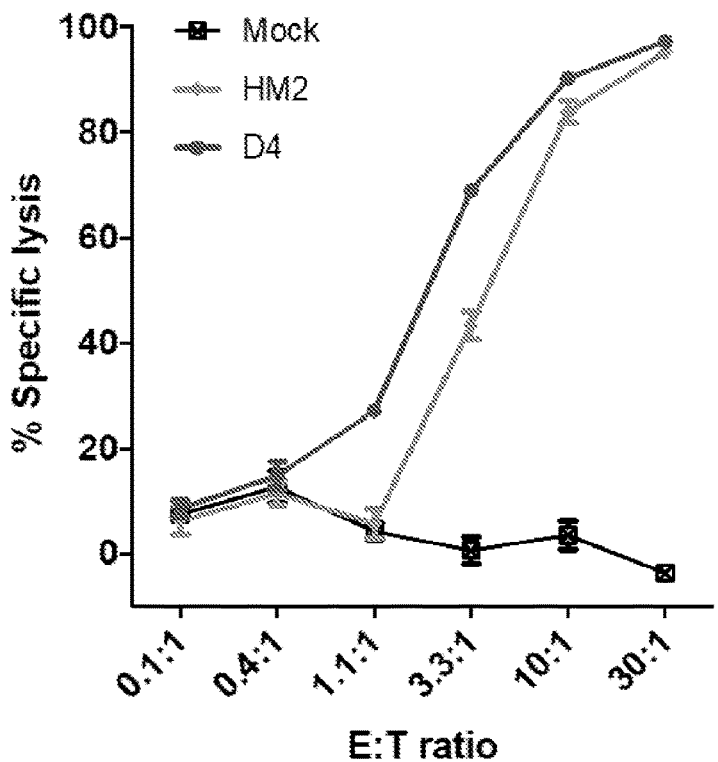

M marker
1. HM2-LR reducing
2. HM2-LR non-reducing
3. D4-LR reducing
4. D4-LR non-reducing

| Octet | KD (M) | Kon (1/Ms) | Kdis (1/s) |
|---|---|---|---|
| HM2-LR | 6.94E-09 | 2.97E+05 | 2.06E-03 |
| D4-LR | 6.25E-09 | 3.50E+05 | 2.18E-03 |

M marker
1. D4-AAA-D4-LR reducing
2. D4-AAA-D4-LR non-reducing
3. D4-GGS-D4-LR reducing
4. D4-GGS-D4-LR non-reducing Octet

ELISA

SEQUENCE LISTING

```
<160> NUMBER OF SEQ ID NOS: 21

<210> SEQ ID NO 1
<211> LENGTH: 342
<212> TYPE: DNA
<213> ORGANISM: Artificial Sequence
<220> FEATURE:
<223> OTHER INFORMATION: Synthetic polynucleotide

<400> SEQUENCE: 1
gaggttcagc tgcagcagtc tggggctgag cttgtgaggc caggggcctc agtcaagttg      60
tcctgcacag cttctggctt taacattaaa gacgactata tgcactgggt gaagcagagg     120
cctgaacagg gcctggagtg gattggatgg attgatcctg agaatggtga tactgaatat     180
gcctcgaagt tccagggcaa ggccactata acagcagaca catcctccaa cacagcctac     240
ctgcagctca gcagcctgac atctgaggac actgccgtct attactgtac tcgtagctcc     300
gtaggctact ggggccaagg caccactctc acagtctcct ca                        342

<210> SEQ ID NO 2
<211> LENGTH: 114
<212> TYPE: PRT
<213> ORGANISM: Artificial Sequence
<220> FEATURE:
<223> OTHER INFORMATION: Synthetic polypeptide (HM2 VH)

<400> SEQUENCE: 2

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Ser Ser Val Gly Tyr Trp Gly Gln Gly Thr Thr Leu Thr Val
```

Ser Ser

<210> SEQ ID NO 3
<211> LENGTH: 336
<212> TYPE: DNA
<213> ORGANISM: Artificial Sequence
<220> FEATURE:
<223> OTHER INFORMATION: Synthetic polynucleotide

<400> SEQUENCE: 3

```
gatgttgtga tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cttatttcac actcaagatc   240
agcagagtgg aggctgagga tctgggagtt tatttctgct ctcaaagaac acatgttccg   300
tacacgttcg gagggggac caagctggag ataaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Synthetic polypeptide (HM2 VL)

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Arg
                85                  90                  95

Thr His Val Pro Tyr Thr Phe Gly Gly Gly Thr Lys Leu Glu Ile Lys
            100                 105                 110

<210> SEQ ID NO 5
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 5

```
caggtgcagc tggtggagtc tgggggaggc ttggtgcagc cggggggtc tctgagactc     60
tcctgtgtag cctctggata cagctacagt attggttaca tggcctggtt ccgccaggcc   120
ccaggaaagg agcgcgcgtg gtcgcgtct cgatatactg gtgacggtgg cgcagtcttt    180
gacgacgccg tgaagggccg attcaccacc tccaagaga gtgccgggaa cacgttcgat    240
ttgcaaatgg acagcctgaa acctgaggac actgccatgt actattgcgc agcgaaaggg   300
cccggtttcg gcggtgggga gtactgggc cggggaccc aggtcaccgt ctcctca       357
```

<210> SEQ ID NO 6
<211> LENGTH: 119
<212> TYPE: PRT
<213> ORGANISM: Artificial Sequence
<220> FEATURE:
<223> OTHER INFORMATION: Synthetic polypeptide (D4 mAb)

<400> SEQUENCE: 6

```
Gln Val Gln Leu Val Glu Ser Gly Gly Gly Leu Val Gln Pro Gly Gly
1               5                   10                  15

Ser Leu Arg Leu Ser Cys Val Ala Ser Gly Tyr Ser Tyr Ser Ile Gly
            20                  25                  30

Tyr Met Ala Trp Phe Arg Gln Ala Pro Gly Lys Glu Arg Ala Trp Val
        35                  40                  45

Ala Ser Arg Tyr Thr Gly Asp Gly Gly Ala Val Phe Asp Asp Ala Val
    50                  55                  60

Lys Gly Arg Phe Thr Thr Ser Gln Glu Ser Ala Gly Asn Thr Phe Asp
65                  70                  75                  80

Leu Gln Met Asp Ser Leu Lys Pro Glu Asp Thr Ala Met Tyr Tyr Cys
                85                  90                  95

Ala Ala Lys Gly Pro Gly Phe Gly Arg Trp Glu Tyr Trp Gly Arg Gly
            100                 105                 110

Thr Gln Val Thr Val Ser Ser
        115
```

<210> SEQ ID NO 7
<211> LENGTH: 22
<212> TYPE: PRT
<213> ORGANISM: Homo sapiens

<400> SEQUENCE: 7

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 8
<211> LENGTH: 45
<212> TYPE: PRT
<213> ORGANISM: Homo sapiens

<400> SEQUENCE: 8

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 9
<211> LENGTH: 21
<212> TYPE: PRT
<213> ORGANISM: Homo sapiens

<400> SEQUENCE: 9

```
Ile Tyr Ile Trp Ala Pro Leu Ala Gly Thr Cys Gly Val Leu Leu Leu
1               5                   10                  15

Ser Leu Val Ile Thr
            20
```

```
<210> SEQ ID NO 10
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 11
<211> LENGTH: 112
<212> TYPE: PRT
<213> ORGANISM: Homo sapiens

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Glu Gly Arg Gly Ser Leu Leu Thr Cys Gly Asp Val Glu Glu Asn Pro
1               5                   10                  15

Gly Pro

<210> SEQ ID NO 13
<211> LENGTH: 335
<212> TYPE: PRT
<213> ORGANISM: Homo sapiens

<400> SEQUENCE: 13

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45
```

-continued

Thr His Thr Pro Pro Leu Asp Pro Gln Glu Leu Asp Ile Leu Lys Thr
 50                  55                  60

Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 14
<211> LENGTH: 1092
<212> TYPE: DNA
<213> ORGANISM: Artificial Sequence
<220> FEATURE:
<223> OTHER INFORMATION: Synthetic polynucleotide

<400> SEQUENCE: 14
atgcaggtgc agctggtgga gtctggggga ggcttggtgc agcccggggg gtctctgaga    60
ctctcctgtg tagcctctgg atacagctac agtattggtt acatggcctg gttccgccag   120
gccccaggaa aggagcgcgc gtgggtcgcg tctcgatata ctggtgacgg tggcgcagtc   180
tttgacgacg ccgtgaaggg ccgattcacc acctcccaag agagtgccgg aacacgttc    240 gatttgcaaa tggacagcct gaaacctgag acactgcca tgtactattg cgcagcgaaa   300
gggcccggtt cgggcggtg ggagtactgg ggcgggggga cccaggtcac cgtctcctca   360
aagcttaaag caagcggcgg tcgccatcgc cagccgcgcg gctgggaaca gctgggcggt   420

| | |
|---|---|
| ggcggtggca gccccaccgg tgccgagttc ctgggcgacg gtggcgatgt gtcctttagc | 480 |
| acccgtggta cccagaactg gacggtagag cgcctgctgc aggcacatcg tcagctggaa | 540 |
| gagcgtggct atgtattcgt tggctaccac ggcactttc tggaagcagc tcagtccatc | 600 |
| gtgtttggtg gtgtccgtgc ccgttctcaa gacctggatg cgatttggcg tggtttctac | 660 |
| attgcaggcg atccagcgct ggcatacggt tatgcgcagg accaggaacc ggatgctcgt | 720 |
| ggtcgcattc gtaatggtgc gctgctgcgc gtatatgtgc cgcgttccag cctgccgggc | 780 |
| ttctaccgca ctagcctgac cctggccgcg ccggaggcgg cgggtgaagt ggaacgtctg | 840 |
| attggtcatc ctctgcctct cgcctggat gccatcaccg gcccagagga ggagggcggt | 900 |
| cgtctggaaa ccattctggg ctggccgctg gctgaacgta cggtcgttat tccgagcgcg | 960 |
| attcctaccg atcctcgtaa cgttggcggc gatctggacc catcttctat tccagataag | 1020 |
| gagcaggcaa tctccgcgct gccggattat gcaagccaac cgggtaaacc acctcgtgaa | 1080 |
| gatctgaaat aa | 1092 |

<210> SEQ ID NO 15
<211> LENGTH: 363
<212> TYPE: PRT
<213> ORGANISM: Artificial Sequence
<220> FEATURE:
<223> OTHER INFORMATION: Synthetic polypeptide

<400> SEQUENCE: 15

Met Gln Val Gln Leu Val Glu Ser Gly Gly Gly Leu Val Gln Pro Gly
1               5                   10                  15

Gly Ser Leu Arg Leu Ser Cys Val Ala Ser Gly Tyr Ser Tyr Ser Ile
            20                  25                  30

Gly Tyr Met Ala Trp Phe Arg Gln Ala Pro Gly Lys Glu Arg Ala Trp
        35                  40                  45

Val Ala Ser Arg Tyr Thr Gly Asp Gly Ala Val Phe Asp Asp Ala
    50                  55                  60

Val Lys Gly Arg Phe Thr Thr Ser Gln Glu Ser Ala Gly Asn Thr Phe
65                  70                  75                  80

Asp Leu Gln Met Asp Ser Leu Lys Pro Glu Asp Thr Ala Met Tyr Tyr
                85                  90                  95

Cys Ala Ala Lys Gly Pro Gly Phe Gly Arg Trp Glu Tyr Trp Gly Arg
            100                 105                 110

Gly Thr Gln Val Thr Val Ser Ser Lys Leu Lys Ala Ser Gly Gly Arg
        115                 120                 125

His Arg Gln Pro Arg Gly Trp Glu Gln Leu Gly Gly Gly Gly Ser
    130                 135                 140

Pro Thr Gly Ala Glu Phe Leu Gly Asp Gly Gly Asp Val Ser Phe Ser
145                 150                 155                 160

Thr Arg Gly Thr Gln Asn Trp Thr Val Glu Arg Leu Leu Gln Ala His
                165                 170                 175

Arg Gln Leu Glu Glu Arg Gly Tyr Val Phe Val Gly Tyr His Gly Thr
            180                 185                 190

Phe Leu Glu Ala Ala Gln Ser Ile Val Phe Gly Gly Val Arg Ala Arg
        195                 200                 205

Ser Gln Asp Leu Asp Ala Ile Trp Arg Gly Phe Tyr Ile Ala Gly Asp
    210                 215                 220

Pro Ala Leu Ala Tyr Gly Tyr Ala Gln Asp Gln Glu Pro Asp Ala Arg
225                 230                 235                 240

Gly Arg Ile Arg Asn Gly Ala Leu Leu Arg Val Tyr Val Pro Arg Ser
                245                 250                 255

Ser Leu Pro Gly Phe Tyr Arg Thr Ser Leu Thr Leu Ala Ala Pro Glu
            260                 265                 270

Ala Ala Gly Glu Val Glu Arg Leu Ile Gly His Pro Leu Pro Leu Arg
        275                 280                 285

Leu Asp Ala Ile Thr Gly Pro Glu Glu Gly Arg Leu Glu Thr
    290                 295                 300

Ile Leu Gly Trp Pro Leu Ala Glu Arg Thr Val Ile Pro Ser Ala
305                 310                 315                 320

Ile Pro Thr Asp Pro Arg Asn Val Gly Gly Asp Leu Asp Pro Ser Ser
                325                 330                 335

Ile Pro Asp Lys Glu Gln Ala Ile Ser Ala Leu Pro Asp Tyr Ala Ser
            340                 345                 350

Gln Pro Gly Lys Pro Pro Arg Glu Asp Leu Lys
        355                 360

<210> SEQ ID NO 16
<211> LENGTH: 1458
<212> TYPE: DNA
<213> ORGANISM: Artificial Sequence
<220> FEATURE:
<223> OTHER INFORMATION: Synthetic polynucleotide

<400> SEQUENCE: 16

```
atggaggttc agctgcagca gtctggggct gagcttgtga ggccaggggc ctcagtcaag     60
ttgtcctgca cagcttctgg ctttaacatt aaagacgact atatgcactg ggtgaagcag    120
aggcctgaac agggcctgga gtggattgga tggattgatc ctgagaatgg tgatactgaa    180
tatgcctcga gttccagggc aaggccact ataacagcag acacatcctc caacacagcc    240
tacctgcagc tcagcagcct gacatctgag gacactgccg tctattactg tactcgtagc    300
tccgtaggct actggggcca aggcaccact ctcacagtct cctcaggcgg aggcggatca    360
ggtggtggcg gatctggagg tggcggaagc gatgttgtga tgacccaaac tccactctcc    420
ctgcctgtca gtcttggaga tcaagcctcc atctcttgca gatctagtca gagccttgta    480
cacagtaatg gaaacaccta tttacattgg tacctgcaga agccaggcca gtctccaaag    540
ctcctgatct acaaagtttc aaccgatttt ctggggtcc cagacaggtt cagtggcagt    600
ggatcaggga cttatttcac actcaagatc agcagagtgg aggctgagga tctgggagtt    660
tatttctgct ctcaaagaac acatgttccg tacacgttcg ggggggggac caagctggag    720
ataaaaaagc ttaaagcaag cggcggtcgc catcgccagc cgcgcggctg ggaacagctg    780
ggcggtggcg gtggcagccc caccggtgcc gagttcctgg gcgacggtgg cgatgtgtcc    840
tttagcaccc gtggtaccca gaactggacg gtagagcgcc tgctgcaggc acatcgtcag    900
ctggaagagc gtggctatgt attcgttggc taccacggca cttttctgga agcagctcag    960
tccatcgtgt ttggtggtgt ccgtgcccgt tctcaagacc tggatgcgat tggcgtggt   1020
ttctacattg caggcgatcc agcgctggca tacggttatg cgcaggacca ggaaccggat   1080
gctcgtggtc gcattcgtaa tggtgcgctg ctgcgcgtat atgtgccgcg ttccagcctg   1140
ccgggcttct accgcactag cctgaccctg gccgcgccgg aggcggcggg tgaagtggaa   1200
cgtctgattg gtcatcctct gcctctgcgc ctgatgccca tcaccggccc agaggaggag   1260
ggcggtcgtc tggaaaccat tctgggctgg ccgctggctg aacgtacggt cgttattccg   1320
agcgcgattc ctaccgatcc tcgtaacgtt ggcggcgatc tggacccatc ttctattcca   1380
```
gataaggagc aggcaatctc cgcgctgccg gattatgcaa gccaaccggg taaaccacct    1440
cgtgaagatc tgaaataa    1458

<210> SEQ ID NO 17
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 17

Met Glu Val Gln Leu Gln Gln Ser Gly Ala Glu Leu Val Arg Pro Gly
1               5                   10                  15

Ala Ser Val Lys Leu Ser Cys Thr Ala Ser Gly Phe Asn Ile Lys Asp
            20                  25                  30

Asp Tyr Met His Trp Val Lys Gln Arg Pro Glu Gln Gly Leu Glu Trp
        35                  40                  45

Ile Gly Trp Ile Asp Pro Glu Asn Gly Asp Thr Glu Tyr Ala Ser Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Thr Ser Glu Asp Thr Ala Val Tyr Tyr
                85                  90                  95

Cys Thr Arg Ser Ser Val Gly Tyr Trp Gly Gln Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Val Val Met Thr Gln Thr Pro Leu Ser Leu Pro Val Ser
130                 135                 140

Leu Gly Asp Gln Ala Ser Ile Ser Cys Arg Ser Ser Gln Ser Leu Val
145                 150                 155                 160

His Ser Asn Gly Asn Thr Tyr Leu His Trp Tyr Leu Gln Lys Pro Gly
                165                 170                 175

Gln Ser Pro Lys Leu Leu Ile Tyr Lys Val Ser Asn Arg Phe Ser Gly
            180                 185                 190

Val Pro Asp Arg Phe Ser Gly Ser Gly Ser Gly Thr Tyr Phe Thr Leu
        195                 200                 205

Lys Ile Ser Arg Val Glu Ala Glu Asp Leu Gly Val Tyr Phe Cys Ser
    210                 215                 220

Gln Arg Thr His Val Pro Tyr Thr Phe Gly Gly Gly Thr Lys Leu Glu
225                 230                 235                 240

Ile Lys Lys Leu Lys Ala Ser Gly Gly Arg His Arg Gln Pro Arg Gly
                245                 250                 255

Trp Glu Gln Leu Gly Gly Gly Gly Ser Pro Thr Gly Ala Glu Phe
            260                 265                 270

Leu Gly Asp Gly Gly Asp Val Ser Phe Ser Thr Arg Gly Thr Gln Asn
        275                 280                 285

Trp Thr Val Glu Arg Leu Leu Gln Ala His Arg Gln Leu Glu Glu Arg
    290                 295                 300

Gly Tyr Val Phe Val Gly Tyr His Gly Thr Phe Leu Glu Ala Ala Gln
305                 310                 315                 320

Ser Ile Val Phe Gly Gly Val Arg Ala Arg Ser Gln Asp Leu Asp Ala
                325                 330                 335

Ile Trp Arg Gly Phe Tyr Ile Ala Gly Asp Pro Ala Leu Ala Tyr Gly

```
                    340                 345                 350
Tyr Ala Gln Asp Gln Glu Pro Asp Ala Arg Gly Arg Ile Arg Asn Gly
            355                 360                 365

Ala Leu Leu Arg Val Tyr Val Pro Arg Ser Ser Leu Pro Gly Phe Tyr
        370                 375                 380

Arg Thr Ser Leu Thr Leu Ala Ala Pro Glu Ala Ala Gly Glu Val Glu
385                 390                 395                 400

Arg Leu Ile Gly His Pro Leu Pro Leu Arg Leu Asp Ala Ile Thr Gly
                405                 410                 415

Pro Glu Glu Glu Gly Gly Arg Leu Glu Thr Ile Leu Gly Trp Pro Leu
            420                 425                 430

Ala Glu Arg Thr Val Val Ile Pro Ser Ala Ile Pro Thr Asp Pro Arg
        435                 440                 445

Asn Val Gly Gly Asp Leu Asp Pro Ser Ser Ile Pro Asp Lys Glu Gln
    450                 455                 460

Ala Ile Ser Ala Leu Pro Asp Tyr Ala Ser Gln Pro Gly Lys Pro Pro
465                 470                 475                 480

Arg Glu Asp Leu Lys
            485

<210> SEQ ID NO 18
<211> LENGTH: 1458
<212> TYPE: DNA
<213> ORGANISM: Artificial Sequence
<220> FEATURE:
<223> OTHER INFORMATION: Synthetic polynucleotide

<400> SEQUENCE: 18
atgcaggtgc agctggtgga gtctggggga ggcttggtgc agcccggggg gtctctgaga      60
ctctcctgtg tagcctctgg atacagctac agtattggtt acatggcctg gttccgccag     120
gccccaggaa aggagcgcgc gtgggtcgcg tctcgatata ctggtgacgg tggcgcagtc     180
tttgacgacg ccgtgaaggg ccgattcacc acctcccaag agagtgccgg aacacgttc     240 gatttgcaaa tggacagcct gaaacctgag gacactgcca tgtactattg cgcagcgaaa     300
gggcccggtt tcgggcggtg ggagtactgg ggccggggga cccaggtcac cgtctcctca     360
gcggcggcgc aggtgcagct ggtggagtct gggggaggct tggtgcagcc ggggggtct     420 ctgagactct cctgtgtagc ctctggatac agctacagta ttggttacat ggcctggttc     480
cgccaggccc caggaaagga gcgcgcgtgg gtcgcgtctc gatatactgg tgacggtggc     540
gcagtctttg acgacgccgt gaagggccga ttcaccacct cccaagagag tgccgggaac     600
acgttcgatt tgcaaatgga cagcctgaaa cctgaggaca ctgccatgta ctattgcgca     660
gcgaaagggc ccggtttcgg cggtgggag tactggggcc gggggaccca ggtcaccgtc     720
tcctcaaagc ttaaagcaag cggcggtcgc atcgccagc gcgcggctg gaacagctg     780 ggcggtggcg gtggcagccc caccggtgcc gagttcctgg cgacggtgg cgatgtgtcc     840 tttagcaccc gtggtaccca gaactggacg gtagagcgcc tgctgcaggc acatcgtcag     900
ctggaagagc gtggctatgt attcgttggc taccacggca ctttttctgg agcagctcag     960
tccatcgtgt ttggtggtgt ccgtgcccgt tctcaagacc tggatgcgat ttggcgtggt    1020
ttctacattg caggcgatcc agcgctggca tacggttatg cgcaggacca ggaaccggat    1080
gctcgtggtc gcattcgtaa tgtgcgctg ctgcgcgtat atgtgccgcg ttccagcctg    1140
ccgggcttct accgcactag cctgaccctg gccgcgccgg aggcggcggg tgaagtggaa    1200
```

```
cgtctgattg gtcatcctct gcctctgcgc ctggatgcca tcaccggccc agaggaggag   1260
ggcggtcgtc tggaaaccat tctgggctgg ccgctggctg aacgtacggt cgttattccg   1320
agcgcgattc ctaccgatcc tcgtaacgtt ggcggcgatc tggacccatc ttctattcca   1380
gataaggagc aggcaatctc cgcgctgccg gattatgcaa gccaaccggg taaaccacct   1440
cgtgaagatc tgaaataa                                                 1458
```

<210> SEQ ID NO 19
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 19

```
Met Gln Val Gln Leu Val Glu Ser Gly Gly Gly Leu Val Gln Pro Gly
1               5                   10                  15

Gly Ser Leu Arg Leu Ser Cys Val Ala Ser Gly Tyr Ser Tyr Ser Ile
            20                  25                  30

Gly Tyr Met Ala Trp Phe Arg Gln Ala Pro Gly Lys Glu Arg Ala Trp
        35                  40                  45

Val Ala Ser Arg Tyr Thr Gly Asp Gly Gly Ala Val Phe Asp Asp Ala
    50                  55                  60

Val Lys Gly Arg Phe Thr Thr Ser Gln Glu Ser Ala Gly Asn Thr Phe
65                  70                  75                  80

Asp Leu Gln Met Asp Ser Leu Lys Pro Glu Asp Thr Ala Met Tyr Tyr
                85                  90                  95

Cys Ala Ala Lys Gly Pro Gly Phe Gly Arg Trp Glu Tyr Trp Gly Arg
            100                 105                 110

Gly Thr Gln Val Thr Val Ser Ser Ala Ala Ala Gln Val Gln Leu Val
        115                 120                 125

Glu Ser Gly Gly Gly Leu Val Gln Pro Gly Gly Ser Leu Arg Leu Ser
    130                 135                 140

Cys Val Ala Ser Gly Tyr Ser Tyr Ser Ile Gly Tyr Met Ala Trp Phe
145                 150                 155                 160

Arg Gln Ala Pro Gly Lys Glu Arg Ala Trp Val Ala Ser Arg Tyr Thr
                165                 170                 175

Gly Asp Gly Gly Ala Val Phe Asp Asp Ala Val Lys Gly Arg Phe Thr
            180                 185                 190

Thr Ser Gln Glu Ser Ala Gly Asn Thr Phe Asp Leu Gln Met Asp Ser
        195                 200                 205

Leu Lys Pro Glu Asp Thr Ala Met Tyr Tyr Cys Ala Ala Lys Gly Pro
    210                 215                 220

Gly Phe Gly Arg Trp Glu Tyr Trp Gly Arg Gly Thr Gln Val Thr Val
225                 230                 235                 240

Ser Ser Lys Leu Lys Ala Ser Gly Gly Arg His Arg Gln Pro Arg Gly
                245                 250                 255

Trp Glu Gln Leu Gly Gly Gly Gly Ser Pro Thr Gly Ala Glu Phe
            260                 265                 270

Leu Gly Asp Gly Gly Asp Val Ser Phe Ser Thr Arg Gly Thr Gln Asn
        275                 280                 285

Trp Thr Val Glu Arg Leu Leu Gln Ala His Arg Gln Leu Glu Glu Arg
    290                 295                 300

Gly Tyr Val Phe Val Gly Tyr His Gly Thr Phe Leu Glu Ala Ala Gln
305                 310                 315                 320
```

```
Ser Ile Val Phe Gly Gly Val Arg Ala Arg Ser Gln Asp Leu Asp Ala
            325                 330                 335

Ile Trp Arg Gly Phe Tyr Ile Ala Gly Asp Pro Ala Leu Ala Tyr Gly
            340                 345                 350

Tyr Ala Gln Asp Gln Glu Pro Asp Ala Arg Gly Arg Ile Arg Asn Gly
            355                 360                 365

Ala Leu Leu Arg Val Tyr Val Pro Arg Ser Ser Leu Pro Gly Phe Tyr
        370                 375                 380

Arg Thr Ser Leu Thr Leu Ala Ala Pro Glu Ala Ala Gly Glu Val Glu
385                 390                 395                 400

Arg Leu Ile Gly His Pro Leu Pro Leu Arg Leu Asp Ala Ile Thr Gly
            405                 410                 415

Pro Glu Glu Gly Gly Arg Leu Glu Thr Ile Leu Gly Trp Pro Leu
            420                 425                 430

Ala Glu Arg Thr Val Val Ile Pro Ser Ala Ile Pro Thr Asp Pro Arg
            435                 440                 445

Asn Val Gly Gly Asp Leu Asp Pro Ser Ser Ile Pro Asp Lys Glu Gln
        450                 455                 460

Ala Ile Ser Ala Leu Pro Asp Tyr Ala Ser Gln Pro Gly Lys Pro Pro
465                 470                 475                 480

Arg Glu Asp Leu Lys
            485

<210> SEQ ID NO 20
<211> LENGTH: 1458
<212> TYPE: DNA
<213> ORGANISM: Artificial Sequence
<220> FEATURE:
<223> OTHER INFORMATION: Synthetic polynucleotide

<400> SEQUENCE: 20
atgcaggtgc agctggtgga gtctggggga ggcttggtgc agcccggggg gtctctgaga      60
ctctcctgtg tagcctctgg atacagctac agtattggtt acatggcctg gttccgccag     120
gccccaggaa aggagcgcgc gtgggtcgcg tctcgatata ctggtgacgg tgcgcagtc      180 tttgacgacg ccgtgaaggg ccgattcacc acctcccaag agagtgccgg aacacgttc     240 gatttgcaaa tggacagcct gaaacctgag acactgccat gtactattg cgcagcgaaa     300 gggcccggtt cgggcggtg ggagtactgg ggccggggga cccaggtcac cgtctcctca     360
ggcggcagcc aggtgcagct ggtggagtct gggggaggct ggtgcagcc ggggggtct     420 ctgagactct cctgtgtagc ctctggatac agctacagta ttggttacat ggcctggttc     480
cgccaggccc caggaaagga gcgcgcgtgg gtcgcgtctc gatatactgg tgacggtggc     540
gcagtctttg acgacgccgt gaagggccga ttcaccacct cccaagagag tgccgggaac     600
acgttcgatt tgcaaatgga cagcctgaaa cctgaggaca ctgccatgta ctattgcgca     660
gcgaaagggc ccggtttcgg cggtgggag tactggggcc ggggaccca ggtcaccgtc     720 tcctcaaagc ttaaagcaag cggcggtcgc catcgccagc cgcgcggctg gaacagctg     780 ggcggtggcg gtggcagccc caccggtgcc gagttcctgg cgacggtgg cgatgtgtcc     840 tttagcaccc gtggtaccca gaactggacg gtagagcgcc tgctgcaggc acatcgtcag     900
ctggaagagc gtggctatgt attcgttggc taccacggca ctttctggga agcagctcag     960
tccatcgtgt ttggtggtgt ccgtgcccgt ctctcaagacc tggatgcgat ttggcgtggt    1020
ttctacattg caggcgatcc agcgctggca tacggttatg cgcaggacca ggaaccggat    1080
```

```
gctcgtggtc gcattcgtaa tggtgcgctg ctgcgcgtat atgtgccgcg ttccagcctg    1140
ccgggcttct accgcactag cctgaccctg gccgcgccgg aggcggcggg tgaagtggaa    1200
cgtctgattg tcatcctct  gcctctgcgc ctggatgcca tcaccggccc agaggaggag    1260
ggcggtcgtc tggaaaccat tctgggctgg ccgctggctg aacgtacggt cgttattccg    1320
agcgcgattc ctaccgatcc tcgtaacgtt ggcggcgatc tggacccatc ttctattcca    1380
gataaggagc aggcaatctc cgcgctgccg gattatgcaa gccaaccggg taaaccacct    1440
cgtgaagatc tgaaataa                                                  1458
```

<210> SEQ ID NO 21
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 21

```
Met Gln Val Gln Leu Val Glu Ser Gly Gly Gly Leu Val Gln Pro Gly
1               5                   10                  15

Gly Ser Leu Arg Leu Ser Cys Val Ala Ser Gly Tyr Ser Tyr Ser Ile
            20                  25                  30

Gly Tyr Met Ala Trp Phe Arg Gln Ala Pro Gly Lys Glu Arg Ala Trp
        35                  40                  45

Val Ala Ser Arg Tyr Thr Gly Asp Gly Gly Ala Val Phe Asp Asp Ala
    50                  55                  60

Val Lys Gly Arg Phe Thr Thr Ser Gln Glu Ser Ala Gly Asn Thr Phe
65                  70                  75                  80

Asp Leu Gln Met Asp Ser Leu Lys Pro Glu Asp Thr Ala Met Tyr Tyr
                85                  90                  95

Cys Ala Ala Lys Gly Pro Gly Phe Gly Arg Trp Glu Tyr Trp Gly Arg
            100                 105                 110

Gly Thr Gln Val Thr Val Ser Ser Gly Gly Ser Gln Val Gln Leu Val
        115                 120                 125

Glu Ser Gly Gly Gly Leu Val Gln Pro Gly Gly Ser Leu Arg Leu Ser
    130                 135                 140

Cys Val Ala Ser Gly Tyr Ser Tyr Ser Ile Gly Tyr Met Ala Trp Phe
145                 150                 155                 160

Arg Gln Ala Pro Gly Lys Glu Arg Ala Trp Val Ala Ser Arg Tyr Thr
                165                 170                 175

Gly Asp Gly Gly Ala Val Phe Asp Asp Ala Val Lys Gly Arg Phe Thr
            180                 185                 190

Thr Ser Gln Glu Ser Ala Gly Asn Thr Phe Asp Leu Gln Met Asp Ser
        195                 200                 205

Leu Lys Pro Glu Asp Thr Ala Met Tyr Tyr Cys Ala Ala Lys Gly Pro
    210                 215                 220

Gly Phe Gly Arg Trp Glu Tyr Trp Gly Arg Gly Thr Gln Val Thr Val
225                 230                 235                 240

Ser Ser Lys Leu Lys Ala Ser Gly Gly Arg His Arg Gln Pro Arg Gly
                245                 250                 255

Trp Glu Gln Leu Gly Gly Gly Gly Ser Pro Thr Gly Ala Glu Phe
            260                 265                 270

Leu Gly Asp Gly Gly Asp Val Ser Phe Ser Thr Arg Gly Thr Gln Asn
        275                 280                 285
```

-continued

```
Trp Thr Val Glu Arg Leu Leu Gln Ala His Arg Gln Leu Glu Glu Arg
    290                 295                 300

Gly Tyr Val Phe Val Gly Tyr His Gly Thr Phe Leu Glu Ala Ala Gln
305                 310                 315                 320

Ser Ile Val Phe Gly Gly Val Arg Ala Arg Ser Gln Asp Leu Asp Ala
                325                 330                 335

Ile Trp Arg Gly Phe Tyr Ile Ala Gly Asp Pro Ala Leu Ala Tyr Gly
                340                 345                 350

Tyr Ala Gln Asp Gln Glu Pro Asp Ala Arg Gly Arg Ile Arg Asn Gly
            355                 360                 365

Ala Leu Leu Arg Val Tyr Val Pro Arg Ser Ser Leu Pro Gly Phe Tyr
    370                 375                 380

Arg Thr Ser Leu Thr Leu Ala Ala Pro Glu Ala Ala Gly Glu Val Glu
385                 390                 395                 400

Arg Leu Ile Gly His Pro Leu Pro Leu Arg Leu Asp Ala Ile Thr Gly
                405                 410                 415

Pro Glu Glu Glu Gly Gly Arg Leu Glu Thr Ile Leu Gly Trp Pro Leu
                420                 425                 430

Ala Glu Arg Thr Val Val Ile Pro Ser Ala Ile Pro Thr Asp Pro Arg
            435                 440                 445

Asn Val Gly Gly Asp Leu Asp Pro Ser Ser Ile Pro Asp Lys Glu Gln
    450                 455                 460

Ala Ile Ser Ala Leu Pro Asp Tyr Ala Ser Gln Pro Gly Lys Pro Pro
465                 470                 475                 480

Arg Glu Asp Leu Lys
                485
```

HIGH AFFINITY MONOCLONAL ANTIBODIES TARGETING GLYPICAN-1 AND METHODS OF USE

CROSS REFERENCE TO RELATED APPLICATIONS

This application is the U.S. National Stage of International Application No. PCT/US2020/013739, filed Jan. 15, 2020, which was published in English under PCT Article 21(2), which claims the benefit of U.S. Provisional Application No. 62/795,415, filed Jan. 22, 2019. The above-listed applications are herein incorporated by reference in their entirety.

ACKNOWLEDGMENT OF GOVERNMENT SUPPORT

This invention was made with government support under project number Z01 BC010891 awarded by the National Institutes of Health. The government has certain rights in the invention.

FIELD

This disclosure concerns monoclonal antibodies that specifically bind glypican-1 (GPC1) with high affinity and use of the monoclonal antibodies, such as for diagnosing and treating GPC1-expressing tumors.

BACKGROUND

Glypicans are cell-surface heparan sulfate proteoglycans (HSPGs) having a membrane-associated protein core that is anchored to the cytoplasmic membrane via a glycosyl phosphatidylinositol (GPI) linkage. After translation, HSPGs are modified by covalent attachment of two or more chains of linear polysaccharide heparan sulfate (Davies et al., *Clin Cancer Res* 10:5178-5186, 2004). Six glypicans have been identified in mammals, referred to as GPC1 to GPC6. Several members of the GPC family have been implicated in the development or progression of cancer. GPC1 is overexpressed in a variety of different cancers, including pancreatic cancer, breast cancer, glioma, colorectal cancer and ovarian cancer.

Pancreatic cancer is the fourth most common cause of death from cancer in the United States. The overall 5-year survival rate for this deadly disease is less than 5%. While immunotherapy with chimeric antigen receptor (CAR) T cells has shown promise in certain hematological malignancies, their efficacy for solid tumors, including pancreatic cancer, remains elusive. Thus, there remains an urgent need to identify and validate a new target of CAR T-cell therapy for patients with pancreatic and other types of cancer.

SUMMARY

The present disclosure describes a mouse monoclonal antibody and a camel single-domain monoclonal antibody, both of which target GPC1. The GPC1-specific antibodies, referred to as HM2 and D4, specifically bind GPC1 with high affinity. Chimeric antigen receptor (CAR) T cells comprised of the disclosed antibodies are capable of potently killing GPC1-positive tumor cells in vitro and in vivo.

Provided herein are monoclonal antibodies that bind, such as specifically bind, GPC1. In some embodiments, the monoclonal antibody includes the complementarity determining region (CDR) sequences of HM2 or D4. Also provided herein are conjugates that include a disclosed monoclonal antibody. In some examples, provided are CARs (and CAR-expressing T cells and natural killer cells), immunoconjugates (such as immunotoxins), multi-specific antibodies (such as bispecific T-cell engagers), antibody-drug conjugates (ADCs), antibody-nanoparticle conjugates, antibody-radioisotope conjugates (such as for cancer diagnostics and immunoPET imaging) and fusion proteins that include a monoclonal antibody disclosed herein.

Also provided herein are GPC1-specific monoclonal antibodies modified to enable their use with a universal CAR system. In some embodiments, the GPC1-specific monoclonal antibody is fused to one component of a specific binding pair. In some examples, the monoclonal antibody is fused to a leucine zipper, biotin, or a sortase recognition motif.

Compositions that include a GPC1-specific monoclonal antibody and a pharmaceutically acceptable carrier are also provided by the present disclosure.

Also provided herein are nucleic acid molecules and vectors encoding the GPC1-specific monoclonal antibodies, CARs, immunoconjugates (such as immunotoxins), multi-specific antibodies and fusion proteins disclosed herein.

Further provided are nucleic acid constructs that encode both a GPC1-specific CAR and a truncated human epidermal growth factor receptor (huEGFRt). The encoded CARs include a GPC1-specific monoclonal antibody fused to an extracellular hinge region, a transmembrane region, an intracellular co-stimulatory domain and an intracellular signaling domain. The huEGFRt includes two EGFR extracellular domains (Domain III and Domain IV) and the EGFR transmembrane domain, but lacks the two membrane distal extracellular domains and all intracellular domains. In some embodiments, the nucleic acid molecule includes, in the 5' to 3' direction, a nucleic acid encoding a first signal sequence; a nucleic acid encoding a GPC1-specific antibody; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second signal sequence; and a nucleic acid encoding a huEGFRt. Also provided are vectors, such as viral vectors, that include a nucleic acid molecule disclosed herein. Isolated cells, such as T lymphocytes, that co-express the disclosed CARs and huEGFRt are also disclosed.

Methods of treating a GPC1-positive cancer in a subject, and methods of inhibiting tumor growth or metastasis of a GPC1-positive cancer in a subject are also provided. In some embodiments, the methods include administering to the subject a monoclonal antibody disclosed herein, or administering to the subject a CAR (or CAR T cells or CAR NK cells), immunoconjugate (such as an immunotoxin), ADC, multi-specific antibody, antibody-nanoparticle conjugate or fusion protein comprising a monoclonal antibody disclosed herein.

Further provided herein are methods of detecting expression of GPC1 in a sample. In some embodiments, the method includes contacting the sample with a monoclonal antibody disclosed herein, and detecting binding of the antibody to the sample.

Also provided are methods of diagnosing a subject as having a GPC1-positive cancer. In some embodiments, the method includes contacting a sample obtained from the subject with a monoclonal antibody disclosed herein, and detecting binding of the antibody to the sample. In some examples, the sample is a serum sample containing exosomes.

The foregoing and other objects and features of the disclosure will become more apparent from the following detailed description, which proceeds with reference to the accompanying figures.

BRIEF DESCRIPTION OF THE DRAWINGS

(FIG. 1A) Polyclonal phage ELISA from the output phage of each round of panning HuGPC1: human GPC1. (FIG. 1B) Monoclonal phage ELISA analysis of cross-reactivity of GPC1 binder D4 to mouse GPC1 (MsGPC1) and human glypicans.

(FIG. 8A) Schematic diagram of the lentiviral construct expressing a CAR targeting GPC1 along with truncated human EGFR (huEGFRt) using the T2A ribosomal skipping sequence. (FIG. 8B) GPC1-targeted CAR expression on human T cells transduced with lentiviral particles were analyzed using flow cytometry by detection of huEGFRt expression.

FIGS. 9A-9D: Cytolytic activity of HM2 and D4 CAR T cells in vitro. Luciferase expressing 2B9 (FIG. 9A), H8 (FIG. 9B), T3M4 (FIG. 9C) and A431 (FIG. 9D) cells were co-cultured with mock, HM2 or D4 CAR-transduced T cells at the indicated E:T ratios for 20 hours, and specific lysis was measured using a luminescent-based cytolytic assay.

(FIG. 11A) Experimental schematic. 2B9 tumor-bearing NSG mice were treated with peritoneal injection of either mock T cells or 30×10$^6$ CAR T cells at day 11 after tumor cell inoculation. Tumor burden was monitored by bioluminescent imaging. (FIG. 11B) HM2 and D4 CAR T cells demonstrated potent antitumor activity and mediated eradication of 2B9 xenograft tumors. (FIG. 11C) Quantitation of bioluminescence in mice treated in FIG. 11B. (FIG. 11D) Body weight of mice treated in FIG. 11B. (FIG. 11E) Graph showing the percentage of CAR T cells in the spleens of mock-treated, HM2-treated and D4-treated mice. Genomic DNA was extracted from the spleens of select mice and analyzed by droplet digital PCR (ddPCR) to quantify CAR vector positive cells.

(FIG. 12A) Schematic of anti-GPC1 immunotoxins based on the HM2 and D4 antibodies. LR: A truncated *Pseudomonas* exotoxin A (lacking domain II). (FIG. 12B) Reducing and non-reducing SDS-PAGE gel image for D4-LR and HM2-LR.

(FIG. 13A) Graph of Octet assay showing binding affinity of HM2-LR and D4-LR for GPC1 antigen. (FIG. 13B) Table showing specific values for $K_D$, $K_{on}$ and $K_{dis}$.

(FIG. 15A) Schematic of the bivalent D4-D4-LR immunotoxins: D4-AAA-D4-LR and D4-GGS-D4-LR. (FIG. 15B) Reducing and non-reducing SDS-PAGE gel image of the D4-D4-LR immunotoxins.

by tail vein injection on the days indicated with a black arrow. Experimental groups contained five mice. (FIG. 18A) Tumor volume for each mouse. (FIG. 18B) Average tumor volume for each experimental group. (FIG. 18C) Average body weight of mice during experimental treatment. (FIG. 18D) Survival curves of immunotoxin-treated mice.

SEQUENCE LISTING

Figure 1A:
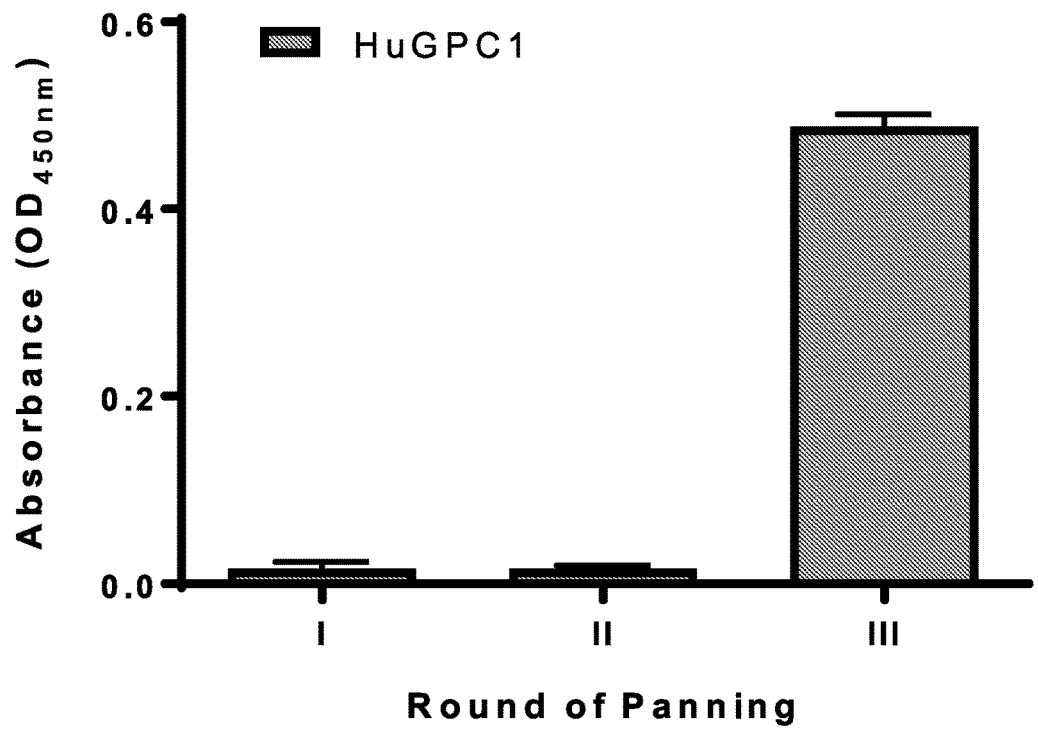
FIGS. 1A-1B: Isolation of a GPC1-specific camel single-domain monoclonal antibody by phage display.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 10, 2021, 34.0 KB, which is incorporated by reference herein. In the accompanying sequence listing:

SEQ ID NO: 1 is the nucleotide sequence of the VH domain of the HM2 antibody.

SEQ ID NO: 2 is the amino acid sequence of the VH domain of the HM2 antibody.

SEQ ID NO: 3 is the nucleotide sequence of the VL domain of the HM2 antibody.

SEQ ID NO: 4 is the amino acid sequence of the VL domain of the HM2 antibody.

SEQ ID NO: 5 is the nucleotide sequence of the D4 antibody.

SEQ ID NO: 6 is the amino acid sequence of the D4 antibody.

SEQ ID NO: 7 is an exemplary GMCSFRss amino acid sequence.

SEQ ID NO: 8 is an exemplary CD8α hinge region amino acid sequence.

SEQ ID NO: 9 is an exemplary CD8α transmembrane region amino acid sequence.

SEQ ID NO: 10 is an exemplary 4-1BB amino acid sequence.

SEQ ID NO: 11 is an exemplary CD3ζ amino acid sequence.

SEQ ID NO: 12 is an exemplary self-cleaving T2A peptide amino acid sequence.

SEQ ID NO: 13 is an exemplary huEGFRt amino acid sequence.

SEQ ID NO: 14 is the nucleotide sequence encoding the D4-LR immunotoxin.

SEQ ID NO: 15 is the amino acid sequence of the D4-LR immunotoxin.

SEQ ID NO: 16 is the nucleotide sequence encoding the HM2-LR immunotoxin.

SEQ ID NO: 17 is the amino acid sequence of the HM2-LR immunotoxin.

SEQ ID NO: 18 is the nucleotide sequence encoding the D4-AAA-D4-LR immunotoxin.

SEQ ID NO: 19 is the amino acid sequence of the D4-AAA-D4-LR immunotoxin.

SEQ ID NO: 20 is the nucleotide sequence encoding the D4-GGS-D4-LR immunotoxin.

SEQ ID NO: 21 is the amino acid sequence of the D4-GGS-D4-LR immunotoxin.

DETAILED DESCRIPTION

| Abbreviations | |
|---|---|
| ADC | antibody-drug conjugate |
| ADCC | antibody-dependent cell-mediated cytotoxicity |
| CAR | chimeric antigen receptor |
| CDR | complementarity determining region |
| CTL | cytotoxic T lymphocyte |
| E:T | effector to target |
| EGF | epidermal growth factor |
| EGFR | epidermal growth factor receptor |
| ELISA | enzyme-linked immunosorbent assay |
| FACS | fluorescence activated cells sorting |
| GMCSFRss | granulocyte-macrophage colony stimulating factor receptor sequence |
| GPC1 | glypican-1 |
| GPI | glycosyl phosphatidylinositol |
| HSPG | heparan sulfate proteoglycan |
| huEGFRt | human truncated epidermal growth factor receptor |
| Ig | immunoglobulin |
| NK | natural killer |
| PE | *Pseudomonas* exotoxin |
| PET | positron emission tomography |

II. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response. An exemplary amino acid sequence of 4-1BB is set forth herein as SEQ ID NO: 10.

Administration: To provide or give a subject an agent, such as an anti-GPC1 antibody provided herein, by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and is functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., JMB 273,927-948, 1997; the "Chothia" numbering scheme), Kunik et al. (see Kunik et al., *PLoS Comput Biol* 8:e1002388, 2012; and Kunik et al., *Nucleic Acids Res* 40(Web Server issue):W521-524, 2012; "Paratome CDRs") and the ImMunoGeneTics (IMGT) database (see, Lefranc, *Nucleic Acids Res* 29:207-9, 2001; the "IMGT" numbering scheme). The Kabat, Paratome and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_HH$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by known methods. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Antibody-drug conjugate (ADC): A molecule that includes an antibody (or antigen-binding fragment of an antibody) conjugated to a drug, such as a cytotoxic agent (such as covalently attached). ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand crosslinking agents (for example, pyrrolobenzodiazepines; PDBs). In some cases, the ADC is a bi-specific ADC, which is comprised of two monoclonal antibodies or antigen-fragments thereof, each directed to a different antigen or epitope, conjugated to a drug.

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In other embodiments, antibody affinity is measured by flow cytometry or by surface plasmon reference. An antibody that "specifically binds" an antigen (such as GPC1) is an antibody that binds the antigen with high affinity and does not significantly bind other unrelated antigens.

In some examples, an antibody or fragment thereof (such as an anti-GPC1 antibody provided herein) specifically binds to a target (such as a GPC1) with a binding constant that is at least $10^3$ $M^{-1}$ greater, $10^4 M^{-1}$ greater or $10^5$ $M^{-1}$ greater than a binding constant for other molecules in a sample or subject. In some examples, an antibody (e.g., monoclonal antibody) or fragments thereof, has an equilibrium constant (Kd) of 10 nM or less, such as 9 nM or less, 8.1 nM or less, 8 nM or less, 7 nM or less, 6 nM or less, 6.5 nM or less, 6.3 nM or less, 5 nM or less, 4.3 nM or less, 4 nM or less, 3 nM or less, 2 nM or less, 1.5 nM or less, 1.5 nM or less, 1.4 nM or less, 1.3 nM or less, or 1.2 nM or less. For example, an antibody or fragment thereof binds to a target, such as GPC1 with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, at least about $5.0 \times 10^{-8}$ M, at least about $1 \times 10^{-9}$ M, at least about $1.3 \times 10^{-9}$ M, at least about $1.5 \times 10^{-9}$ M, at least about $2 \times 10^{-9}$ M, at least about $3 \times 10^{-9}$ M, at least about $4 \times 10^{-9}$ M, at least about $4.3 \times 10^{-9}$ M, at least about $5 \times 10^{-9}$ M, at least about $6 \times 10^{-9}$ M, at least about $6.3 \times 10^{-9}$ M, at least about $6.9 \times 10^{0.9}$M, at least about $7 \times 10^{-9}$ M, at least about $8 \times 10^{-9}$ M, at least about $8.1 \times 10^{-9}$ M, or at least about $10 \times 10^{-9}$ M. In certain embodiments, a specific binding agent that binds to its target has a dissociation constant (Kd) of ≤100 nM, ≤10 nM, ≤9 nM, ≤8 nM, ≤7 nM, ≤6.9 nM, ≤6.5 nM, ≤6.3 nM, ≤5 nM, ≤4 nM, ≤4.5 nM, ≤3 nM, ≤2 nM, ≤1.5 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$ M to $10^{-13}$ M). In one embodiment, Kd is measured by a radiolabeled antigen binding assay (RIA) performed with the Fab version of an antibody of interest and its antigen (see, e.g., Chen et al., *J. Mol. Biol.* 293:865-881, 1999). In another example, Kd is measured using surface plasmon resonance assays using a BIA-CORES-2000 or a BIACORES-3000 (BIAcore, Inc., Piscataway, N.J.) at 25° C. with immobilized antigen CMS chips at about 10 response units (RU).

Bispecific antibody: A recombinant protein that includes antigen-binding fragments of two different monoclonal antibodies and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen (such as GPC1). Similarly, a multi-specific antibody is a recombinant protein that includes antigen-binding fragments of at least two different monoclonal antibodies, such as two, three or four different monoclonal antibodies.

Breast cancer: A type of cancer that forms in tissues of the breast, usually the ducts and lobules. Types of breast cancer include, for example, ductal carcinoma in situ, invasive ductal carcinoma, triple negative breast cancer, inflammatory breast cancer, metastatic breast cancer, medullary carcinoma, tubular carcinoma and mucinous carcinoma. Triple negative breast cancer refers to a type of breast cancer in which the cancer cells do not express estrogen receptors, progesterone receptors or significant levels of HER2/neu protein. Triple negative breast cancer is also called ER-negative PR-negative HER2/neu-negative breast cancer.

Chemotherapeutic agent: Any chemical agent with therapeutic usefulness in the treatment of diseases characterized by abnormal cell growth. Such diseases include tumors, neoplasms, and cancer. In one embodiment, a chemotherapeutic agent is an agent of use in treating a GPC1-positive tumor. In one embodiment, a chemotherapeutic agent is a radioactive compound. Exemplary chemotherapeutic agents that can be used with the methods provided herein are disclosed in Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds GPC1 used in combination with a radioactive or chemical compound. In one example, a chemotherapeutic agent is a biologic, such as a therapeutic antibody (e.g., therapeutic monoclonal antibody), such as an anti-GPC1 antibody provided herein, as well as other anti-cancer antibodies, such as anti-PD1 or anti-PDL1 (e.g., pembrolizumab and nivolumab), anti-EGFR (e.g., cetuximab), or anti-VEGF (e.g., bevacizumab).

Chimeric antigen receptor (CAR): A chimeric molecule that includes an antigen-binding portion (such as a scFv or single-domain antibody) and a signaling domain, such as a signaling domain from a T cell receptor (for example, CD3ζ). Typically, CARs are comprised of an antigen-binding moiety, a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10. In some examples, the CAR is multispecific (such as bispecific) or bicistronic. A multispecific CAR is a single CAR molecule comprised of at least two antigen-binding domains (such as scFvs and/or single-domain antibodies) that each bind a different antigen or a different epitope on the same antigen (see, for example, US 2018/0230225). For example, a bispecific CAR refers to a single CAR molecule having two antigen-binding domains that each bind a different antigen. A bicistronic CAR refers to two complete CAR molecules, each containing an antigen-binding moiety that binds a different antigen. In some cases, a bicistronic CAR construct expresses two complete CAR molecules that are linked by a cleavage linker. T cells or NK cells expressing a bispecific or bicistronic CAR can bind cells that express both of the antigens to which the binding moieties are directed (see, for example, Qin et al., *Blood* 130:810, 2017; and WO/2018/213337).

Colorectal cancer: A type of cancer that develops in the colon or the rectum. The most common type of colorectal cancer is colorectal adenocarcinoma, which accounts for approximately 95% of all colorectal cancers. Adenocarcinomas develop in the cells lining the inside of the colon and/or rectum. Other types of colorectal cancers include gastrointestinal carcinoid tumors, metastatic colorectal cancer, primary colorectal lymphoma (a type of non-Hodgkin's lymphoma), gastrointestinal stromal tumors (classified as a sarcoma and arising from interstitial cells of Cajal), leiomyosarcoma (arising from smooth muscle cells) and colorectal melanoma.

Complementarity determining region (CDR): A region of hypervariable amino acid sequence that defines the binding affinity and specificity of an antibody. The light and heavy chains of a mammalian immunoglobulin each have three CDRs, designated L-CDR1, L-CDR2, L-CDR3 and H-CDR1, H-CDR2, H-CDR3, respectively. A single-domain antibody contains three CDRs, referred to herein as CDR1, CDR2 and CDR3.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, photon absorber, carbohydrate or recombinant virus. An antibody conjugate is often referred to as an "immunoconjugate."

When the conjugate comprises an antibody linked to a drug (such as a cytotoxic agent), the conjugate is often referred to as an "antibody-drug conjugate" or "ADC." Other antibody conjugates include, for example, multi-specific (such as bispecific or trispecific) antibodies and chimeric antigen receptors (CARs).

Conservative variant: A protein containing conservative amino acid substitutions that do not substantially affect or decrease the affinity of a protein, such as an antibody to GPC1. For example, a monoclonal antibody that specifically binds GPC1 can include at most about 1, at most about 2, at most about 5, and most about 10, or at most about 15 conservative substitutions and specifically bind the GPC1 polypeptide. The term "conservative variant" also includes the use of a substituted amino acid in place of an unsubstituted parent amino acid, provided that antibody specifically binds GPC1. Non-conservative substitutions are those that reduce an activity or binding to GPC1.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Diagnostic: Identifying the presence or nature of a pathologic condition, such as a GPC1-positive cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (such as severity) of a pathologic condition, such as mesothelioma.

Diagnostic tumor imaging: Coupling antibodies and their derivatives with positron emitting radionuclides for positron emission tomography (PET) is a process often referred to as immunoPET. While full length antibodies can be used as immunoPET agents, their biological half-life can require waiting several days prior to imaging, resulting in an increase in non-target radiation doses. Smaller, single domain antibodies have biological half-lives amenable to same day imaging.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of a chimeric molecule that is intended to have a desired effect on a cell to which the chimeric molecule is targeted. Effector molecule is also known as an effector moiety (EM), therapeutic agent, diagnostic agent, or similar terms. Therapeutic agents (or drugs) include such compounds as nucleic acids, proteins, peptides, amino acids or derivatives, glycoproteins, radioisotopes, photon absorbers, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-GPC1 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies or other therapeutic agents are known (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Endometrial cancer: A type of cancer that forms in the endometrium, the tissue lining the uterus. Most endometrial cancers are adenocarcinomas, which arise from the epithelial cells of the endometrium.

Epitope: An antigenic determinant. These are particular chemical groups or peptide sequences on a molecule that are antigenic (that elicit a specific immune response). An antibody specifically binds a particular antigenic epitope on a polypeptide, such as GPC1.

Framework region: Amino acid sequences interposed between CDRs. Framework regions of an immunoglobulin molecule include variable light and variable heavy framework regions.

Fusion protein: A protein comprising at least a portion of two different (heterologous) proteins.

Glioma: A cancer of the brain and spinal cord that begins in glial cells, which are cells that surround and support nerve cells. Gliomas are classified based on the type of glial cells that produce the tumor. Types of gliomas include astrocytoma (including glioblastoma), ependymoma and oligodendroglioma, which originate in astrocytes, ependymal cells and oligodendrocytes, respectively.

Glypican-1 (GPC1): A member of the six-member glypican family of heparan sulfate proteoglycans (HSPGs) that are attached to the cell surface by a GPI anchor (Filmus et al., *Genome Biol* 9:224, 2008). Studies have reported that GPC1 is overexpressed in certain types of cancer, such as pancreatic cancer (Kleeff et al., *J Clin Invest* 102:1662-1673, 1998), for example, pancreatic ductal adenocarcinoma (Frampton et al., *Oncotarget* 9:19006-19013, 2018; Kayed et al., *Int J Oncol* 29:1139-1148, 2006), glioma (Su et al., *Am J Pathol*

168:2014-2026, 2006), breast cancer (Matsuda et al., *Cancer Res* 61:5562-5569, 2001), ovarian cancer (Davies et al., *Clin Cancer Res* 10:5178-5186, 2004), and colorectal cancer (Li et al., *Oncotarget* 8:101189-101202, 2017). GPC1 genomic, mRNA and protein sequences are publically available (see, for example, NCBI Gene ID 2817).

GPC1-positive cancer: A cancer that expresses or overexpresses GPC1. Examples of GPC1-positive cancers include, but are not limited to, pancreatic cancer, colorectal cancer, liver cancer, glioma, lung cancer, head and neck cancer, thyroid cancer, endometrial cancer, ovarian cancer and breast cancer.

Head and neck cancer: Cancer that forms in the squamous cells that line the mucosal surfaces inside the head and neck, such as inside the mouth, nose and throat. Head and neck cancer is often referred to as squamous cell carcinoma of the head and neck Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody or functional fragment thereof. The effector molecule can be, for example, a detectable label, a photon absorber (such as IR700), or a toxin (to form an immunotoxin, such as an immunotoxin comprising *Pseudomonas* exotoxin or a variant thereof). Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. In one embodiment, an antibody is joined to an effector molecule. In another embodiment, an antibody joined to an effector molecule is further joined to a lipid or other molecule, such as to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule. The term "conjugated" or "linked" refers to making two polypeptides into one contiguous polypeptide molecule.

Immunoliposome: A liposome with antibodies or antibody fragments conjugated to its surface Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, for example other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label. The terms "conjugating," "joining," "bonding" or "linking" refer to making two polypeptides into one contiguous polypeptide molecule, or to covalently attaching a radionuclide or other molecule to a polypeptide, such as an antibody. The linkage can be either by chemical or recombinant means. "Chemical means" refers to a reaction between the antibody moiety and the effector molecule such that there is a covalent bond formed between the two molecules to form one molecule.

Liver cancer: Any type of cancer occurring in liver tissue. The most common type of liver cancer is hepatocellular carcinoma (HCC), which develops in hepatocytes. Other types of liver cancer include cholangiocarcinoma, which develops in the bile ducts; liver angiosarcoma, which is a rare form of liver cancer that begins in the blood vessels of the liver; and hepatoblastoma, which is a very rare type of liver cancer found most often in children.

Lung cancer: Any cancer that forms in the lung. Most cancers that begin in the lung are carcinomas. The two primary types of lung carcinoma are small-cell lung carcinoma (SCLC) and non-small cell lung carcinoma (NSCLC). Subclasses of NSCLC include adenocarcinoma, squamous-cell carcinoma and large-cell carcinoma.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary. Most ovarian cancers are either ovarian epithelial carcinomas (cancer that begins in the cells on the surface of the ovary) or malignant germ cell tumors (cancer that begins in egg cells). Another type of ovarian cancer is stromal cell cancer, which originates in cells that release hormones and connect the different structures of the ovaries.

Pancreatic cancer: A disease in which malignant cells are found in the tissues of the pancreas. Pancreatic tumors can be either exocrine tumors or neuroendocrine tumors, based on the cell origin of the cancer. The vast majority (~94%) of pancreatic cancers are exocrine tumors. Exocrine cancers include, for example, adenocarcinoma (the most common type of exocrine tumor), acinar cell carcinoma, intraductal papillary-mucinous neoplasm (IPMN), and mucinous cystadenocarcinoma. In some examples, the pancreatic cancer is pancreatic ductal adenocarcinoma (PDAC). Pancreatic neuroendocrine tumors, also referred to as islet cell tumors, are classified by the type of hormones they produce. Exemplary neuroendocrine tumors include gastrinoma, glucaganoma, insulinoma, somatostatinoma, VIPoma (vasoactive intestinal peptide) and nonfunctional islet cell tumor.

Pharmaceutically acceptable carriers: The pharmaceutically acceptable carriers of use are conventional. *Remington's Pharmaceutical Sciences*, by E.W. Martin, Mack Publishing Co., Easton, PA, 15th Edition, 1975, describes compositions and formulations suitable for pharmaceutical delivery of the antibodies and other compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Photoimmunotherapy: A targeted cancer therapy that utilizes an antigen-specific antibody-photoabsorber conjugate that can be activated by near-infrared light to kill targeted cells. The photon absorber is typically based on phthalocyanine dye, such as a near infrared (NIR) phthalocyanine dye (for example, IRDye® 700DX, also known as IR700). The antibody (for example, a GPC1-specific antibody) binds to the appropriate cell surface antigen (e.g. GPC1) and the photo-activatable dye induces lethal damage to cell membranes after NIR-light exposure. NIR-light exposure (690 nm) induces highly selective, necrotic cancer cell death within minutes without damage to adjoining cells (see, for example, U.S. Application No. 2018/0236076). Thus provided herein are the disclosed antibodies (e.g., HM2 and D4, or fragments thereof) conjugated to IR700.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Promoter: An array of nucleic acid control sequences which direct transcription of a nucleic acid, such as one encoding an antibody or antibody fragment provided herein. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Exemplary promoters include constitutive and activatable promoters.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein, such as an antibody or antibody fragment, is 90% free of other proteins or cellular components.

Pyrrolobenzodiazepine (PBD): A class of sequence-selective DNA minor-groove binding crosslinking agents originally discovered in *Streptomyces* species. PDBs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2): 254-293, 2012).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy. In one example, a sample includes a fine needle aspirate.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of an antibody that specifically binds a GPC1 polypeptide are typically characterized by possession of at least about 75%, for example at least about 80%, 90%, 95%, 96%, 97%, 98% or 99% sequence identity counted over the full-length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor, such as reduce a tumor size and/or volume by at least 10%, at least 20%, at least 50%, at least 75%, at least 80%, at least 90%, at least 95%, or even 100%, and/or reduce the number and/or size/volume of metastases by at least 10%, at least 20%, at least 50%, at least 75%, at least 80%, at least 90%, at least 95%, or even 100%, for example as compared to a size/volume/number prior to treatment. When administered to a subject, a dosage will generally be used that will achieve target tissue concentrations (for example, in tumors) that has been shown to achieve a desired in vitro effect.

Thyroid cancer: A type of cancer that forms in the tissues of the thyroid gland. Thyroid cancers are classified according to histopathological characteristic and include papillary thyroid cancer, follicular thyroid cancer, medullary thyroid cancer, poorly differentiated thyroid cancer, anaplastic thyroid cancer, thyroid lymphoma, squamous cell thyroid carcinoma and sarcoma of the thyroid.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. In some embodiments, the vector is a virus vector, such as a lentivirus vector or an AAV vector.

III. Monoclonal Antibodies Specific for Glypican-1 (GPC1)

Described herein are two monoclonal antibodies that bind GPC1 with high affinity. One of the monoclonal antibodies is a mouse antibody (HM2), the other is a single-domain (VHH) camel antibody (D4). It is disclosed herein that antibody D4 specifically binds both human and mouse GPC1, and both antibodies bind human GPC1 with high affinity. Chimeric antigen receptor (CAR) T cells comprised of the disclosed antibodies are capable of potently killing GPC1-positive tumor cells in vitro and in vivo. The nucleotide and amino acid sequences of HM2 and D4 are provided below. Tables 1A, 1B and 2 list the amino acid positions of CDR1, CDR2 and CDR3 of each antibody, as determined using either Kabat, IMGT, or Paratome, or a combination of all three. One of skill in the art could readily determine the CDR boundaries using an alternative numbering scheme, such as the Chothia numbering scheme.

HM2 $V_H$ DNA (SEQ ID NO: 1)

GAGGTTCAGCTGCAGCAGTCTGGGGCTGAGCTTGTGAGGCCAGGGGCCTCAGTCAAGT

TGTCCTGCACAGCTTCTGGCTTTAACATTAAAGACGACTATATGCACTGGGTGAAGCA

GAGGCCTGAACAGGGCCTGGAGTGGATTGGATGGATTGATCCTGAGAATGGTGATACT

GAATATGCCTCGAAGTTCCAGGGCAAGGCCACTATAACAGCAGACACATCCTCCAACA

CAGCCTACCTGCAGCTCAGCAGCCTGACATCTGAGGACACTGCCGTCTATTACTGTACT

CGTAGCTCCGTAGGCTACTGGGGCCAAGGCACCACTCTCACAGTCTCCTCA

HM2 $V_H$ Protein (SEQ ID NO: 2)

EVQLQQSGAELVRPGASVKLSCTASG*FNIK<u>DDYMH</u>*WVKQRPEQGLEWIGW*<u>IDPENGDT</u>* <u>EY</u>

<u>ASKFQG</u>KATITADTSSNTAYLQLSSLTSEDTAVYYC*TR<u>SSVGY</u>*WGQGTTLTVSS (Underline = Kabat CDRs; Bold = IMGT CDRs; Italics = Paratome CDRs)

HM2 $V_L$ DNA (SEQ ID NO: 3)

GATGTTGTGATGACCCAAACTCCACTCTCCCTGCCTGTCAGTCTTGGAGATCAAGCCTC

CATCTCTTGCAGATCTAGTCAGAGCCTTGTACACAGTAATGGAAACACCTATTTACATT

GGTACCTGCAGAAGCCAGGCCAGTCTCCAAAGCTCCTGATCTACAAAGTTTCCAACCG

ATTTTCTGGGGTCCCAGACAGGTTCAGTGGCAGTGGATCAGGGACTTATTTCACACTCA

AGATCAGCAGAGTGGAGGCTGAGGATCTGGGAGTTTATTTCTGCTCTCAAAGAACACA

TGTTCCGTACACGTTCGGAGGGGGGACCAAGCTGGAGATAAAA

HM2 $V_L$ Protein (SEQ ID NO: 4)

DVVMTQTPLSLPVSLGDQASISCRSSQS*<u>LVHSNGNTY</u>*<u>LH</u>WYLQKPGQSPKLLI*<u>KVS</u>* <u>NRFSG</u>

VPDRFSGSGSGTYFTLKISRVEAEDLGVYFC*<u>SQRTHVPY</u>* <u>T</u>FGGGTKLEIK (Underline = Kabat CDRs; Bold = IMGT CDRs; Italics = Paratome CDRs)

TABLE 1A

Location of CDRs in HM2 VH domain
amino acid sequence (SEQ ID NO: 2)

| Numbering Scheme | CDR1 | CDR2 | CDR3 |
|---|---|---|---|
| Kabat | 31-35 | 50-66 | 99-103 |
| IMGT | 26-33 | 51-58 | 97-103 |
| Paratome | 27-35 | 47-61 | 97-103 |
| Combined | 26-35 | 47-66 | 97-103 |

TABLE 1B

Location of CDRs in HM2 VL domain
amino acid sequence (SEQ ID NO: 4)

| Numbering Scheme | CDR1 | CDR2 | CDR3 |
|---|---|---|---|
| Kabat | 24-39 | 55-61 | 94-102 |
| IMGT | 27-37 | 55-57 | 94-101 |
| Paratome | 28-39 | 51-61 | 94-102 |
| Combined | 24-39 | 51-61 | 94-102 |

```
D4 DNA
                                                   (SEQ ID NO: 5)
CAGGTGCAGCTGGTGGAGTCTGGGGGAGGCTTGGTGCAGCCCGGGGGGTCTCTGAGAC

TCTCCTGTGTAGCCTCTGGATACAGCTACAGTATTGGTTACATGGCCTGGTTCCGCCAG

GCCCCAGGAAAGGAGCGCGCGTGGGTCGCGTCTCGATATACTGGTGACGGTGGCGCA

GTCTTTGACGACGCCGTGAAGGGCCGATTCACCACCTCCCAAGAGAGTGCCGGGAACA

CGTTCGATTTGCAAATGGACAGCCTGAAACCTGAGGACACTGCCATGTACTATTGCGC

AGCGAAAGGGCCCGGTTTCGGGCGGTGGGAGTACTGGGGCCGGGGGACCCAGGTCAC

CGTCTCCTCA

D4 Protein
                                                   (SEQ ID NO: 6)
QVQLVESGGGLVQPGGSLRLSCVASGYSYSIGYMAWFRQAPGKERAWVA_S_RYTGDGGA_VF_

_DDAVKG_RFTTSQESAGNTFDLQMDSLKPEDTAMYYCAA_KG_PGFGRWEYWGRGTQVTVS

S
(Underline = Kabat CDRs; Bold = IMGT CDRs; Italics = Paratome CDRs)
```

TABLE 2

Location of CDRs in the D4
amino acid sequence (SEQ ID NO: 6)

| Numbering Scheme | CDR1 | CDR2 | CDR3 |
|---|---|---|---|
| Kabat | 31-35 | 50-66 | 99-109 |
| IMGT | 26-33 | 51-58 | 97-108 |
| Paratome | 27-33 | 47-61 | 97-108 |
| Combined | 26-35 | 47-66 | 97-108 |

Provided herein are monoclonal antibodies that bind (for example, specifically bind) GPC1, such as cell-surface or soluble GPC1. In some example, a GPC1 monoclonal antibody has a Kd of 10 nM or less, such as 0.1 nM to 10 nM. In some embodiments, the GPC1 is human GPC1, mouse GPC1, or both human and mouse GPC1. In some embodiments, the monoclonal antibody includes a variable heavy (VH) domain and a variable light (VL) domain. In some examples, the monoclonal antibody includes at least a portion of the amino acid sequence set forth herein as SEQ ID NO: 2 and/or SEQ ID NO: 4, such as one or more (such as all three) CDR sequences from SEQ ID NO: 2 and/or SEQ ID NO: 4, as determined by any numbering scheme, such as IMGT, Kabat, Paratome or Chothia, or any combination thereof. In other embodiments, the monoclonal antibody is a single-domain antibody. In some examples, the monoclonal antibody includes at least a portion of the amino acid sequence set forth herein as SEQ ID NO: 6, such as one or more (such as all three) CDR sequences from SEQ ID NO: 6, as determined by any numbering scheme, such as IMGT, Kabat, Paratome or Chothia, or any combination thereof.

In some embodiments, the VH domain of the monoclonal antibody comprises the CDR1, CDR2 and CDR3 sequences of SEQ ID NO: 2 and/or the VL domain of the monoclonal antibody comprises the CDR1, CDR2 and CDR3 sequences of SEQ ID NO: 4. In some examples, the CDR sequences are determined using the IMGT, Kabat, Paratome or Chothia numbering scheme, or a combination thereof. In particular examples, the CDR sequences are determined using a combination of Kabat, IMGT and Paratome.

In some embodiments, the CDR1, CDR2 and CDR3 sequences of the VH domain of the monoclonal antibody comprise residues 31-35, 50-66 and 99-103 of SEQ ID NO: 2; residues 26-33, 51-58 and 97-103 of SEQ ID NO: 2; residues 27-35, 47-61 and 97-103 of SEQ ID NO: 2; or residues 26-35, 47-66 and 97-103 of SEQ ID NO: 2. In some embodiments, CDR1, CDR2 and CDR3 sequences of the VL domain of the monoclonal antibody comprise residues 24-39, 55-61 and 94-102 of SEQ ID NO: 4; residues 27-37, 55-57 and 94-101 of SEQ ID NO: 4; or residues 28-39, 51-61 and 94-102 of SEQ ID NO: 4.

In some examples, the amino acid sequence of the VH domain of the monoclonal antibody is at least 80%, at least 85%, at least 90%, at least 95%, at least 96%, at least 97%, at least 98% or at least 99% identical to SEQ ID NO: 2 and/or the amino acid sequence of the VL domain of the monoclonal antibody is at least 80%, at least 85%, at least 90%, at least 95%, at least 96%, at least 97%, at least 98% or at least 99% identical to SEQ ID NO: 4. In specific non-limiting examples, the sequence of the VH domain of the monoclonal antibody comprises or consists of SEQ ID NO: 2, and/or the sequence of the VL domain of the monoclonal antibody comprises or consists of SEQ ID NO: 4.

In some embodiments, the monoclonal antibody comprises an antigen-binding fragment selected from an Fab fragment, an Fab' fragment, an F(ab)'$_2$ fragment, a single chain variable fragment (scFv) and a disulfide stabilized variable fragment (dsFv).

In some embodiments, the monoclonal antibody is an IgG, such as IgG1.

In some embodiments, the monoclonal antibody is a mouse antibody. In other embodiments, the monoclonal antibody is a humanized antibody. In yet other embodiments, the monoclonal antibody is a chimeric antibody.

In some embodiments, the single-domain monoclonal antibody comprises the CDR1, CDR2 and CDR3 sequences of SEQ ID NO: 6. In some examples, the CDR sequences are determined using the IMGT, Kabat, Paratome or Chothia numbering scheme, or a combination thereof. In particular examples, the CDR sequences are determined using a combination of Kabat, IMGT and Paratome.

In some embodiments, the CDR1, CDR2 and CDR3 sequences of the single-domain monoclonal antibody comprise residues 31-35, 50-66 and 99-109 of SEQ ID NO: 6; residues 26-33, 51-58 and 97-108 of SEQ ID NO: 6; residues 27-33, 47-61 and 97-108 of SEQ ID NO: 6; or residues 26-35, 47-66 and 97-108 of SEQ ID NO: 6. In some examples, the amino acid sequence of the monoclonal antibody is at least 80%, at least 85%, at least 90%, at least 95%, at least 96%, at least 97%, at least 98% or at least 99% identical to SEQ ID NO: 6. In specific non-limiting examples, the sequence of the monoclonal antibody comprises of consists of SEQ ID NO: 6.

In some embodiments, the monoclonal antibody is a camel antibody. In other embodiments, the monoclonal antibody is a humanized antibody. In other embodiments, the monoclonal antibody is a chimeric antibody.

Also provided herein are chimeric antigen receptors (CARs) that include a monoclonal antibody disclosed herein (for example a single-domain antibody or a scFv). In some embodiments, the CAR further includes a hinge region, a transmembrane domain, a costimulatory signaling moiety, a signaling domain, or any combination thereof. In specific non-limiting examples, the hinge region comprises a CD8α hinge region, the transmembrane domain comprises a CD8α transmembrane domain, the costimulatory signaling moiety comprises a 4-1BB signaling moiety and/or the signaling domain comprises a CD3ζ signaling domain.

Also provided herein are GPC1-specific monoclonal antibodies modified to enable their use with a universal CAR system. In some embodiments, the GPC1-specific monoclonal antibody is fused to one component of a specific binding pair. In some examples, the monoclonal antibody is fused to a leucine zipper or biotin.

Further provided are cells expressing a GPC1-specific CAR. In some examples, the cell is a T lymphocyte, such as a CTL. CARs and CAR-expressing T cells are further described in section IV.

Also provided herein are immunoconjugates that include a monoclonal antibody disclosed herein and an effector molecule. In some instances, the immunoconjugate includes an antibody dimer (such as two D4 VHH). In some embodiments, the effector molecule is a toxin, such as, but not limited to, *Pseudomonas* exotoxin or a variant thereof, such as PE38 or PE-LR. In some examples, the PE is PE-LR having the amino acid sequence of residues 121-363 of SEQ ID NO: 15. In particular non-limiting embodiments, the amino acid sequence of the immunoconjugate is at least 80%, at least 85%, at least 90%, at least 95%, at least 96%, at least 97%, at least 98% or at least 99% identical to SEQ ID NO: 15, SEQ ID NO: 17, SEQ ID NO: 19 or SEQ ID NO: 21. In specific examples, the amino acid sequence of the immunotoxin comprises or consists of SEQ ID NO: 15, SEQ ID NO: 17, SEQ ID NO: 19 or SEQ ID NO: 21. In other embodiments, the effector molecule is a detectable label, such as, but not limited to, a fluorophore, an enzyme or a radioisotope. In other embodiments, the effector molecule is a photon absorber, such as IR700. Immunoconjugates comprising a photon absorber can be used for photoimmunotherapy. Immunoconjugates are further described in section V.

Further provided herein are antibody-drug conjugates (ADCs) that include a drug conjugated to a monoclonal antibody disclosed herein. In some embodiments, the drug is a small molecule, for example an anti-microtubule agent, an anti-mitotic agent and/or a cytotoxic agent. ADCs are further described in section VI.

Also provided herein are multi-specific antibodies that include a monoclonal antibody disclosed herein and at least one additional monoclonal antibody or antigen-binding fragment thereof. In some embodiments, the multi-specific antibody is a bispecific antibody. In other embodiments, the multi-specific antibody is a trispecific antibody. In some embodiments, the at least one additional monoclonal antibody or antigen binding fragment thereof specifically binds a component of the T cell receptor or a natural killer (NK) cell activating receptor. Multi-specific antibodies are further described in section VII.

Further provided herein are antibody-nanoparticle conjugates that include a nanoparticle conjugated to a monoclonal antibody disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section VIII.

Also provided herein are fusion proteins that include a monoclonal antibody disclosed herein and a heterologous protein or peptide. In some embodiments, the heterologous protein is an Fc protein. In some examples, the Fc protein is a mouse Fc or a human Fc protein.

Also provided are nucleic acid molecules encoding a monoclonal antibody disclosed herein. In some embodiments, the nucleic acid molecule is at least 80%, at least 85%, at least 90%, at least 95%, at least 96%, at least 97%, at least 98% or at least 99% identical to SEQ ID NO: 1, SEQ ID NO: 3, or SEQ ID NO: 5. In some examples, the nucleic acid molecule comprises of consists of the nucleotide sequence SEQ ID NO: 1, or a degenerate variant thereof; the nucleotide sequence of SEQ ID NO: 3, or a degenerate variant thereof; the nucleotide sequences of SEQ ID NO: 1 and SEQ ID NO: 3, or degenerate variants thereof; or the nucleotide sequence of SEQ ID NO: 5, or a degenerate variant thereof. Further provided are nucleic acid molecules encoding a CAR, immunoconjugate, multi-specific antibody, or fusion protein disclosed herein. In some examples, the immunoconjugate comprises PE-LR, and the nucleic acid sequence encoding LR comprises nucleotides 361-1089 of SEQ ID NO: 14. In particular examples, the nucleic acid molecule encodes an immunotoxin and the nucleic acid sequence of the immunotoxin is at least 80%, at least 85%, at least 90%, at least 95%, at least 96%, at least 97%, at least 98% or at least 99% identical to SEQ ID NO: 14, SEQ ID NO: 16, SEQ ID NO: 18 or SEQ ID NO: 20. In specific examples, the nucleic acid sequence of the immunotoxin comprises or consists of SEQ ID NO: 14, SEQ ID NO: 16, SEQ ID NO: 18 or SEQ ID NO: 20, or a degenerate variant thereof. In some embodiments, the nucleic acid molecule is operably linked to a promoter. Vectors that include the nucleic acid molecules are further provided herein.

Further provided herein is a nucleic acid construct that expresses a CAR and a truncated human EGFR (huEGFRt). In some embodiments, the nucleic acid comprises in the 5' to 3' direction: a nucleic acid encoding a first granulocyte-macrophage colony stimulating factor receptor signal sequence (GMCSFRss); a nucleic acid encoding a GPC1-specific monoclonal antibody disclosed herein; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second GMCSFRss; and a nucleic acid encoding a truncated human epidermal growth factor receptor (huEGFRt). In some examples, the nucleic acid further includes a human elongation factor 1α (EF1α) promoter sequence 5' of the nucleic acid encoding the first GMCSFRss. In some examples, the hinge region comprises a CD8α hinge region. In some examples, the transmembrane domain comprises a CD8α transmembrane domain. In some examples, the costimulatory signaling moiety comprises a 4-1BB signaling moiety. In some examples, the signaling domain comprises a CD3ζ signaling domain. In some examples, the amino acid sequence of the GPC1-specific monoclonal antibody comprises SEQ ID NO: 2 and SEQ ID NO: 4. In other examples, the amino acid sequence of the GPC1-specific monoclonal antibody comprises SEQ ID NO: 6. Vectors comprising the nucleic acid constructs are also provided. In some embodiments, the vector is a lentiviral vector.

Also provided is an isolated cell co-expressing a GPC1-specific CAR disclosed herein and huEGFRt. In some examples, the cell is a cytotoxic T lymphocyte (CTL).

Compositions that include a pharmaceutically acceptable carrier and a monoclonal antibody, CAR, isolated cell (such as a CAR expressing cell, for example a CAR T cell or a CAR NK cell), immunoconjugate, ADC, multi-specific antibody, antibody-nanoparticle conjugate, or fusion protein disclosed herein are further provided by the present disclosure. Compositions and their use are further described in section IX.

IV. Chimeric Antigen Receptors (CARs)

The disclosed monoclonal antibodies can also be used to produce CARs (also known as chimeric T cell receptors, artificial T cell receptors or chimeric immunoreceptors) and/or cytotoxic T lymphocytes (CTLs) or natural killer (NK) cells engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010; Dai et al., *J Natl Cancer Inst* 108(7):djv439, 2016). In many instances, the binding moiety is an antigen binding fragment of a monoclonal antibody, such as a scFv, or a single-domain antibody. The spacer/hinge region typically includes sequences from IgG subclasses, such as IgG1, IgG4, IgD and CD8 domains. The transmembrane domain can be derived from a variety of different T cell proteins, such as CD3ζ, CD4, CD8 or CD28. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28, 4-1BB (CD137, TNFRSF9), OX-40 (CD134), ICOS, CD27 and/or DAP10.

CTLs, NK cells (or other immune cells) expressing CARs can be used to target a specific cell type, such as a GPC1-positive tumor cell. Thus, the monoclonal antibodies disclosed herein can be used to engineer CTLs or NK cells that express a CAR containing the GPC1-specific monoclonal antibody, thereby targeting the engineered CTLs or NK cells to GPC1-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Multispecific (such as bispecific) or bicistronic CARs are also contemplated by the present disclosure. In some embodiments, the multispecific or bispecific CAR includes a monoclonal antibody (or antigen-binding fragment thereof) specific for GPC1 (such as HM2 or D4) and a monoclonal antibody specific for a different antigen, such as a T cell antigen. Similarly, a bicistronic CAR includes two CAR molecules expressed from the same construct where one CAR molecule is a GPC1-targeted CAR and the second CAR targets a second antigen. See, for example, Qin et al., *Blood* 130:810, 2017; and WO/2018/213337.

Accordingly, provided herein are CARs that include a GPC1-specific antibody, such as a single-domain antibody or a scFv. Also provided are isolated nucleic acid molecules and vectors encoding the CARs (including bispecific and bicistronic CARs), and host cells, such as CTLs or NK cells, expressing the CARs, bispecific CAR or bicistronic CARs. CTLs or NK cells expressing CARs comprised of a GPC1-specific monoclonal antibody can be used for the treatment of cancers that express GPC1. In some embodiments herein, the CAR is a bispecific CAR. In other embodiments herein, the CAR is a bicistronic CAR.

In some embodiments, the CAR includes a signal peptide sequence, for example, N-terminal to the antigen binding domain. The signal peptide sequence can be any suitable signal peptide sequence, such as a signal sequence from granulocyte-macrophage colony-stimulating factor receptor (GMCSFR), immunoglobulin light chain kappa, or IL-2. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

In some embodiments, the CARs disclosed herein are expressed from a construct (such as from a lentivirus vector) that also expresses a truncated version of human EGFR (huEGFRt). The CAR and huEGFRt are separated by a self-cleaving peptide sequence (such as T2A) such that upon expression in a transduced cell, the CAR is cleaved from huEGFRt.

In some embodiments disclosed herein, the CAR constructs encode the following amino acid sequences, in the N-terminal to C-terminal direction:

GMCSFRss:
(SEQ ID NO: 7)
MLLLVTSLLLCELPHPAFLLIP

NdeI:
HM

Antigen-binding:
a GPC 1-specific antibody (such as HM2 or D4)

SpeI:
TS

CD8α hinge:
(SEQ ID NO: 8)
TTTPAPRPPTPAPTIASQPLSLRPEACRPAAGGAVHTRGLDFACD

CD8α TM:
(SEQ ID NO: 9)
IYIWAPLAGTCGVLLLSLVIT 4-1BB:
(SEQ ID NO: 10)
KRGRKKLLYIFKQPFMRPVQTTQEEDGCSCRFPEEEEGGCEL

CD3ζ:
(SEQ ID NO: 11)
RVKFSRSADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR

T2A:
(SEQ ID NO: 12)
EGRGSLLTCGDVEENPGP

GMCSFRss:
(SEQ ID NO: 7)
MLLLVTSLLLCELPHPAFLLIP huEGFRt:
(SEQ ID NO: 13)
RKVCNGIGIGEFKDSLSINATNIKHFKNCTSISGDLHILPVAFRGDSFTHTPPLDPQELDILKT

VKEITGFLLIQAWPENRTDLHAFENLEIIRGRTKQHGQFSLAVVSLNITSLGLRSLKEISDGD

VIISGNKNLCYANTINWKKLFGTSGQKTKIISNRGENSCKATGQVCHALCSPEGCWGPEPR

DCVSCRNVSRGRECVDKCNLLEGEPREFVENSECIQCHPECLPQAMNITCTGRGPDNCIQC

AHYIDGPHCVKTCPAGVMGENNTLVWKYADAGHVCHLCHPNCTYGCTGPGLEGCPTNG

PKIPSIATGMVGALLLLLVVALGIGLFM

The human epidermal growth factor receptor is comprised of four extracellular domains, a transmembrane domain and three intracellular domains. The EGFR domains are found in the following N-terminal to C-terminal order: Domain I-Domain II-Domain III-Domain IV-transmembrane (TM) domain-juxtamembrane domain-tyrosine kinase domain-C-terminal tail. Domain I and Domain III are leucine-rich domains that participate in ligand binding. Domain II and Domain IV are cysteine-rich domains and do not make contact with EGFR ligands. Domain II mediates formation of homo- or hetero-dimers with analogous domains from other EGFR family members, and Domain IV can form disulfide bonds with Domain II. The EGFR TM domain makes a single pass through the cell membrane and may play a role in protein dimerization. The intracellular domain includes the juxtamembrane domain, tyrosine kinase domain and C-terminal tail, which mediate EGFR signal transduction (Wee and Wang, Cancers 9(52), doi:10.3390/cancers9050052; Ferguson, *Annu Rev Biophys* 37:353-373, 2008; Wang et al., *Blood* 118(5):1255-1263, 2011).

A truncated version of human EGFR, referred to herein as "huEGFRt" includes only Domain III, Domain IV and the TM domain. Thus, huEGFRt lacks Domain I, Domain II, and all three intracellular domains. huEGFRt is not capable of binding EGF and lacks signaling activity. However, this molecule retains the capacity to bind particular EGFR-specific monoclonal antibodies, such as FDA-approved cetuximab (PCT Publication No. WO 2011/056894, which is herein incorporated by reference).

Transduction of T cells (or NK cells) with a construct (such as a lentivirus vector) encoding both huEGFRt and a tumor antigen-specific CAR disclosed herein allows for selection of transduced T cells using labelled EGFR monoclonal antibody cetuximab (ERBITUX™). For example, cetuximab can be labeled with biotin, and transduced T cells can be selected using anti-biotin magnetic beads, which are commercially available (such as from Miltenyi Biotec). Co-expression of huEGFRt also allows for in vivo tracking of adoptively transferred CAR-expressing T cells (or NK cells). Furthermore, binding of cetuximab to T cells expressing huEGFRt induces cytotoxicity of ADCC effector cells, thereby providing a mechanism to eliminate transduced T cells in vivo (Wang et al., *Blood* 118(5):1255-1263, 2011), such as at the conclusion of therapy.

Also provided herein are GPC1-specific monoclonal antibodies modified to enable their use with a universal CAR system. Universal CAR systems have been developed in order to increase CAR flexibility and expand their use to additional antigens. Currently, for each patient who receives CAR T cell therapy, autologous T cells must be cultured, expanded, and modified to express an antigen-specific CAR. This process is lengthy and expensive, limiting its use. Universal CARs are based on a system in which the signaling components of the CAR are split from the antigen-binding portion of the molecule, but come together using a "lock-key" system. For example, biotin-binding immune receptor (BBIR) CARs are comprised of an intracellular T cell signaling domain fused to an extracellular domain comprising avidin. Biotinylated antigen-specific (such as GPC1-specific) monoclonal antibodies can then bind the BBIR to direct T cells to tumor antigen-expressing cells. Another example is the split, universal and programmable (SUPRA) CAR system. In the SUPRA system, the CAR includes the intracellular signaling domains fused to an extracellular leucine zipper, which is paired with an antigen-specific monoclonal antibody fused to a cognate leucine zipper. For a review of universal CAR systems, see, for example, Zhao et al., *J Hematol Oncol* 11(1):132, 2018; and Cho et al., *Cell* 173:1426-1438, 2018. In some embodiments herein, the GPC1-specific monoclonal antibody is fused to one component of a specific binding pair. In some examples, the monoclonal antibody is fused to a leucine zipper or biotin.

Another type of universal CAR can be generated using a sortase enzyme. A sortase is a prokaryotic enzyme that modifies surface proteins by recognizing and cleaving a carboxyl-terminal sorting signal. Sortase catalyzes transpeptidation between a sortase recognition motif and a sortase acceptor motif. Thus, antigen-specific CARs can be generated by contacting an antigen-specific antibody fused to a sortase recognition motif with a portion of a CAR molecule that includes the intracellular signaling domain(s), a transmembrane region and an extracellular portion comprising a sortase acceptor motif. In the presence of the sortase enzyme, the two components become covalently attached to form a complete antigen-specific CAR. Accordingly, in some embodiments herein, a GPC1-specific monoclonal antibody is modified to include a sortase recognition motif (see, for example, PCT Publication No. WO 2016/014553).

V. Immunoconjugates

The disclosed monoclonal antibodies can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}$I, $^{32}$P, $^{14}$C, $^{3}$H and $^{35}$S, photon absorbers such as IR700, and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response (such as for use in detection), the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine ($-NH_2$) or sulfhydryl ($-SH$) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well-known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a photon absorber, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

An antibody disclosed herein can also be conjugated to a photon absorber. In some embodiments, the photon absorber is a phthalocyanine dye, such as, but not limited to, IRDye® 700DX (also known as "IR700"). Antibody-photoabsorber conjugates can be used for photoimmunotherapy.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, MO). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/

031741, WO 2009/32954, WO 2011/32022, WO 2012/154530, and WO 2012/170617.

In some embodiments herein, the immunoconjugate comprises the D4 of HM2 antibody and PE-LR. In some examples, a dimer of D4 is present in the immunoconjugate. In particular non-limiting embodiments, the amino acid sequence of the immunoconjugate is at least 80%, at least 85%, at least 90%, at least 95%, at least 96%, at least 97%, at least 98% or at least 99% identical to SEQ ID NO: 15, SEQ ID NO: 17, SEQ ID NO: 19 or SEQ ID NO: 21. In specific examples, the amino acid sequence of the immunotoxin comprises or consists of SEQ ID NO: 15, SEQ ID NO: 17, SEQ ID NO: 19 or SEQ ID NO: 21.

The antibodies described herein can also be used to target any number of different diagnostic or therapeutic compounds to cells expressing the tumor antigen on their surface. Thus, an antibody of the present disclosure can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, photon absorbers, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Antibody-Drug Conjugates (ADCs)

ADCs are compounds comprised of a tumor antigen-specific antibody (such as a single-domain antibody or antigen-binding fragment of an immunoglobulin) and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) GPC1. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, *vinca* alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am*

*Chem Soc*, 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256, 746; 4,260,608; 4,265,814; 4,294,757; 4,307,016; 4,308, 268; 4,308,269; 4,309,428; 4,313,946; 4,315,929; 4,317, 821; 4,322,348; 4,331,598; 4,361,650; 4,364,866; 4,424, 219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663, 149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a GPC1-positive cancer alone or in combination with another therapeutic agent and/or in combination with any standard therapy for the treatment of cancer (such as surgical resection of the tumor, chemotherapy or radiation therapy).

VII. Multi-Specific Antibodies

Multi-specific antibodies are recombinant proteins comprised of two or more monoclonal antibodies (such as single-domain antibodies) or antigen-binding fragments of two or more different monoclonal antibodies. For example, bispecific antibodies are comprised of antigen-binding fragments of two different monoclonal antibodies. Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The GPC1-specific monoclonal antibodies disclosed herein can be used to generate multi-specific (such as bispecific or trispecific) antibodies that target both GPC1 and CTLs, or target both GPC1 and NK cells, thereby providing a means to treat GPC1-expressing cancers. In one example, the GPC1-specific monoclonal antibodies disclosed herein are used to generate multi-specific (such as bispecific or trispecific) antibodies that target both GPC1 and PD1, PDL1, EGFR, or VEGF, thereby providing a means to treat GPC1-expressing cancers.

Bi-specific T-cell engagers (BiTEs) are a type of bispecific monoclonal antibody that are fusions of a first monoclonal antibody (such as a scFv or a single-domain antibody) that targets a tumor antigen (such as GPC1) and a second antibody that binds T cells, such as CD3 on T cells. In some embodiments herein, one of the binding moieties of the BiTE is specific for GPC1.

Bi-specific killer cell engagers (BiKEs) are a type of bispecific monoclonal antibody that are fusions of a first monoclonal antibody (such as a scFv or single-domain antibody) that targets a tumor antigen (such as GPC1) and a second scFv that binds a NK cell activating receptor, such as CD16.

Provided herein are multi-specific, such as trispecific or bispecific, monoclonal antibodies comprising a GPC1-specific monoclonal antibody. In some embodiments, the multi-specific monoclonal antibody further comprises a monoclonal antibody that specifically binds a component of the T cell receptor, such as CD3. In other embodiments, the multi-specific monoclonal antibody further comprises a monoclonal antibody that specifically binds a NK cell activating receptor, such as CD16, Ly49, or CD94. Also provided are isolated nucleic acid molecules and vectors encoding the multi-specific antibodies, and host cells comprising the nucleic acid molecules or vectors. Multi-specific antibodies comprising a GPC1-specific antibody can be used for the treatment of cancers that express GPC1. Thus, provided herein are methods of treating a subject with cancer by selecting a subject with a cancer that expresses GPC1, and administering to the subject a therapeutically effective amount of the GPC1-targeting multi-specific antibody.

VIII. Antibody-Nanoparticle Conjugates

The monoclonal antibodies disclosed herein can be conjugated to a variety of different types of nanoparticles to deliver cytotoxic agents or other anti-cancer agents directly to tumor cells via binding of the antibody to GPC1 expressed on the surface of tumor cells. The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, Immunotherapy 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, Curr Med Chem 19(31)5239-5277, 2012; Immordino et al., Int J Nanomedicine 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine Niosomes range from small, unilamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly (glycolic acids) (PGA), and poly(D,L-lactic-co-glycolic acid) (PLGA).

Antibodies (or fragments thereof) can be conjugated to a suitable nanoparticle according to standard methods known in the art. For example, conjugation can be either covalent or noncovalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31) 5239-5277, 2012).

IX. Compositions and Methods of Use

Compositions are provided that include one or more of the disclosed monoclonal antibodies that bind (for example specifically bind) GPC1 in a carrier. Compositions comprising ADCs, CARs (and CTLs comprising CARs), multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, ADC, CAR, CTL, multi-specific antibody, antibody-nanoparticle conjugate, immunoliposome or immunoconjugate can be formulated for systemic or local (such as intra-tumor) administration. In one example, the antibody is formulated for parenteral administration, such as intravenous administration.

The compositions for administration can include a solution of the antibody, ADC, CAR, CTL, multi-specific (such as bispecific or trispecific) antibody, antibody-nanoparticle conjugate, immunoliposome or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, PA (1995).

The monoclonal antibodies disclosed herein can also be administered by other routes, including via inhalation, oral, topical or intraocular. In some examples, the monoclonal antibody (or conjugate thereof) is administered via fine-needle.

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight, such as 1 to 10 mg/kg or 1 to 5 mg/kg. Considerable experience is available in the art in the administration of antibody drugs, which have been marketed in the U.S. since the approval of RITUXAN™ in 1997. Antibodies, ADCs, CARs, multi-specific (such as bispecific or trispecific) antibodies, antibody-nanoparticle conjugates, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 3 to 5 mg/kg may be infused over a period of some 90 minutes, followed by weekly maintenance doses for 4-8 weeks of 1 to 2 mg/kg infused over a 30-minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions, CARs (and CTLs expressing CARs), ADCs, multi-specific (such as bispecific or trispecific) antibodies, antibody-nanoparticle conjugates, immunoliposomes and immunoconjugates disclosed herein can be administered to slow or inhibit the growth of tumor cells or inhibit the metastasis of tumor cells, such as GPC1-positive cancers. In these applications, a therapeutically effective amount of a composition is administered to a subject in an amount sufficient to inhibit growth, replication or metastasis of cancer cells, or to inhibit a sign or a symptom of the cancer. Suitable subjects may include those diagnosed with a cancer that expresses GPC1, such as, but not limited to pancreatic cancer, colorectal cancer, liver cancer, glioma, lung cancer, head and neck cancer, thyroid cancer, endometrial cancer, breast cancer or ovarian cancer. In some examples, the method reduces the volume of a tumor (such as a metastasis) by at least 10%, at least 20%, at least 50%, at least 75%, at least 80%, at least 90%, at least 95%, or even 100%, for example as compared to a volume prior to treatment. In some examples, the method reduces the number of tumor cells of a tumor by at least 10%, at least 20%, at least 50%, at least 75%, at least 80%, at least 90%, at least 95%, or even 100%, for example as compared to the number prior to treatment, In some examples, the method reduces the size of a tumor (such as a metastasis) by at least 10%, at least 20%, at least 50%, at least 75%, at least 80%, at least 90%, at least 95%, or even 100%, for example as compared to a size prior to treatment, In some examples, the method reduces the number of metastases at least 10%, at least 20%, at least 50%, at least 75%, at least 80%, at least 90%, at least 95%, or even 100%, for example as compared to a number prior to treatment. In some examples, the method increases the prognosis of a subject, such as increases the lifespan of the subject by at least 4 months, at least 6 months, at least 8 months, at least 9 months, at least 12 months, at least 24 months, at least 36 months, or at least 60 months, for example as compared to a number prior to treatment, In some examples, combinations of these effects are achieved.

Provided herein is a method of treating a GPC1-positive cancer in a subject by administering to the subject a therapeutically effective amount of a GPC1-specific antibody, immunoconjugate, CAR (or CTLs expressing a CAR), ADC, multi-specific (such as bispecific or trispecific) antibody, antibody-nanoparticle conjugate, immunoliposome or composition disclosed herein. Also provided herein is a method of inhibiting tumor growth or metastasis of a GPC1-positive cancer in a subject by administering to the subject a therapeutically effective amount of a GPC1-specific antibody, immunoconjugate, CAR (such as a CTL expressing a CAR), ADC, multi-specific (such as bispecific or trispecific) antibody, antibody-nanoparticle conjugate, immunoliposome or composition disclosed herein. In some embodiments, the GPC1-positive cancer is a pancreatic cancer, colorectal cancer, liver cancer, glioma, lung cancer, head and neck cancer, thyroid cancer, endometrial cancer, breast cancer or ovarian cancer.

A therapeutically effective amount of a GPC1-specific monoclonal antibody, ADC, CAR (for example a CTL expressing a CAR), multi-specific (such as bispecific or trispecific) antibody, immunoconjugate, immunoliposome or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the GPC1-specific antibodies, ADCs, CARs, immunoconjugates, multi-specific antibodies, antibody-nanoparticle conjugates, immunoliposomes and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells (such as anti-PD1, anti-PDL1, anti-VEGF, and anti-EGFR antibodies).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting GPC1 protein in vitro or in vivo. For example, the disclosed monoclonal antibodies can be used for in vivo tumor imaging. To use the disclosed antibodies as diagnostic reagents in vivo, the antibodies are labelled with a detectable moiety, such as a radioisotope, fluorescent label or positron emitting radionuclides. As one example, the monoclonal antibodies disclosed herein can be conjugated to a positron emitting radionuclide for use in positron emission tomography (PET); this diagnostic process is often referred to as immunoPET. While full length antibodies can make good immunoPET agents, their biological half-life can require waiting several days prior to imaging, which increases associated non-target radiation doses. Smaller, single domain antibodies/nanobodies have biological half-lives amenable to same day imaging.

In other instances, GPC1 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. In some examples, the sample is a serum sample containing exosomes. A biological sample is typically obtained from a mammal, such as a human or non-human primate.

Exosomes are lipid bilayer-enclosed extracellular vesicles containing proteins and nucleic acids that are secreted by all cells and circulate in the blood. It has been demonstrated that patients with pancreatic cancer have GPC1-positive, cancer-derived exosomes circulating in their blood (Melo et al., *Nature* 523(7559):177-182, 2015). Thus, detection of GPC1-positive exosomes in serum can be used as a means to diagnose a subject as having a GPC1-positive cancer, such as pancreatic cancer. Accordingly, provided herein is a method of diagnosing a subject as having a GPC1-positive cancer (such as pancreatic cancer) by contacting a serum sample from the subject with a GPC1-specific monoclonal antibody disclosed herein; and detecting binding of the antibody to exosomes in the sample. In some examples, exosomes are isolated from the serum sample prior to being contacted with the GPC1-specific antibody. Detection of GPC1-expressing exosomes can be performed using any appropriate assay, such as by flow cytometry using a GPC1-specific antibody disclosed herein.

Provided herein is a method of determining if a subject has a GPC1-positive cancer by contacting a sample from the subject with a GPC1-specific monoclonal antibody disclosed herein; and detecting binding of the antibody to the sample. An increase in binding of the antibody to the sample as compared to binding of the antibody to a control sample identifies the subject as having a GPC1-positive cancer.

In another embodiment, provided is a method of confirming a diagnosis of a GPC1-positive cancer in a subject by contacting a sample from a subject diagnosed with a GPC1-positive cancer with a GPC1-specific monoclonal antibody disclosed herein; and detecting binding of the antibody to the sample. An increase in binding of the antibody to the sample as compared to binding of the antibody to a control sample confirms the diagnosis of a GPC1-positive cancer in the subject.

In some examples of the disclosed methods, the monoclonal antibody is directly labeled.

In other examples, the methods further include contacting a second antibody (a detection antibody) that specifically binds the monoclonal antibody with the sample; and detecting the binding of the second antibody. An increase in binding of the second antibody to the sample as compared to binding of the second antibody to a control sample detects a GPC1-positive cancer in the subject or confirms the diagnosis of a GPC1-positive cancer in the subject.

In some cases, the cancer is pancreatic cancer, colorectal cancer, liver cancer, glioma, lung cancer, head and neck cancer, thyroid cancer, endometrial cancer, breast cancer or ovarian cancer.

In some examples, the control sample is a sample from a subject without cancer. In particular examples, the sample is a blood or tissue sample.

In some embodiments of the methods of diagnosis and detection, the antibody that binds (for example specifically binds) GPC1 is directly labeled with a detectable label. In another embodiment, the antibody that binds (for example, specifically binds) GPC1 (the first antibody) is unlabeled and a second antibody or other molecule that can bind the antibody that specifically binds GPC1 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative embodiment, GPC1 can be assayed in a biological sample by a competition immunoassay utilizing GPC1 protein standards labeled with a detectable substance and an unlabeled antibody that specifically binds GPC1. In this assay, the biological sample, the labeled GPC1 protein standards and the antibody that specifically bind GPC1 are combined and the amount of labeled GPC1 protein standard bound to the unlabeled antibody is determined. The amount of GPC1 in the biological sample is inversely proportional to the amount of labeled GPC1 protein standard bound to the antibody that specifically binds GPC1.

The immunoassays and methods disclosed herein can be used for a number of purposes. In one embodiment, the antibody that specifically binds may be used to detect the production of GPC1 in cells in cell culture. In another embodiment, the antibody can be used to detect the amount of GPC1 in a biological sample, such as a tissue sample, or a blood or serum sample. In some examples, the GPC1 is cell-surface GPC1. In other examples, the GPC1 protein is soluble (for example, in a cell culture supernatant or in a body fluid sample, such as a blood or serum sample).

In one embodiment, a kit is provided for detecting GPC1 in a biological sample, such as a blood sample or tissue sample. For example, to confirm a cancer diagnosis in a subject, a biopsy can be performed to obtain a tissue sample for histological examination. Kits for detecting GPC1 will typically comprise a monoclonal antibody that specifically binds GPC1, such as any of the monoclonal antibodies disclosed herein, and can further include a labeled secondary antibody that can specifically bind to the anti-GPC1 antibody. In a specific embodiment, the anti-GPC1 antibody in the kit itself is labeled (for example, with a fluorescent, radioactive, or an enzymatic label).

In one embodiment, a kit includes instructional materials disclosing means of use of an antibody that binds GPC1. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method.

In one embodiment, the diagnostic kit comprises an immunoassay. Although the details of the immunoassays may vary with the particular format employed, the method of detecting GPC1 in a biological sample generally includes the steps of contacting the biological sample with an antibody which specifically reacts, under immunologically reactive conditions, to GPC1. The antibody is allowed to specifically bind under immunologically reactive conditions to form an immune complex, and the presence of the immune complex (bound antibody) is detected directly or indirectly.

The antibodies disclosed herein can also be utilized in immunoassays, such as, but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind GPC1, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Isolation and Characterization of GPC1-Specific Monoclonal Antibodies This example describes two GPC1-specific monoclonal antibodies that were isolated from a phage display library and mouse hybridomas. Mouse monoclonal antibody HM2 (SEQ ID NO: 2 and SEQ ID NO: 4) binds the C-lobe of GPC1 close to the cell surface, and the camel single-domain antibody D4 (SEQ ID NO: 6) recognizes a conformational epitope in the protein core of GPC1.

Figure 1B:
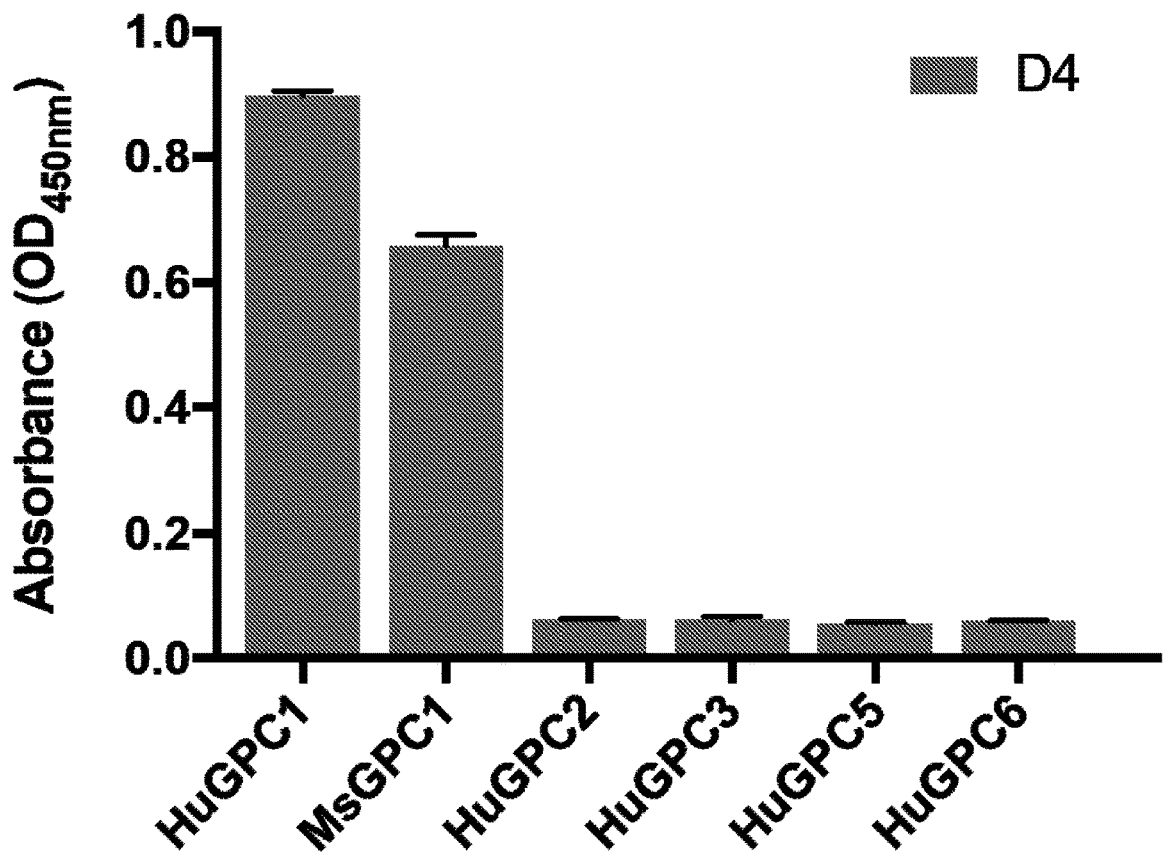
Figure 2:
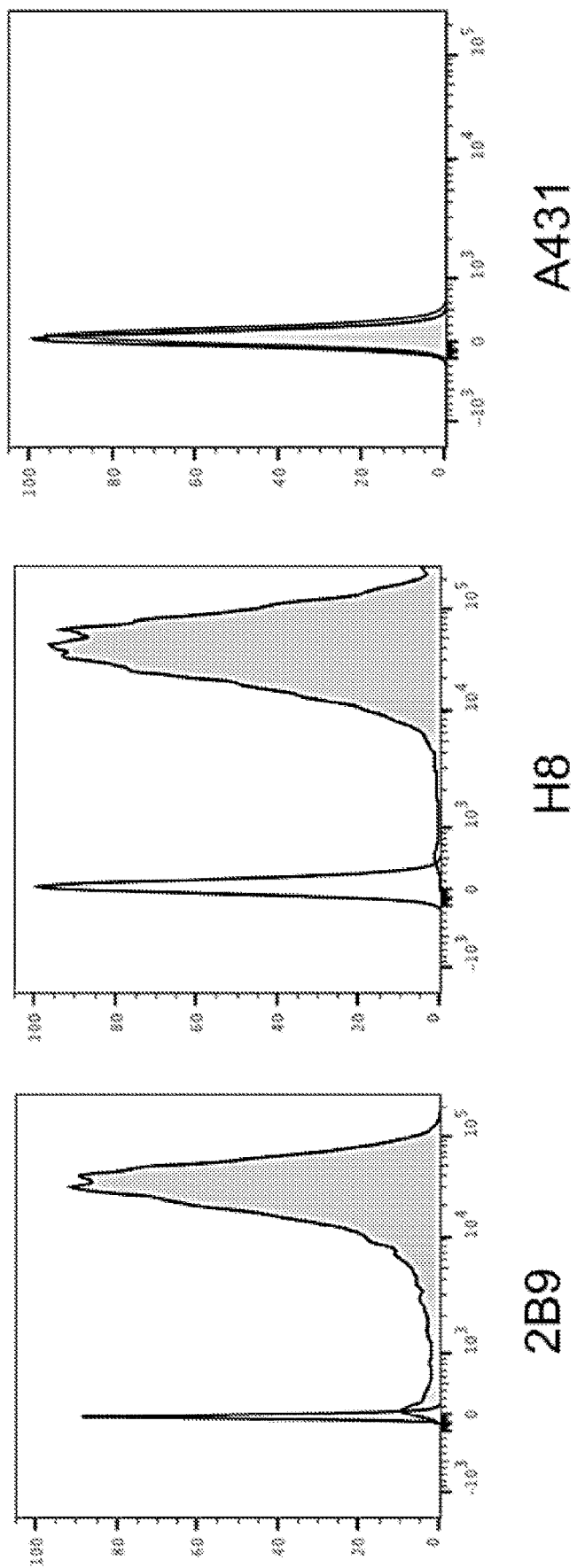
FIG. 2: Flow cytometry analysis of cell-surface GPC1 expression using the D4 antibody. Binding of D4 to GPC1-overexpressing 2B9 KLM pancreatic cancer cells, GPC1-overexpressing H8 epidermoid carcinoma cells, and GPC1-negative A431 cells was evaluated. White peaks represent cell-surface staining with an isotype control antibody, and shaded peaks represent cell-surface staining with the GPC1-specific D4 antibody. D4 was used at a concentration of 5 µg/ml.
Figure 3:
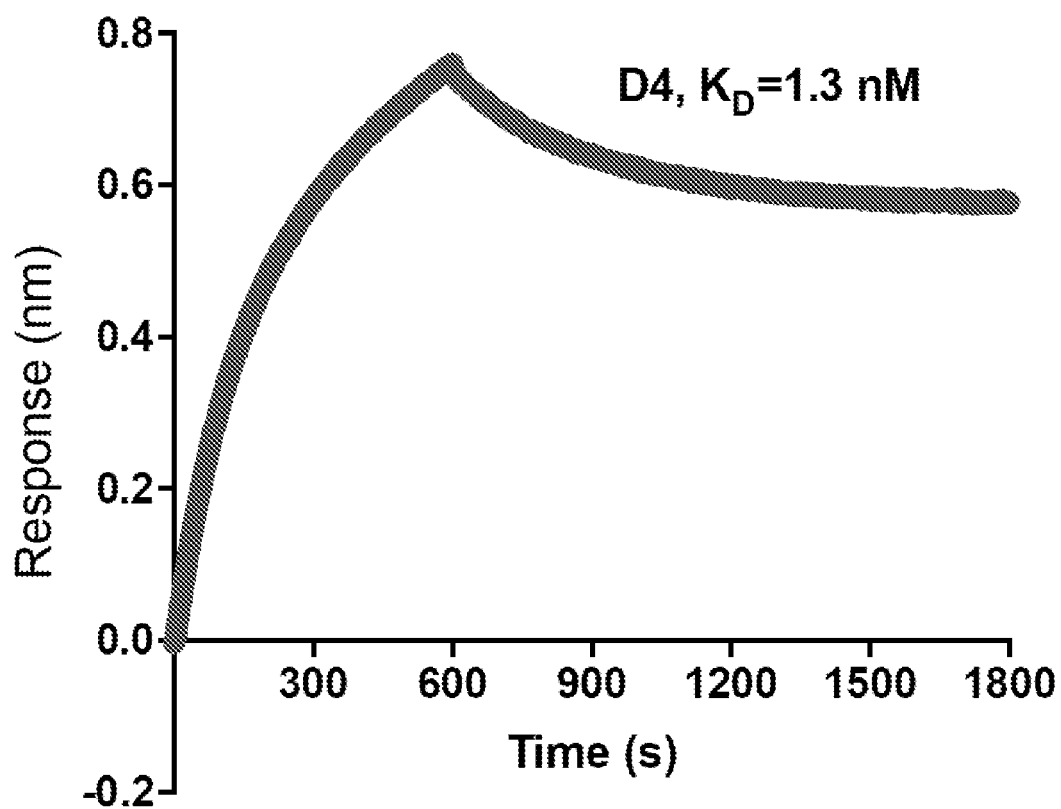
FIG. 3: Octet® kinetic analysis of the interaction between the D4 antibody and human GPC1. Affinity of D4 for human GPC1 was calculated as $K_D=1.3$ nM.

Antibody D4 was isolated from a camel single-domain (VHH) phage library after three rounds of panning (FIG. 1A). Monoclonal phage ELISA analysis of D4 demonstrated that D4 specifically binds both human and mouse GPC1, but does not exhibit any significant binding to human GPC2, GPC3, GPC5 or GPC6 (FIG. 1B). Binding of D4 to GPC1-expressing tumor cells was evaluated by flow cytometry. D4 exhibited significant binding to GPC1-overexpressing 2B9 KLM pancreatic cancer cells and GPC1-overexpressing H8 epidermoid carcinoma cells, but not to GPC1-negative A431 cells (FIG. 2). Using Octet® kinetic analysis, the affinity of D4 for human GPC1 was calculated as $K_D$=1.3 nM (FIG. 3).

Figure 4:
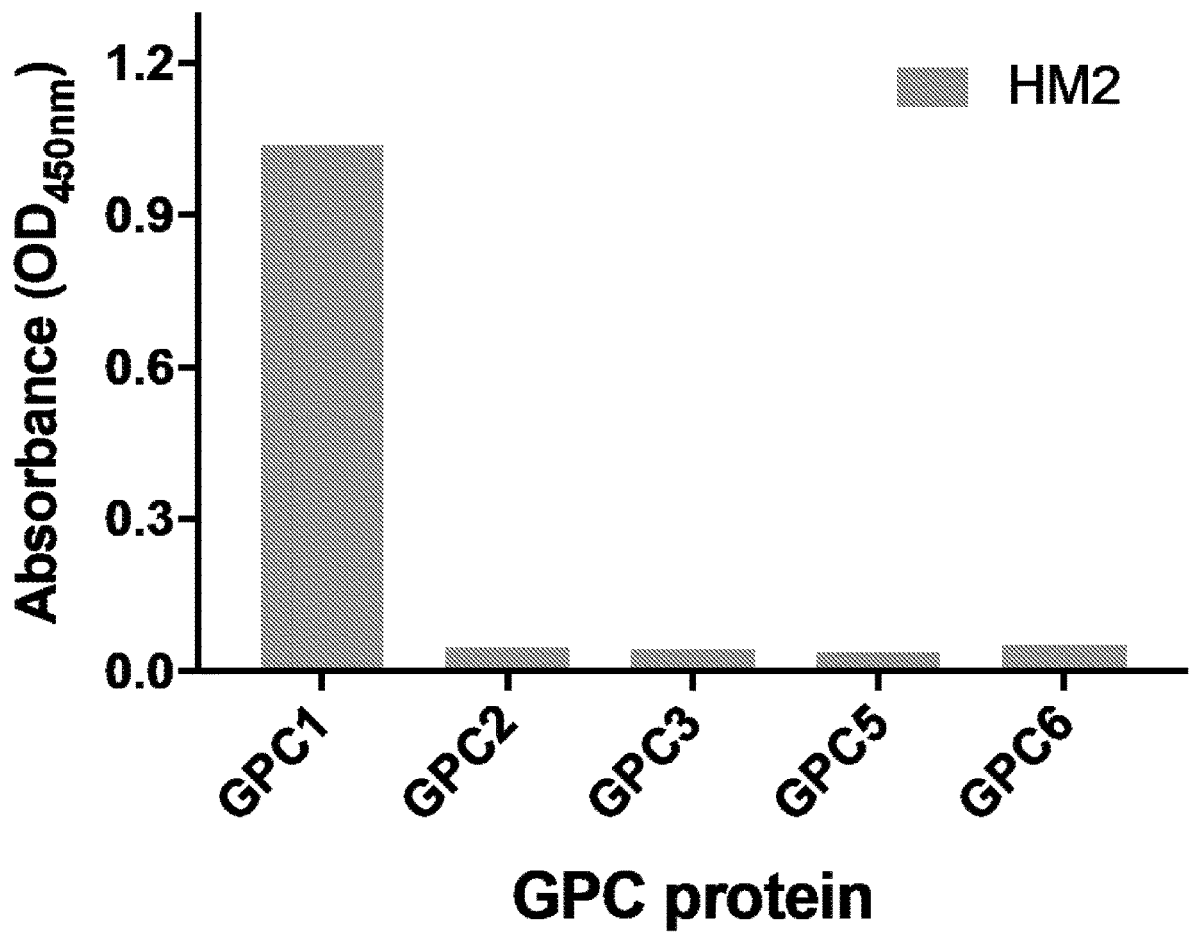
FIG. 4: Binding of the HM2 anti-GPC1 monoclonal antibody to GPC1 and other glypican proteins was evaluated by ELISA. HM2 specifically bound GPC1.
Figure 5:
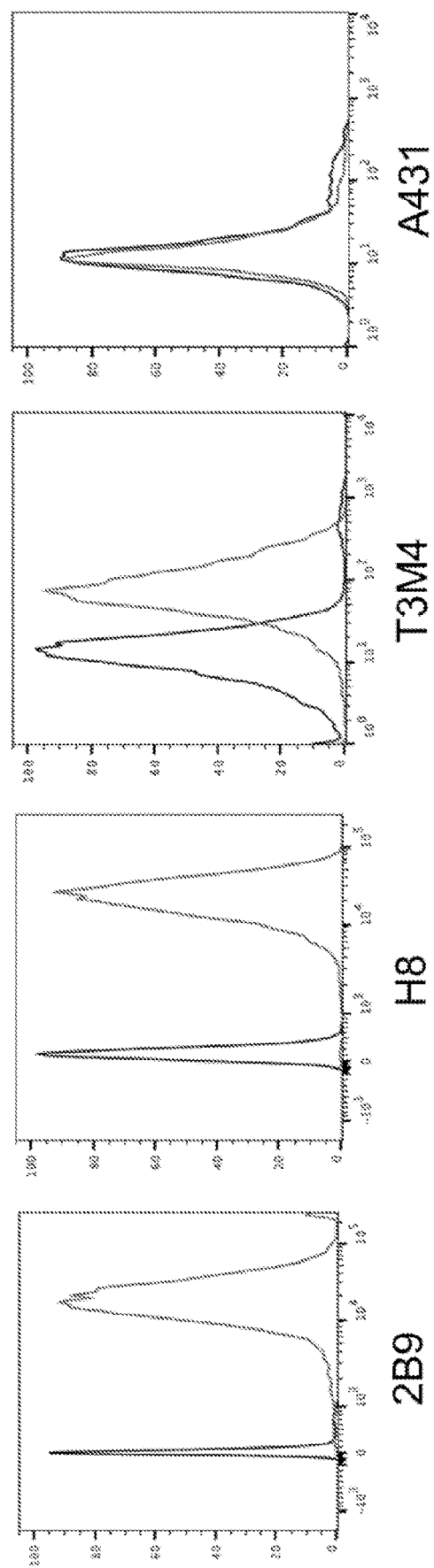
FIG. 5: Flow cytometry analysis of cell-surface GPC1 expression using the HM2 antibody. Binding of HM2 to GPC1-overexpressing 2B9 KLM pancreatic cancer cells, GPC1-overexpressing H8 epidermoid carcinoma cells, GPC1-positive T3M4 pancreatic cancer cells, and GPC1-negative A431 cells was evaluated. White peaks represent cell-surface staining with an isotype control antibody, and shaded peaks represent cell-surface staining with the GPC1-specific HM2 antibody. HM2 was used at a concentration of 10 µg/ml.
Figure 6:
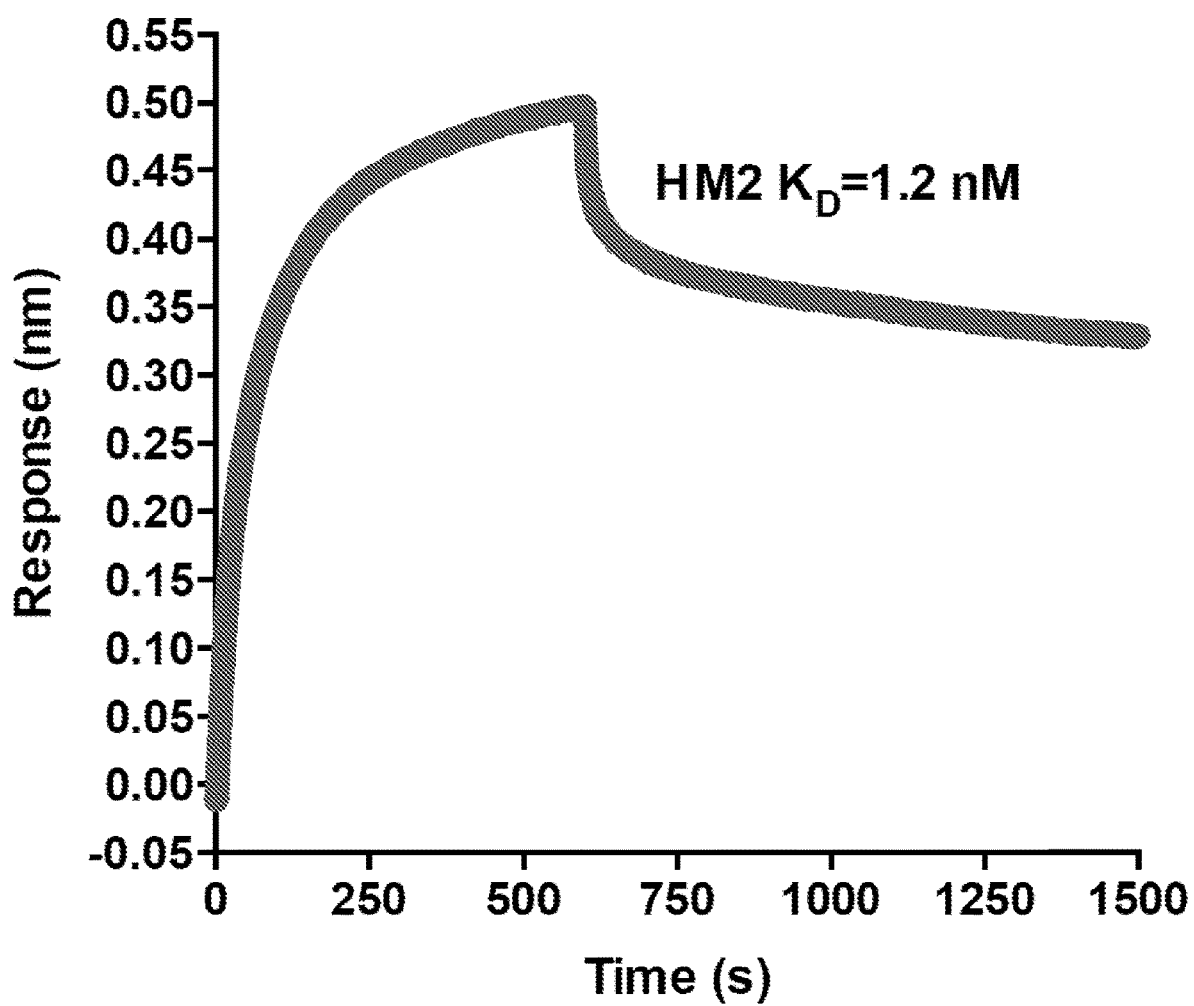
FIG. 6: Octet® kinetic analysis of interaction between the HM2 antibody and human GPC1. Affinity of HM2 for human GPC1 was calculated as $K_D=1.2$ nM.

Antibody HM2 was isolated from the mice immunized with a recombinant GPC1 fragment and screened on GPC1-positive cells following a previously described protocol (Phung et al., *mAbs* 4(5):592-599, 2012). An ELISA demonstrated that HM2 specifically binds human GPC1, but not human GPC2, GPC3, GPC5 or GPC6 (FIG. 4). Binding of HM2 to GPC1-expressing tumor cells was evaluated by flow cytometry. HM2 exhibited significant binding to GPC1-overexpressing 2B9 KLM pancreatic cancer cells, GPC1-overexpressing H8 epidermoid carcinoma cells and GPC1-positive T3M4 pancreatic cancer cells, but not to GPC1-negative A431 cells (FIG. 5). Using Octet® kinetic analysis, the affinity of HM2 for human GPC1 was calculated as $K_D$=1.2 nM (FIG. 6).

Figure 7:
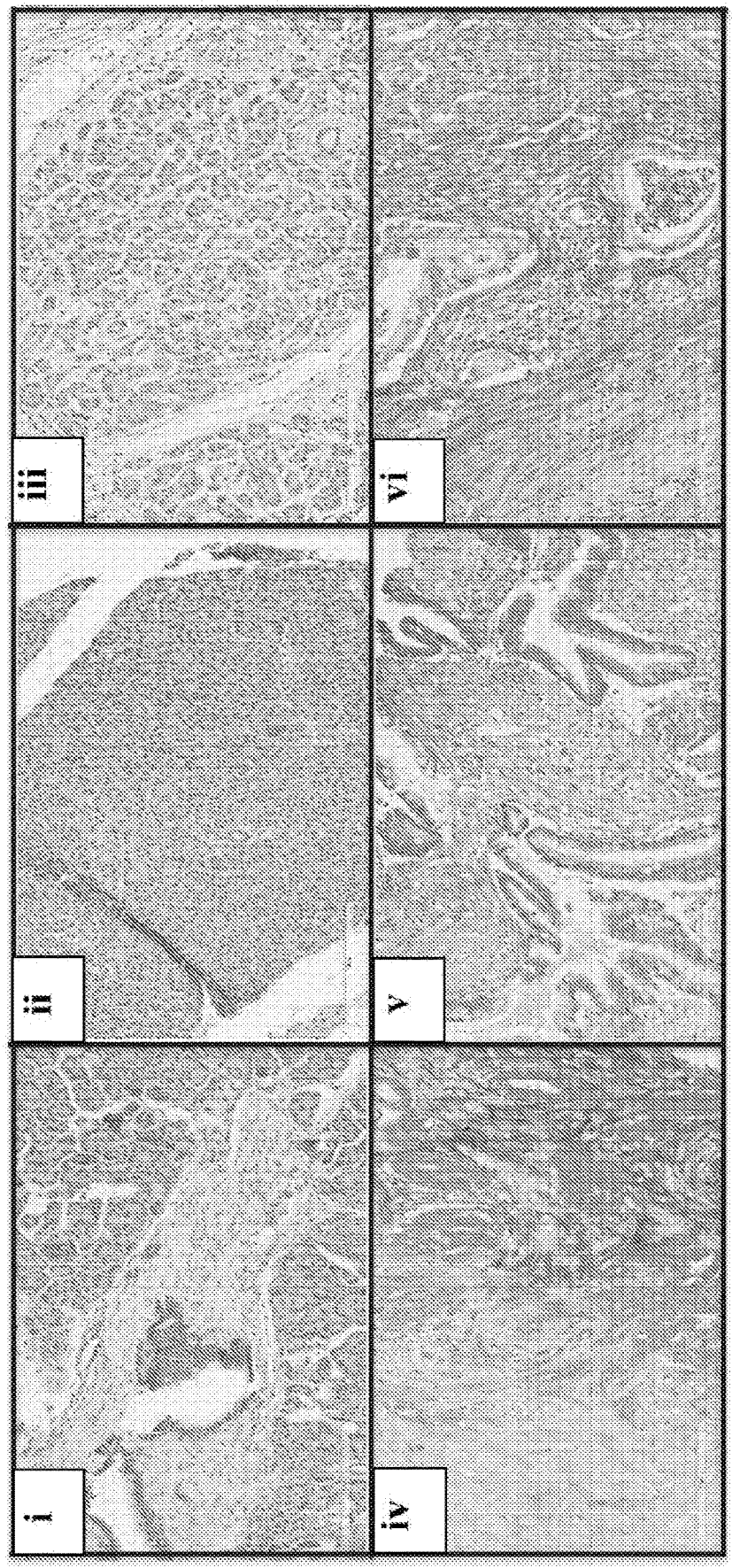
FIG. 7: GPC1 expression in human pancreatic tumors. Expression of GPC1 in normal pancreas (i to iii) and pancreatic tumors (iv to vi) as determined by immunohistochemistry. The tissues were labeled with 1 µg/ml HM2 antibody.

Using antibody HM2 (1 µg/ml), expression of GPC1 in human pancreatic tumors was evaluated by immunohistochemistry. As shown in FIG. 7, expression of GPC1 was significantly increased in pancreatic tumors (panels iv to vi of FIG. 7) relative to normal tissue (panels i to iii) and as determined by immunohistochemistry.

Figure 8A:
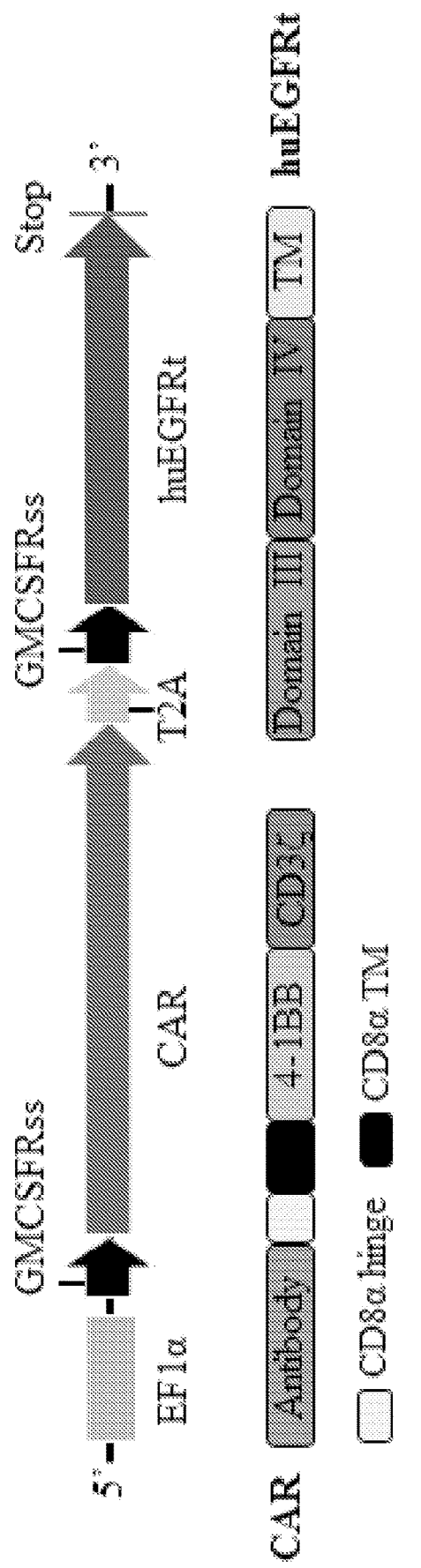
FIGS. 8A-8B: Generation of GPC1-targeted CAR T cells.
Figure 8B:
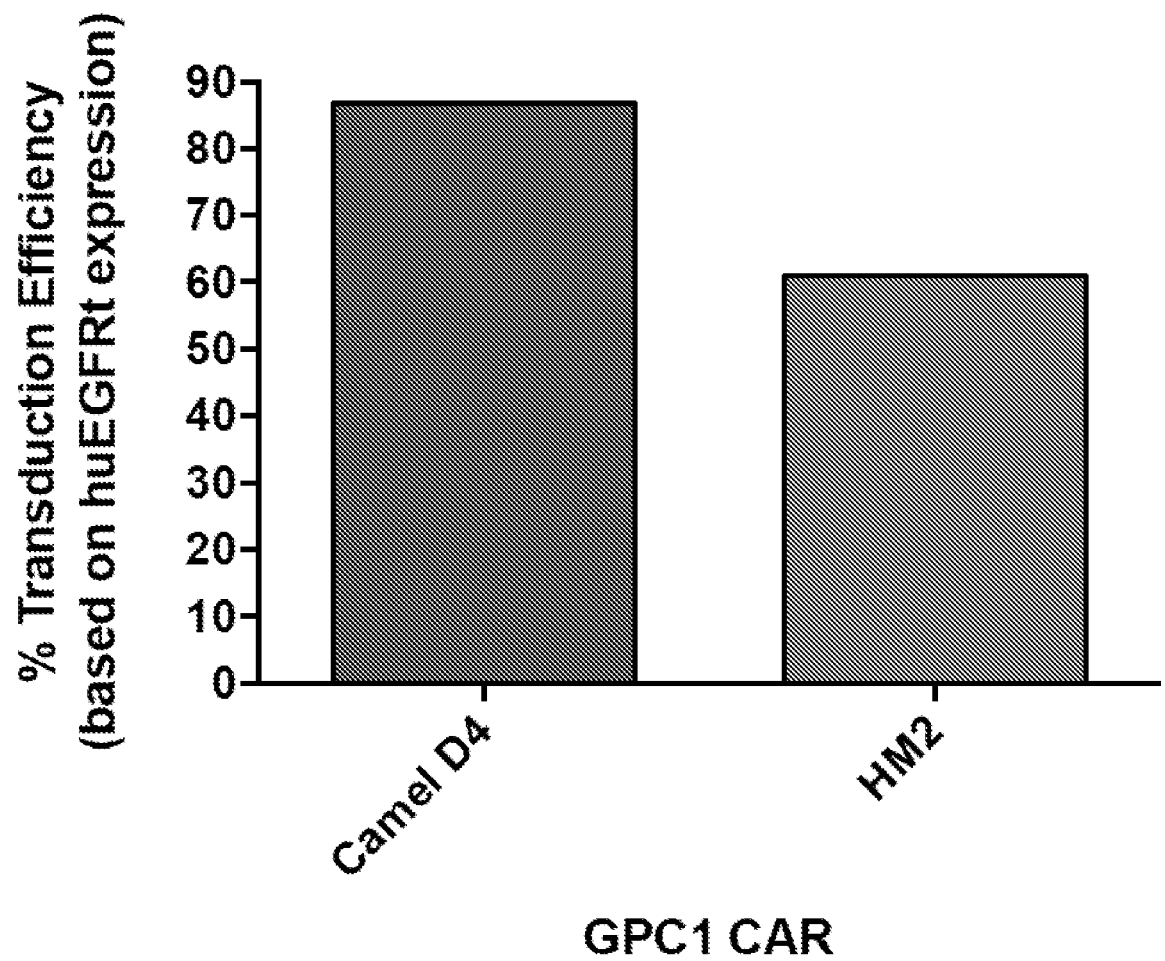

HM2 and D4 were used to generate GPC1-targeted CAR T cells. Lentiviral constructs expressing a CAR comprising HM2 scFv or VHH antibody D4 along with truncated human EGFR (huEGFRt) were produced (FIG. 8A; see also Section IV above). To confirm successful transduction of the vectors and expression of the CARs in T cells, flow cytometry was used to detect huEGFRt expression. As shown in FIG. 8B, the transduction efficiencies of D4 CAR and HM2 CAR in primary T cells were 86% and 58%, respectively.

Figure 9C:
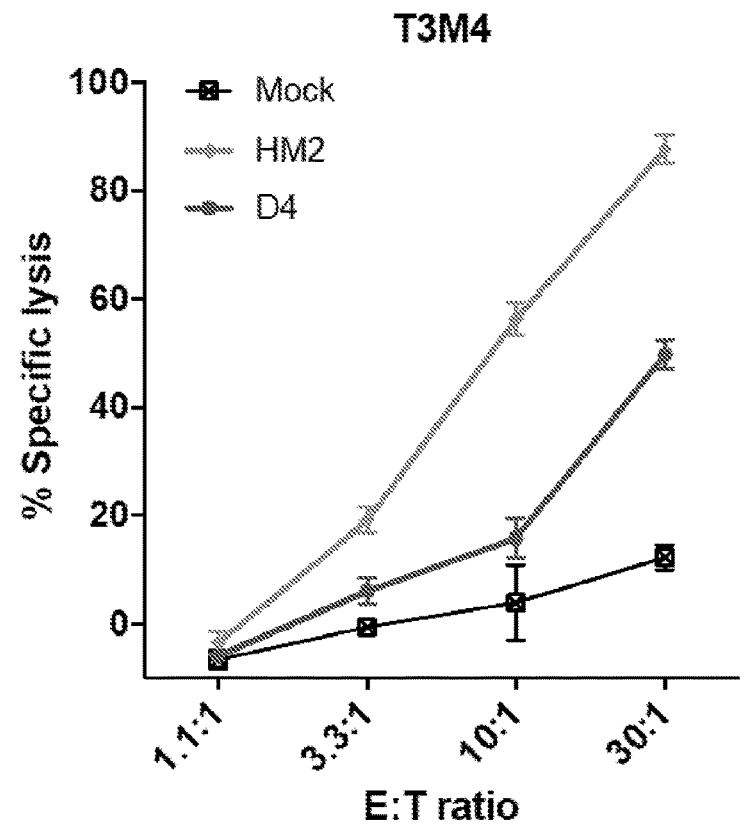
Figure 9D:
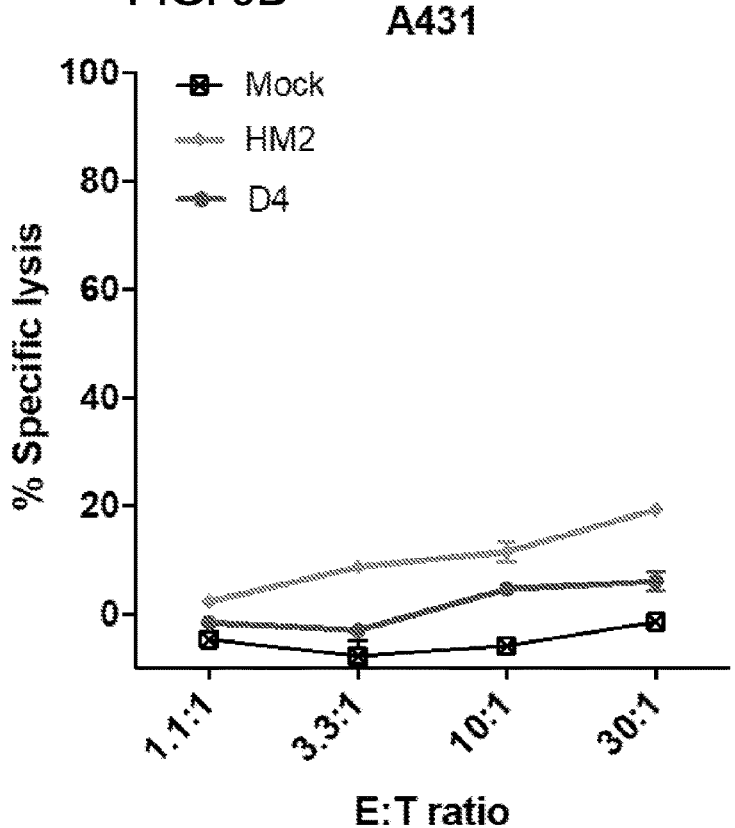

Cytolytic activity of HM2 and D4 CAR T cells was tested in vitro. Luciferase expressing 2B9 (GPC1-positive), H8 (GPC1-positive), T3M4 (GPC1-positive) and A431 (GPC1-negative) cells were co-cultured with mock, HM2 or D4 CAR-transduced T cells at E:T ratios ranging from 1.1:1 to 30:1 for 20 hours. Specific lysis was measured using a luminescent-based cytolytic assay. As shown in FIGS. 9A-9C, GPC1-targeted CAR T cells induced efficient lysis of all GPC1-expressing cell lines in a dose-dependent manner By contrast, minimal cell lysis was observed in GPC1-negative cell line A431 (FIG. 9D).

Figure 10A:
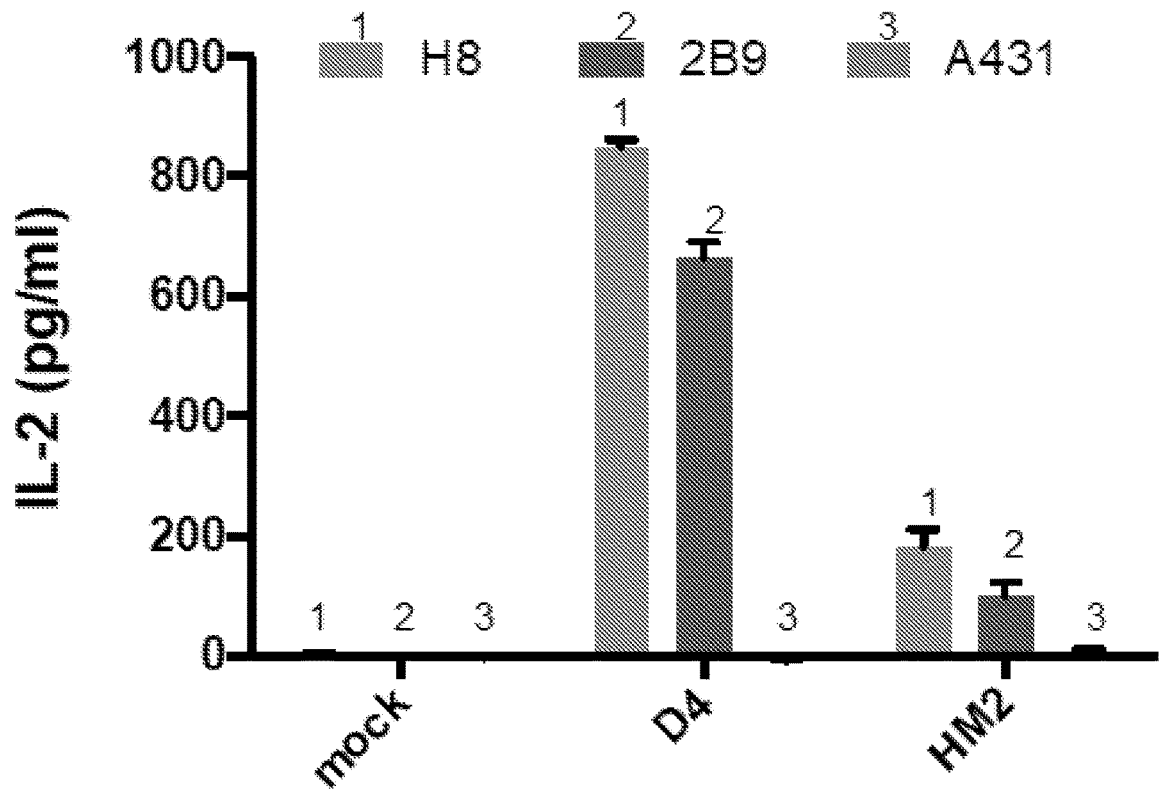
FIGS. 10A-10C: CAR T cells based on D4 or HM2 induce release of cytokines when co-cultured with GPC1-positive tumor cells. GPC1-positive and GPC1-negative tumor cells were co-cultured with GPC1-targeted CAR T cells for 20 hours at an E:T ratio of 10. The culture supernatants were harvested to measure IL-2 (FIG. 10A), IFN-γ (FIG. 10B) and TNF-α (FIG. 10C) secretions via ELISA.
Figure 10B:
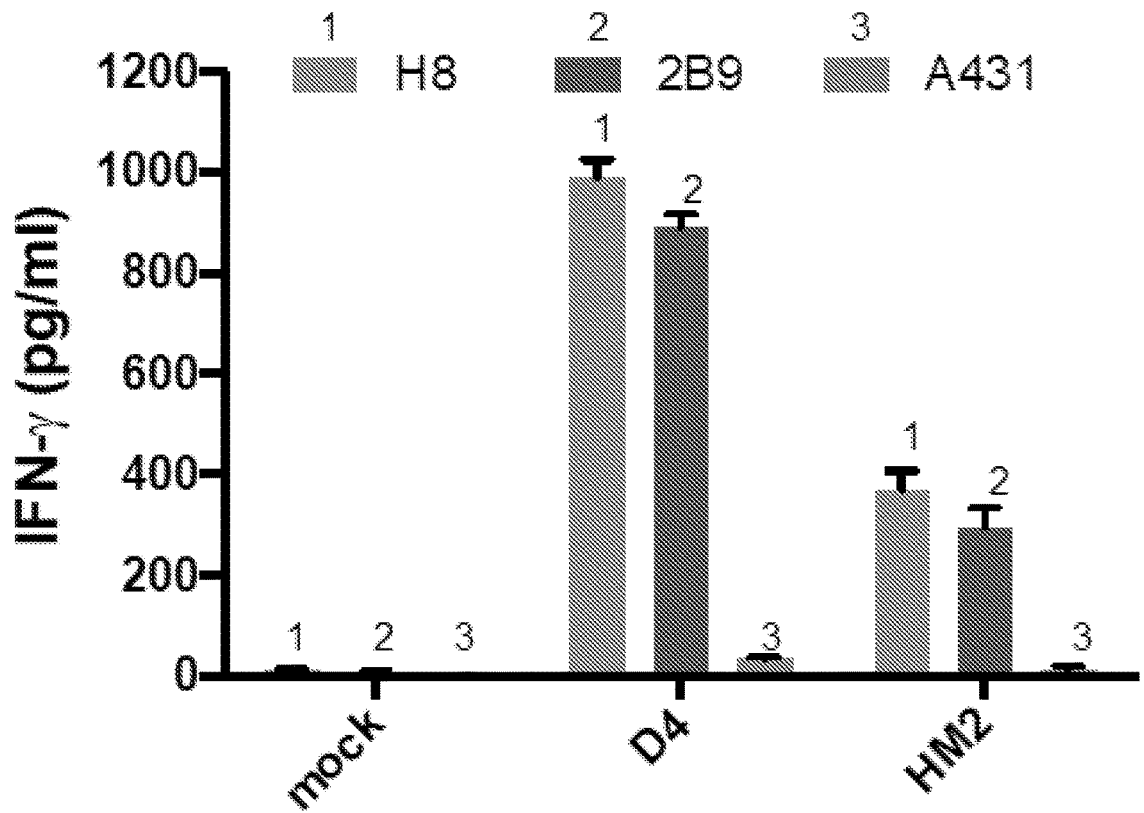
Figure 10C:
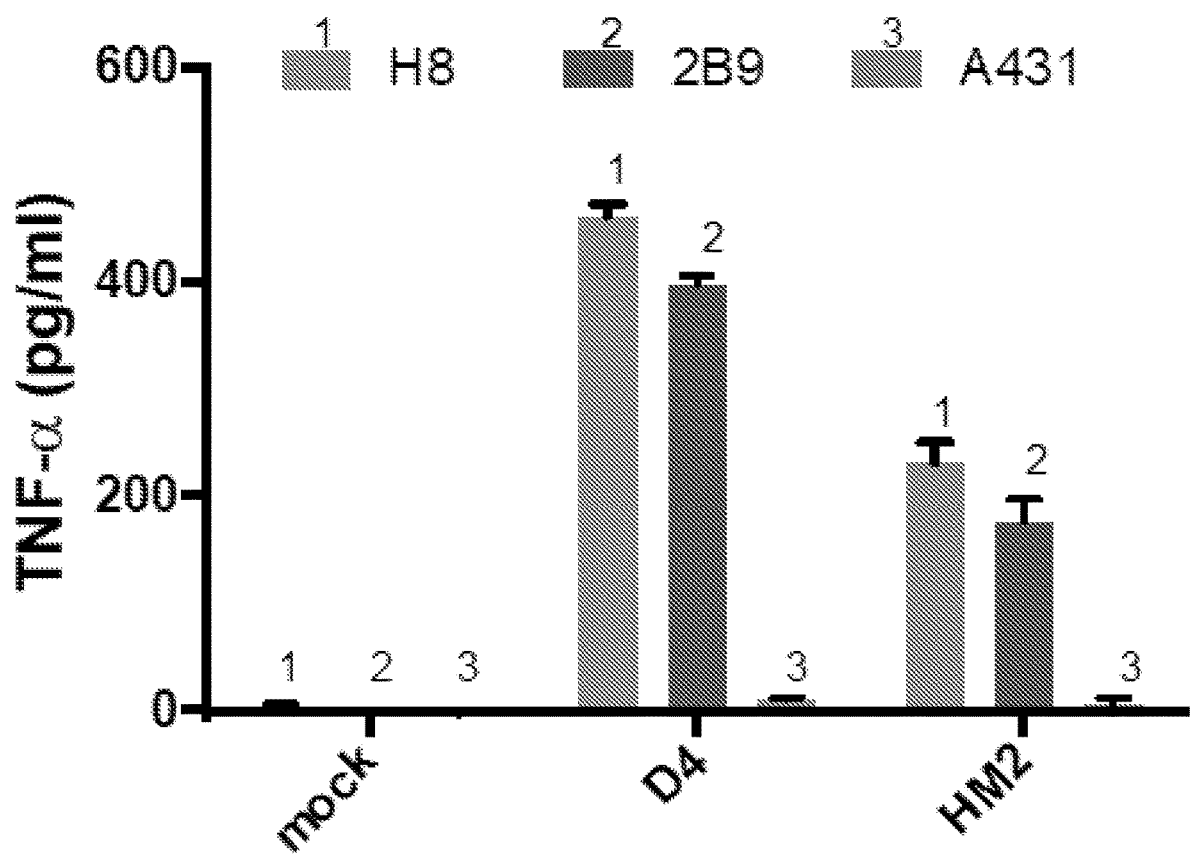

Additional studies were conducted to evaluate cytokine production induced by GPC1-targeted CART cells. GPC1-positive (H8 and 2B9) and GPC1-negative (A431) tumor cells were co-cultured with GPC1-targeted HM2 or D4 CAR T cells for 20 hours at an E:T ratio of 10. The culture supernatants were harvested to measure IL-2 (FIG. 10A), IFN-γ (FIG. 10B) and TNF-α (FIG. 10C) secretions via ELISA. D4 and HM2 CAR T cells led to increased production of IL-2, IFN-γ, and TNF-α in both GPC1-positive cells lines, but not in GPC1-negative A431 cells. Although both HM2 and D4 CAR T cells showed similar cytolytic activity in vitro, D4 CAR T cells induced 2- to 4-fold more cytokine than HM2 CAR T cells when co-cultured with GPC1-positive tumor cells.

Figure 11A:
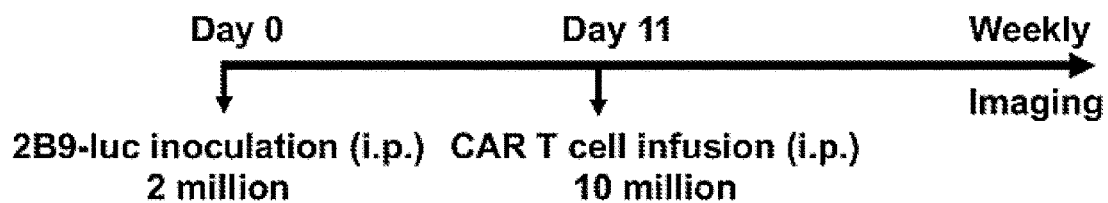
FIGS. 11A-11E: GPC1-targeted CAR T cells demonstrate potent activity in mice bearing human pancreatic tumors.
Figure 11B:
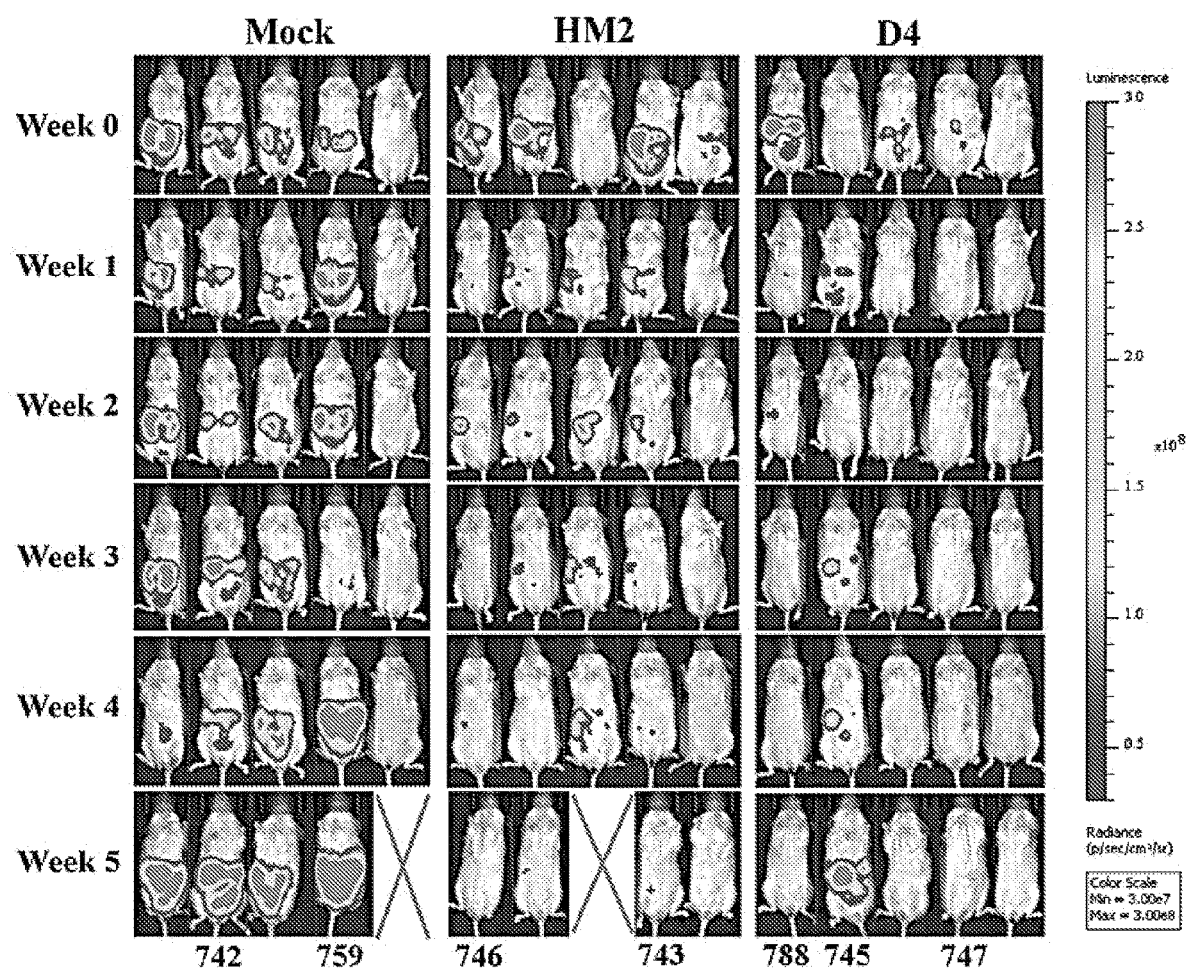
Figure 11C:
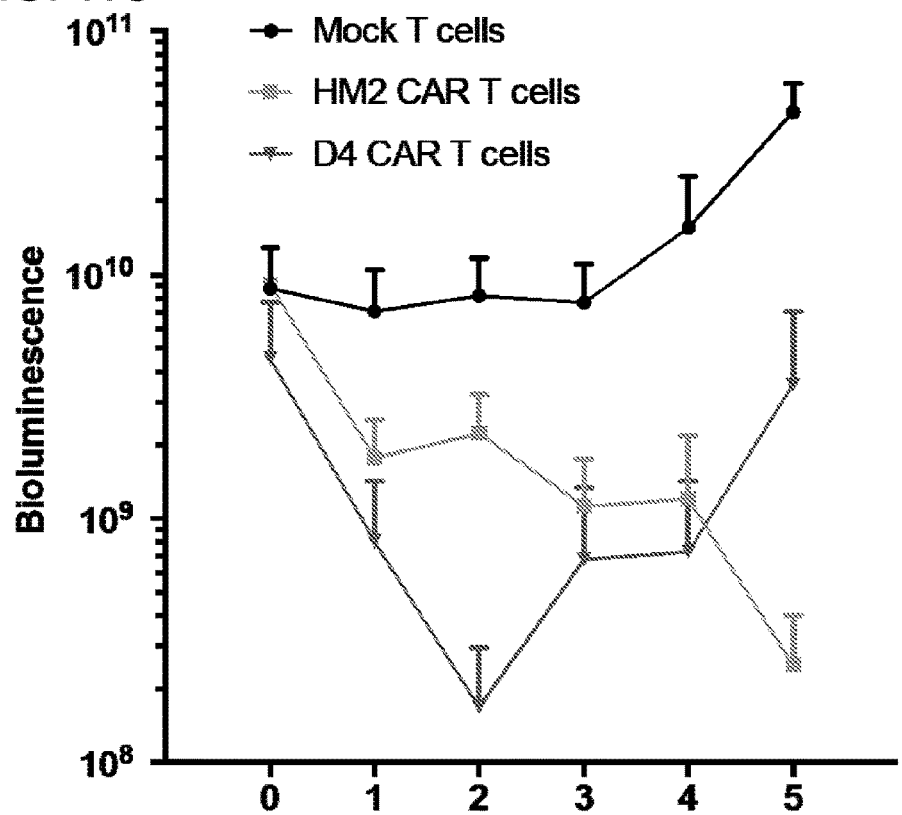
Figure 11D:
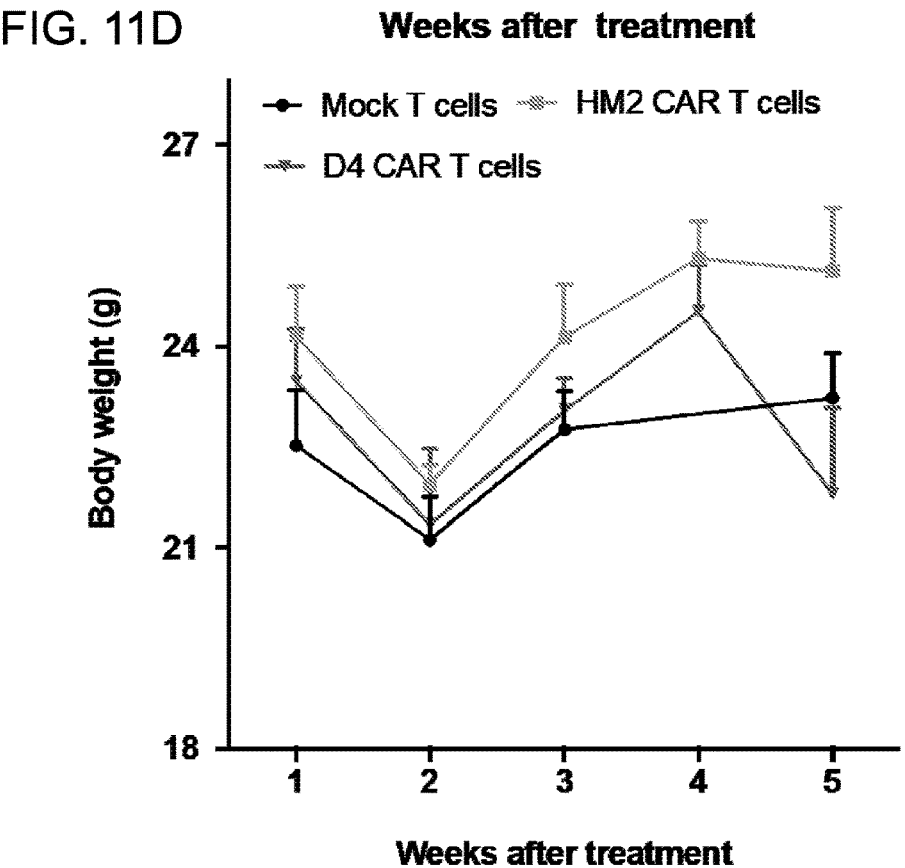
Figure 11E:
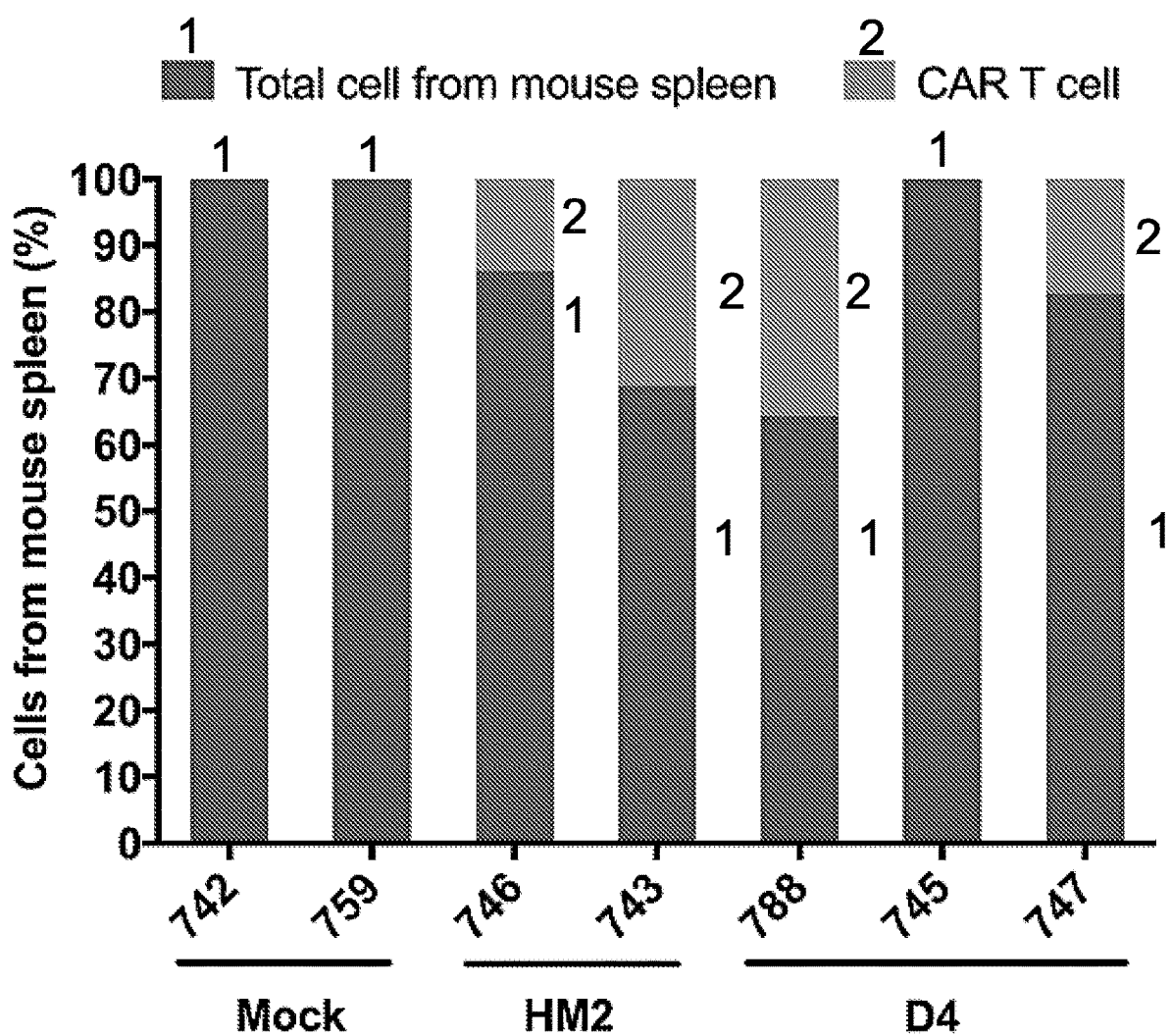
Figure 12A:
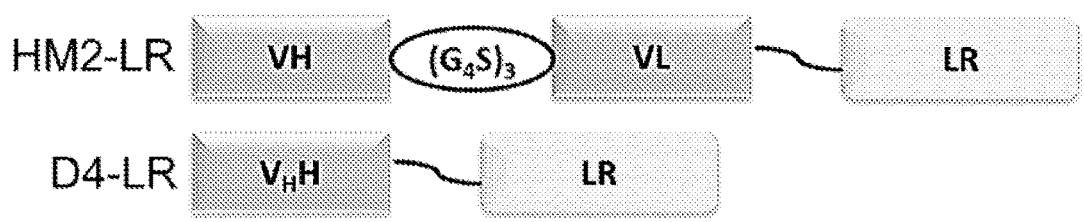
FIGS. 12A-12B: Generation of anti-GPC1 immunotoxins.
Figure 12B:
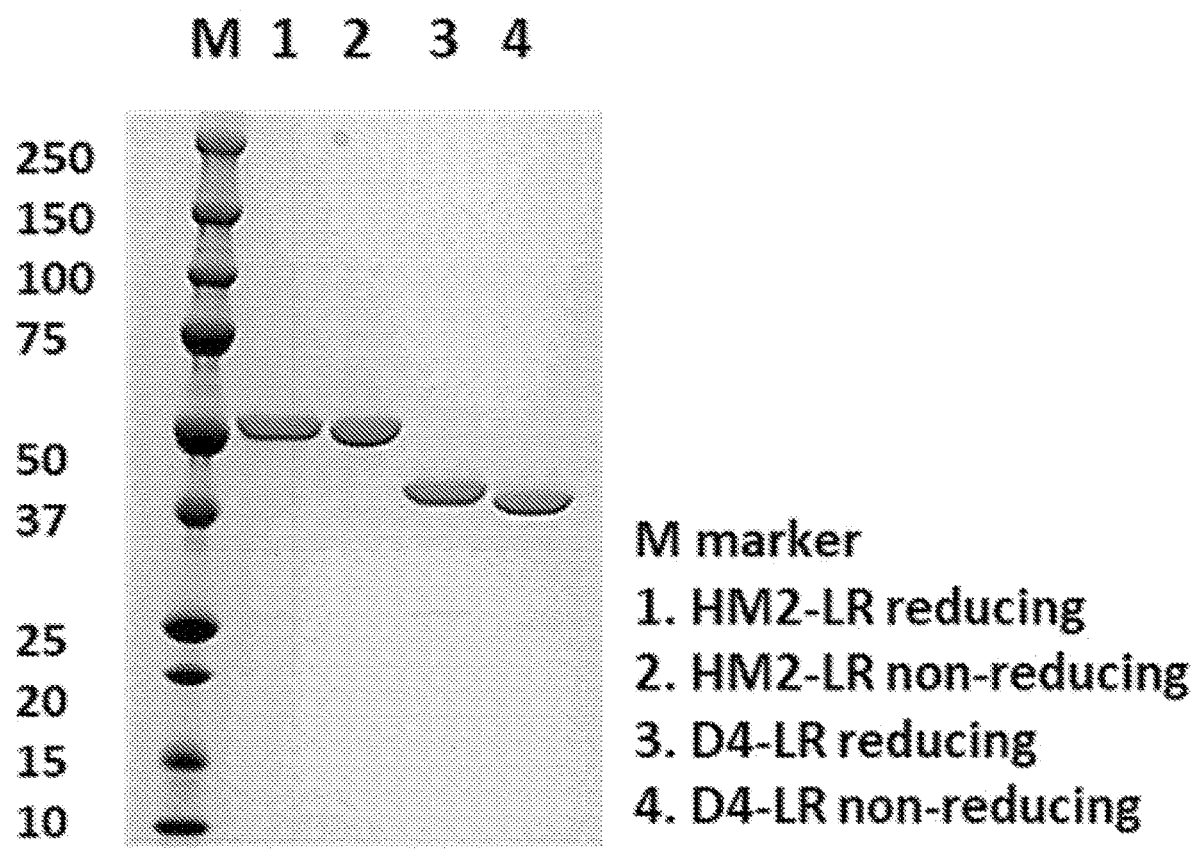
Figures 13A, 13B:
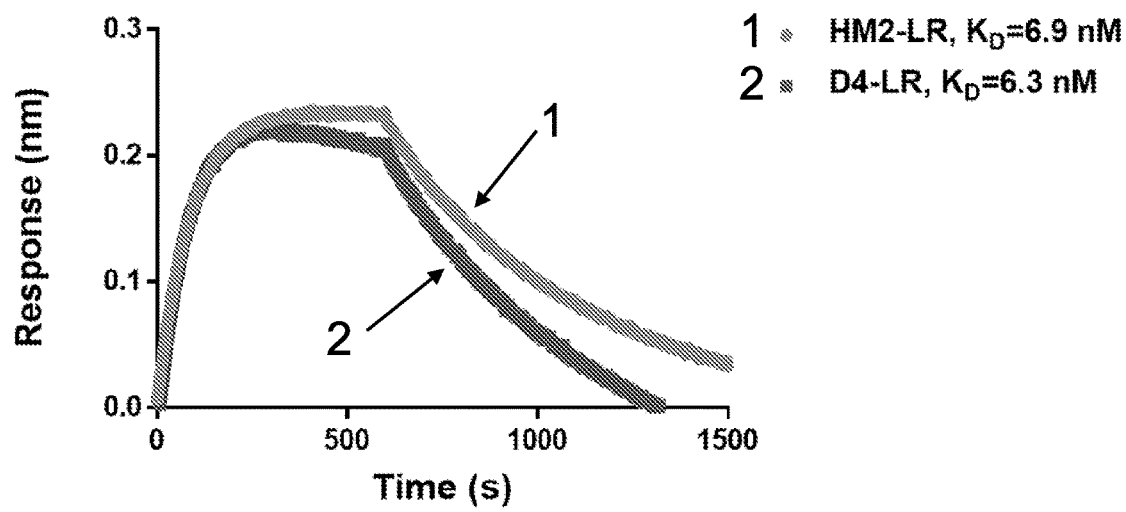
FIGS. 13A-13B: Anti-GPC1 immunotoxins retain high affinity for GPC1.
Figure 14A:
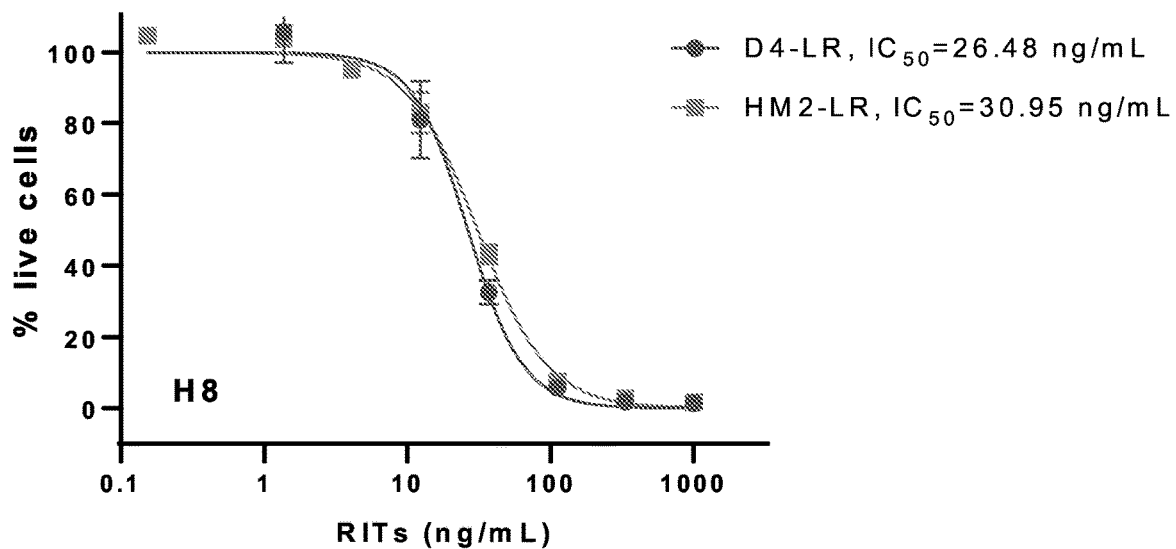
FIGS. 14A-14D: Anti-GPC1 immunotoxins kill GPC1$^+$ cancer cells in vitro. Cytotoxicity assays were performed on GPC1-positive cell lines H8 (FIG. 14A), 2B9 (FIG. 14B) and T3M4 (FIG. 14C), and GPC1-negative cell line A431 (FIG. 14D) using WST-8 reagent after three days incubation. The D4-LR and HM2-LR immunotoxins efficiently killed GPC1 overexpressing H8 and 2B9 cell lines with IC50 values ranging from 14 to 31 ng/ml. However, both immunotoxins exhibited inferior cell killing capacity on the native pancreatic cancer cell line T3M4, which has a relatively lower GPC1 expression level. Neither immunotoxin was capable of killing GPC1-negative A431 cells, indicating specificity of the immunotoxins for GPC1-expressing cells.
Figure 14B:
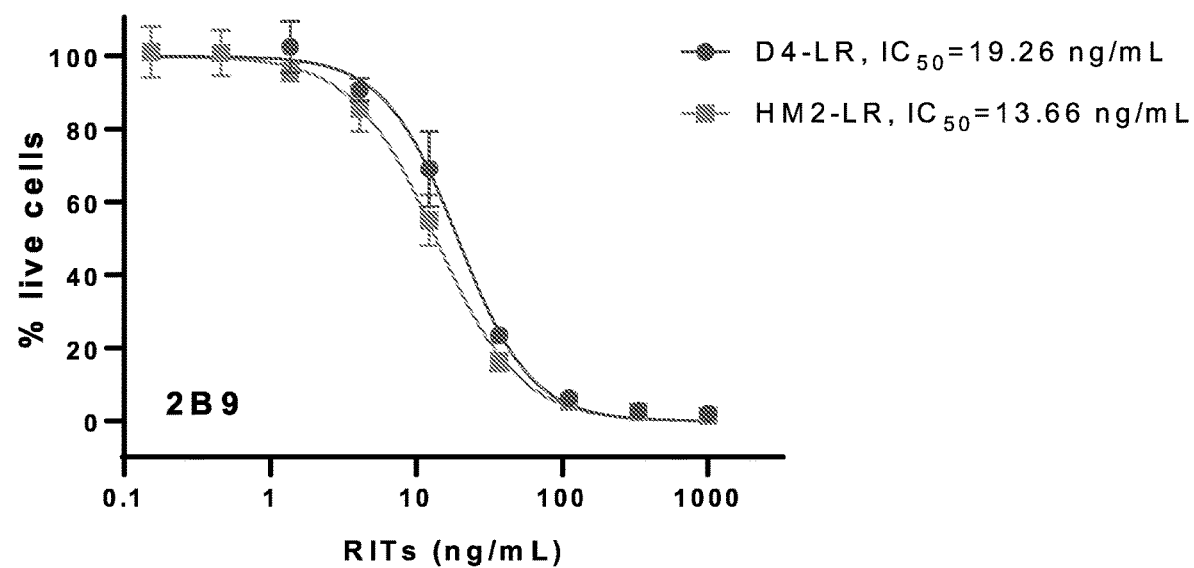
Figure 14C:
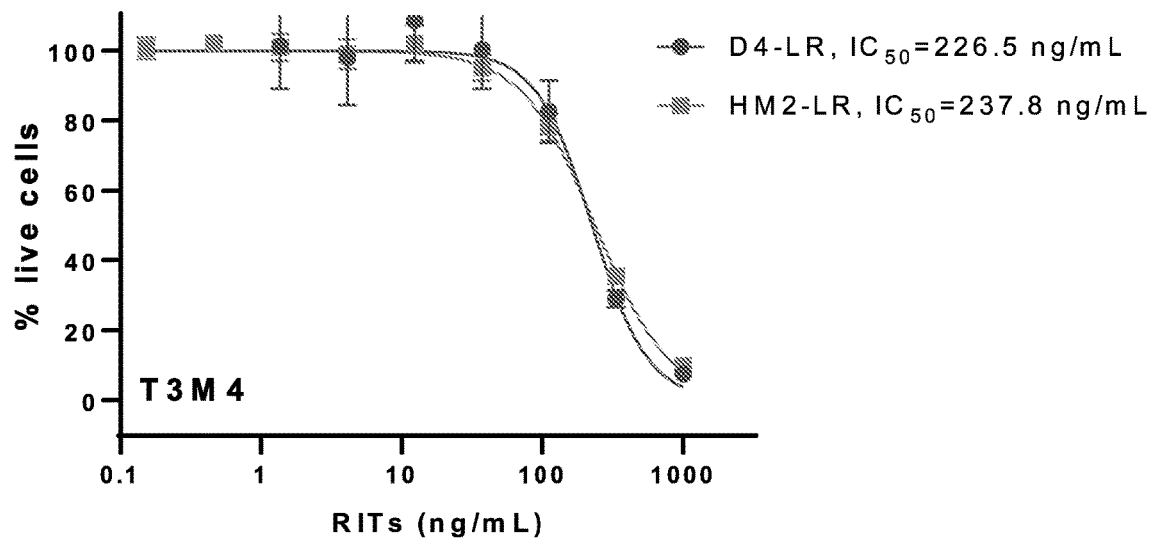
Figure 14D:
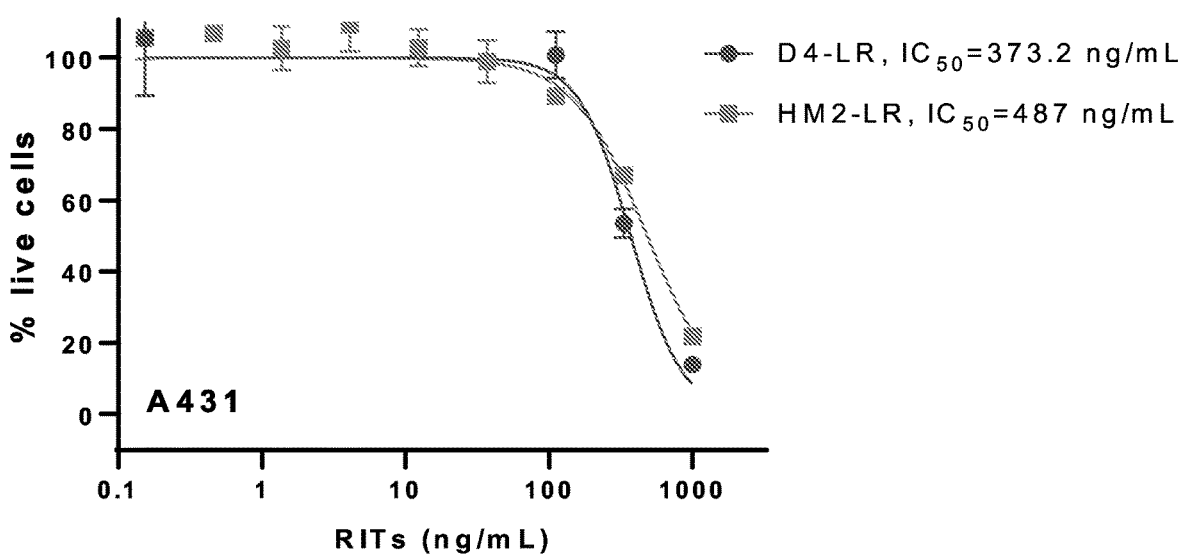
Figure 15A:
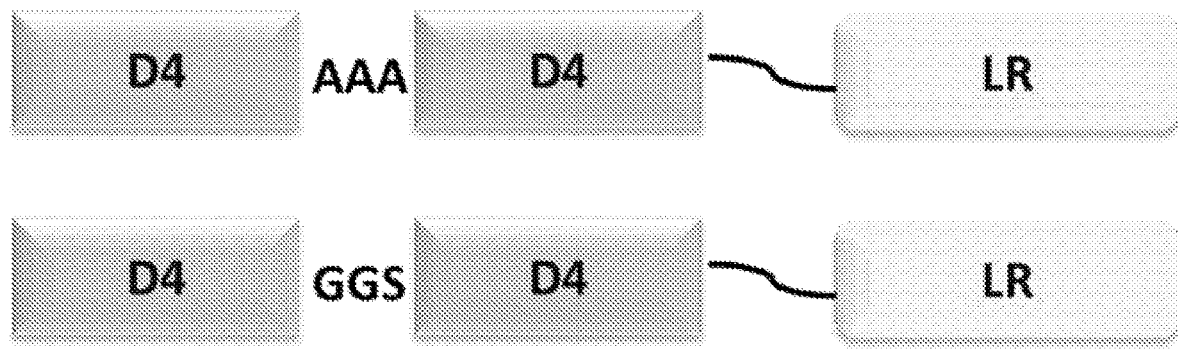
FIGS. 15A-15B: Generation of bivalent D4 immunotoxins.
Figure 15B:
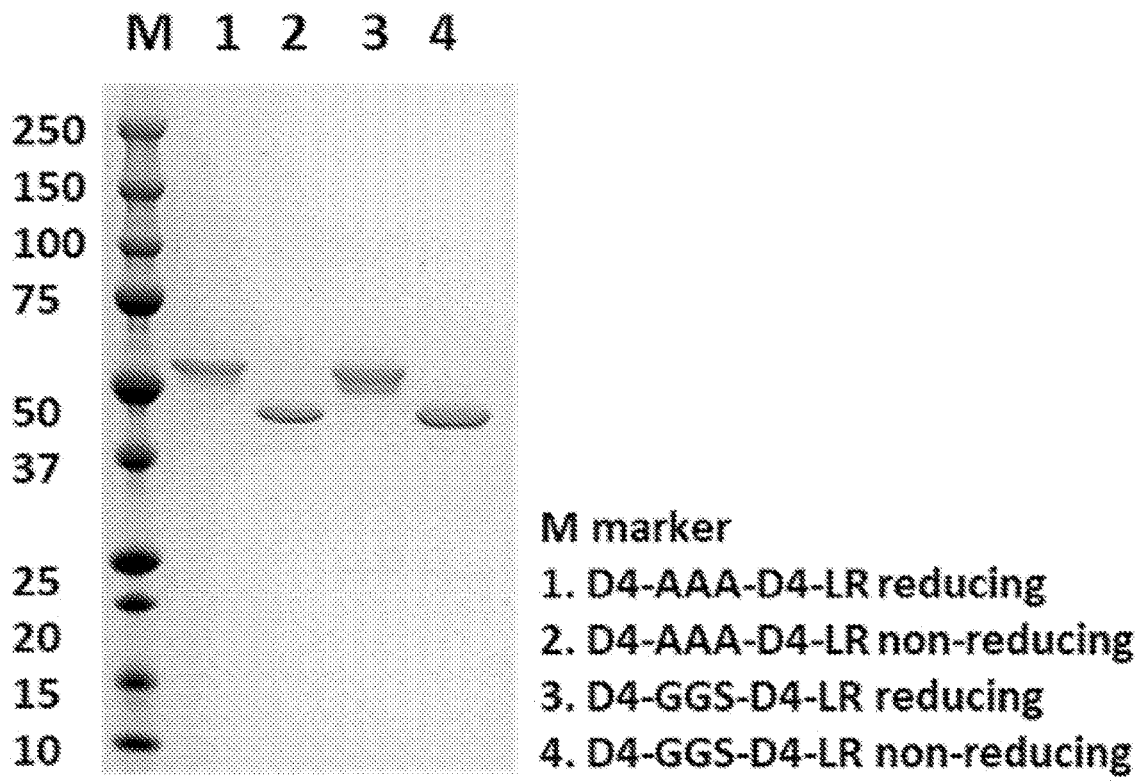

GPC1-targeted CAR T cells based on antibody HM2 or D4 were evaluated in a peritoneal dissemination xenograft mouse model of pancreatic cancer. 2B9 tumor-bearing NSG mice were treated with peritoneal injection of either mock T cells or CAR T cells at day 11 after tumor cell inoculation (FIG. 11A). Tumor burden was monitored by bioluminescent imaging. HM2 and D4 CAR T cells demonstrated potent antitumor activity and mediated eradication of 2B9 xenograft tumors (FIGS. 11B and 11C). Body weights of mice did not significantly differ between the three groups of treated animals (FIG. 11D). To determine the proportion of spleen cells that were CAR vector positive, droplet digital PCR (ddPCR) was performed. Genomic DNA was extracted from the spleens of select mice (742, 759, 746, 743, 788, 745 and 747; see FIG. 11B) and analyzed by ddPCR to quantify CAR T cells. The percentage of CAR T cells in the spleens of mock-treated, HM2-treated and D4-treated mice is shown in FIG. 11E. The results demonstrated that the GPC1-targeted CAR T cells were persistent in mice even 5 weeks after treatment, and the quantity of CAR T cells was inversely correlated with tumor burden. These findings indicate that GPC1-targeted CAR T cell therapy is an effective approach for treating pancreatic cancer and other GPC1-expressing cancers.

Example 2: Immunotoxins Based on the D4 and HM2 Antibodies

This example describes the generation and testing of immunotoxins comprised of the D4 or HM2 antibody and a truncated form of *Pseudomonas* exotoxin A that lacks domain II (referred to herein as "LR").

Immunotoxin Sequences

Four different immunotoxins were generated: D4-LR, HM2-LR, D4-AAA-D4-LR and D4-GGS-D4-LR. The latter two immunotoxins include dimers of D4 separated by a three-amino acid linker (AAA or GGS). The nucleotide and amino acid sequences of the four immunotoxins are provided below. The LR coding sequence (for the nucleotide sequences) and the LR portion of the amino acid sequences are underlined.

```
D4-LR nucleotide sequence
                                              (SEQ ID NO: 14)
ATGCAGGTGCAGCTGGTGGAGTCTGGGGGAGGCTTGGTGCAGCCCGGGGGGTCTCTGA

GACTCTCCTGTGTAGCCTCTGGATACAGCTACAGTATTGGTTACATGGCCTGGTTCCGC

CAGGCCCCAGGAAAGGAGCGCGCGTGGGTCGCGTCTCGATATACTGGTGACGGTGGC

GCAGTCTTTGACGACGCCGTGAAGGGCCGATTCACCACCTCCCAAGAGAGTGCCGGGA

ACACGTTCGATTTGCAAATGGACAGCCTGAAACCTGAGGACACTGCCATGTACTATTG

CGCAGCGAAAGGGCCCGGTTTCGGGCGGTGGGAGTACTGGGGCCGGGGGACCCAGGT

CACCGTCTCCTCAAAGCTTAAAGCAAGCGGCGGTCGCCATCGCCAGCCGCGCGGCTGG

GAACAGCTGGGCGGTGGCGGTGGCAGCCCCACCGGTGCCGAGTTCCTGGGCGACGGT

GGCGATGTGTCCTTTAGCACCCGTGGTACCCAGAACTGGACGGTAGAGCGCCTGCTGC

AGGCACATCGTCAGCTGGAAGAGCGTGGCTATGTATTCGTTGGCTACCACGGCACTTT

TCTGGAAGCAGCTCAGTCCATCGTGTTTGGTGGTGTCCGTGCCCGTTCTCAAGACCTGG

ATGCGATTTGGCGTGGTTTCTACATTGCAGGCGATCCAGCGCTGGCATACGGTTATGCG

CAGGACCAGGAACCGGATGCTCGTGGTCGCATTCGTAATGGTGCGCTGCTGCGCGTAT

ATGTGCCGCGTTCCAGCCTGCCGGGCTTCTACCGCACTAGCCTGACCCTGGCCGCGCCG

GAGGCGGCGGGTGAAGTGGAACGTCTGATTGGTCATCCTCTGCCTCTGCGCCTGGATG

CCATCACCGGCCCAGAGGAGGAGGGCGGTCGTCTGGAAACCATTCTGGGCTGGCCGCT

GGCTGAACGTACGGTCGTTATTCCGAGCGCGATTCCTACCGATCCTCGTAACGTTGGCG

GCGATCTGGACCCATCTTCTATTCCAGATAAGGAGCAGGCAATCTCCGCGCTGCCGGA

TTATGCAAGCCAACCGGGTAAACCACCTCGTGAAGATCTGAAATAA

D4-LR amino acid sequence
                                              (SEQ ID NO: 15)
MQVQLVESGGGLVQPGGSLRLSCVASGYSYSIGYMAWFRQAPGKERAWVASRYTGDGG

AVFDDAVKGRFTTSQESAGNTFDLQMDSLKPEDTAMYYCAAKGPGFGRWEYWGRGTQV

TVSSKLKASGGRHRQPRGWEQLGGGGGSPTGAEFLGDGGDVSFSTRGTQNWTVERLLQA

HRQLEERGYVFVGYHGTFLEAAQSIVFGGVRARSQDLDAIWRGFYIAGDPALAYGYAQD

QEPDARGRIRNGALLRVYVPRSSLPGFYRTSLTLAAPEAAGEVERLIGHPLPLRLDAITGPE

EEGGRLETILGWPLAERTVVIPSAIPTDPRNVGGDLDPSSIPDKEQAISALPDYASQPGKPPR

EDLK
```

HM2-LR nucleotide sequence
(SEQ ID NO: 16)
ATGGAGGTTCAGCTGCAGCAGTCTGGGGCTGAGCTTGTGAGGCCAGGGGCCTCAGTCA

AGTTGTCCTGCACAGCTTCTGGCTTTAACATTAAAGACGACTATATGCACTGGGTGAA

GCAGAGGCCTGAACAGGGCCTGGAGTGGATTGGATGGATTGATCCTGAGAATGGTGAT

ACTGAATATGCCTCGAAGTTCCAGGGCAAGGCCACTATAACAGCAGACACATCCTCCA

ACACAGCCTACCTGCAGCTCAGCAGCCTGACATCTGAGGACACTGCCGTCTATTACTG

TACTCGTAGCTCCGTAGGCTACTGGGGCCAAGGCACCACTCTCACAGTCTCCTCAGGC

GGAGGCGGATCAGGTGGTGGCGGATCTGGAGGTGGCGGAAGCGATGTTGTGATGACC

CAAACTCCACTCTCCCTGCCTGTCAGTCTTGGAGATCAAGCCTCCATCTCTTGCAGATC

TAGTCAGAGCCTTGTACACAGTAATGGAAACACCTATTTACATTGGTACCTGCAGAAG

CCAGGCCAGTCTCCAAAGCTCCTGATCTACAAAGTTTCCAACCGATTTTCTGGGGTCCC

AGACAGGTTCAGTGGCAGTGGATCAGGGACTTATTTCACACTCAAGATCAGCAGAGTG

GAGGCTGAGGATCTGGGAGTTTATTTCTGCTCTCAAAGAACACATGTTCCGTACACGTT

CGGAGGGGGGACCAAGCTGGAGATAAAAAAGCTTAAAGCAAGCGGCGGTCGCCATCG

CCAGCCGCGCGGCTGGGAACAGCTGGGCGGTGGCGGTGGCAGCCCCACCGGTGCCGA

GTTCCTGGGCGACGGTGGCGATGTGTCCTTTAGCACCCGTGGTACCCAGAACTGGACG

GTAGAGCGCCTGCTGCAGGCACATCGTCAGCTGGAAGAGCGTGGCTATGTATTCGTTG

GCTACCACGGCACTTTTCTGGAAGCAGCTCAGTCCATCGTGTTTGGTGGTGTCCGTGCC

CGTTCTCAAGACCTGGATGCGATTTGGCGTGGTTTCTACATTGCAGGCGATCCAGCGCT

GGCATACGGTTATGCGCAGGACCAGGAACCGGATGCTCGTGGTCGCATTCGTAATGGT

GCGCTGCTGCGCGTATATGTGCCGCGTTCCAGCCTGCCGGGCTTCTACCGCACTAGCCT

GACCCTGGCCGCGCCGGAGGCGGCGGGTGAAGTGGAACGTCTGATTGGTCATCCTCTG

CCTCTGCGCCTGGATGCCATCACCGGCCCAGAGGAGGAGGGCGGTCGTCTGGAAACCA

TTCTGGGCTGGCCGCTGGCTGAACGTACGGTCGTTATTCCGAGCGCGATTCCTACCGAT

CCTCGTAACGTTGGCGGCGATCTGGACCCATCTTCTATTCCAGATAAGGAGCAGGCAA

TCTCCGCGCTGCCGGATTATGCAAGCCAACCGGGTAAACCACCTCGTGAAGATCTGAA

ATAA

HM2-LR amino acid sequence
(SEQ ID NO: 17)
MEVQLQQSGAELVRPGASVKLSCTASGFNIKDDYMHWVKQRPEQGLEWIGWIDPENGDT

EYASKFQGKATITADTSSNTAYLQLSSLTSEDTAVYYCTRSSVGYWGQGTTLTVSSGGGGS

GGGGSGGGGSDVVMTQTPLSLPVSLGDQASISCRSSQSLVHSNGNTYLHWYLQKPGQSPK

LLIYKVSNRFSGVPDRFSGSGSGTYFTLKISRVEAEDLGVYFCSQRTHVPYTFGGGTKLEIK

KLKASGGRHROPRGWEQLGGGGGSPTGAEFLGDGGDVSFSTRGTQNWTVERLWAHRQL

EERGYVFVGYHGTFLEAAQSIVFGGVRARSQDLDAIWRGFYIAGDPALAYGYAQDQEPDA

RGRIRNGALLRVYVPRSSLPGFYRTSLTLAAPEAAGEVERLIGHPLPLRLDAITGPEEEGGR

LETILGWPLAERTVVIPSAIPTDPRNVGGDLDPSSIPDKEQAISALPDYASQPGKPPREDLK

D4-AAA-D4-LR nucleotide sequence
(SEQ ID NO: 18)
ATGCAGGTGCAGCTGGTGGAGTCTGGGGGAGGCTTGGTGCAGCCCGGGGGGTCTCTGA

GACTCTCCTGTGTAGCCTCTGGATACAGCTACAGTATTGGTTACATGGCCTGGTTCCGC

CAGGCCCCAGGAAAGGAGCGCGCGTGGGTCGCGTCTCGATATACTGGTGACGGTGGC

```
GCAGTCTTTGACGACGCCGTGAAGGGCCGATTCACCACCTCCCAAGAGAGTGCCGGGA

ACACGTTCGATTTGCAAATGGACAGCCTGAAACCTGAGGACACTGCCATGTACTATTG

CGCAGCGAAAGGGCCCGGTTTCGGGCGGTGGGAGTACTGGGGCCGGGGGACCCAGGT

CACCGTCTCCTCAGCGGCGGCGCAGGTGCAGCTGGTGGAGTCTGGGGGAGGCTTGGTG

CAGCCCGGGGGGTCTCTGAGACTCTCCTGTGTAGCCTCTGGATACAGCTACAGTATTG

GTTACATGGCCTGGTTCCGCCAGGCCCCAGGAAAGGAGCGCGCGTGGGTCGCGTCTCG

ATATACTGGTGACGGTGGCGCAGTCTTTGACGACGCCGTGAAGGGCCGATTCACCACC

TCCCAAGAGAGTGCCGGGAACACGTTCGATTTGCAAATGGACAGCCTGAAACCTGAGG

ACACTGCCATGTACTATTGCGCAGCGAAAGGGCCCGGTTTCGGGCGGTGGGAGTACTG

GGGCCGGGGGACCCAGGTCACCGTCTCCTCAAAGCTTAAAGCAAGCGGCGGTCGCCAT

CGCCAGCCGCGCGGCTGGGAACAGCTGGGCGGTGGCGGTGGCAGCCCCACCGGTGCC

GAGTTCCTGGGCGACGGTGGCGATGTGTCCTTTAGCACCCGTGGTACCCAGAACTGGA

CGGTAGAGCGCCTGCTGCAGGCACATCGTCAGCTGGAAGAGCGTGGCTATGTATTCGT

TGGCTACCACGGCACTTTTCTGGAAGCAGCTCAGTCCATCGTGTTTGGTGGTGTCCGTG

CCCGTTCTCAAGACCTGGATGCGATTTGGCGTGGTTTCTACATTGCAGGCGATCCAGCG

CTGGCATACGGTTATGCGCAGGACCAGGAACCGGATGCTCGTGGTCGCATTCGTAATG

GTGCGCTGCTGCGCGTATATGTGCCGCGTTCCAGCCTGCCGGGCTTCTACCGCACTAGC

CTGACCCTGGCCGCGCCGGAGGCGGCGGGTGAAGTGGAACGTCTGATTGGTCATCCTC

TGCCTCTGCGCCTGGATGCCATCACCGGCCCAGAGGAGGAGGGCGGTCGTCTGGAAAC

CATTCTGGGCTGGCCGCTGGCTGAACGTACGGTCGTTATTCCGAGCGCGATTCCTACCG

ATCCTCGTAACGTTGGCGGCGATCTGGACCCATCTTCTATTCCAGATAAGGAGCAGGC

AATCTCCGCGCTGCCGGATTATGCAAGCCAACCGGGTAAACCACCTCGTGAAGATCTG

AAATAA
```

D4-AAA-D4-LR amino acid sequence
(SEQ ID NO: 19)
MQVQLVESGGGLVQPGGSLRLSCVASGYSYSIGYMAWFRQAPGKERAWVASRYTGDGG
AVFDDAVKGRFTTSQESAGNTFDLQMDSLKPEDTAMYYCAAKGPGFGRWEYWGRGTQV
TVSSAAAQVQLVESGGGLVQPGGSLRLSCVASGYSYSIGYMAWFRQAPGKERAWVASRY
TGDGGAVI-DDAVKGRFTTSQESAGNTFDLQMDSLKPEDTAMYYCAAKGPGFGRWEYWG
RGTQVTVSSKLKASGGRHRQPRGWEQLGGGGGSPTGAEFLGDGGDVSFSTRGTQNWTVE
RLLQAHRQLEERGYVFVGYHGTFLEAAQSIVFGGVRARSQDLDAIWRGFYIAGDPALAYG
YAQDQEPDARGRIRNGALLRVYVPRSSLPGFYRTSLTLAAPEAAGEVERLIGHPLPLRLDAI
TGPEEEGGRLETILGWPLAERTVVIPSAIPTDPRNVGGDLDPSSIPDKEQAISALPDYASQPG
KPPREDLK D4-GGS-D4-LR nucleotide sequence
(SEQ ID NO: 20)
```
ATGCAGGTGCAGCTGGTGGAGTCTGGGGGAGGCTTGGTGCAGCCCGGGGGGTCTCTGA

GACTCTCCTGTGTAGCCTCTGGATACAGCTACAGTATTGGTTACATGGCCTGGTTCCGC

CAGGCCCCAGGAAAGGAGCGCGCGTGGGTCGCGTCTCGATATACTGGTGACGGTGGC

GCAGTCTTTGACGACGCCGTGAAGGGCCGATTCACCACCTCCCAAGAGAGTGCCGGGA

ACACGTTCGATTTGCAAATGGACAGCCTGAAACCTGAGGACACTGCCATGTACTATTG

CGCAGCGAAAGGGCCCGGTTTCGGGCGGTGGGAGTACTGGGGCCGGGGGACCCAGGT

CACCGTCTCCTCAGGCGGCAGCCAGGTGCAGCTGGTGGAGTCTGGGGGAGGCTTGGTG
```

-continued

CAGCCCGGGGGGTCTCTGAGACTCTCCTGTGTAGCCTCTGGATACAGCTACAGTATTG

GTTACATGGCCTGGTTCCGCCAGGCCCCAGGAAAGGAGCGCGCGTGGGTCGCGTCTCG

ATATACTGGTGACGGTGGCGCAGTCTTTGACGACGCCGTGAAGGGCCGATTCACCACC

TCCCAAGAGAGTGCCGGGAACACGTTCGATTTGCAAATGGACAGCCTGAAACCTGAGG

ACACTGCCATGTACTATTGCGCAGCGAAAGGGCCCGGTTTCGGGCGGTGGGAGTACTG

GGGCCGGGGGACCCAGGTCACCGTCTCCTCAAAGCTTAAAGCAAGCGGCGGTCGCCAT

CGCCAGCCGCGCGGCTGGGAACAGCTGGGCGGTGGCGGTGGCAGCCCCACCGGTGCC

GAGTTCCTGGGCGACGGTGGCGATGTGTCCTTTAGCACCCGTGGTACCCAGAACTGGA

CGGTAGAGCGCCTGCTGCAGGCACATCGTCAGCTGGAAGAGCGTGGCTATGTATTCGT

TGGCTACCACGGCACTTTTCTGGAAGCAGCTCAGTCCATCGTGTTTGGTGGTGTCCGTG

CCCGTTCTCAAGACCTGGATGCGATTTGGCGTGGTTTCTACATTGCAGGCGATCCAGCG

CTGGCATACGGTTATGCGCAGGACCAGGAACCGGATGCTCGTGGTCGCATTCGTAATG

GTGCGCTGCTGCGCGTATATGTGCCGCGTTCCAGCCTGCCGGGCTTCTACCGCACTAGC

CTGACCCTGGCCGCGCCGGAGGCGGCGGGTGAAGTGGAACGTCTGATTGGTCATCCTC

TGCCTCTGCGCCTGGATGCCATCACCGGCCCAGAGGAGGAGGGCGGTCGTCTGGAAAC

CATTCTGGGCTGGCCGCTGGCTGAACGTACGGTCGTTATTCCGAGCGCGATTCCTACCG

ATCCTCGTAACGTTGGCGGCGATCTGGACCCATCTTCTATTCCAGATAAGGAGCAGGC

AATCTCCGCGCTGCCGGATTATGCAAGCCAACCGGGTAAACCACCTCGTGAAGATCTG

AAATAA

Figure 16A:
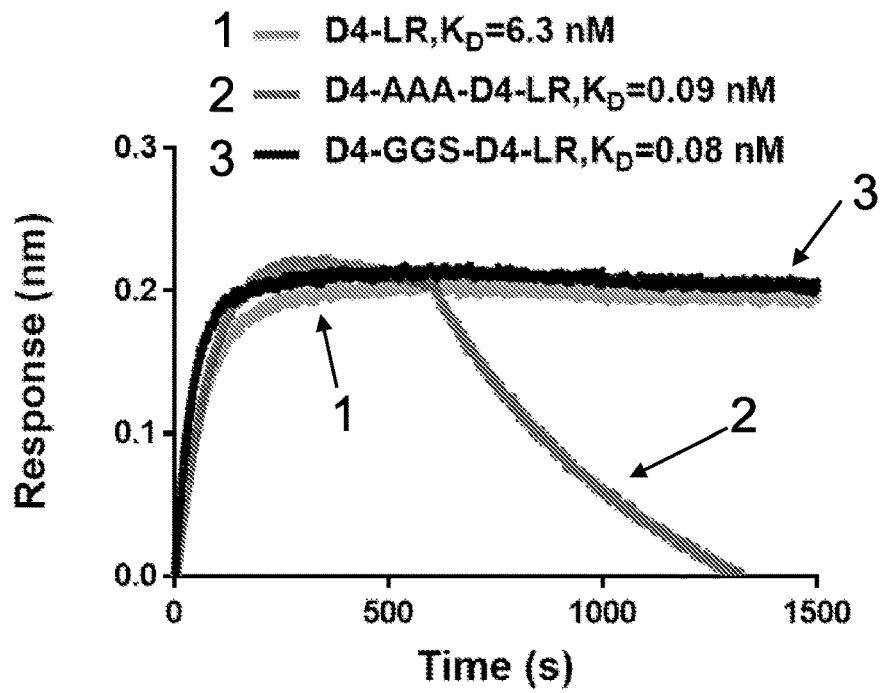
FIGS. 16A-16C: Re-engineered bivalent D4-D4-LR immunotoxins exhibit enhanced GPC1 binding activity. Shown are the results of Octet (FIG. 16A), ELISA (FIG. 16B) and FACS analysis (FIG. 16C).
Figure 16B:
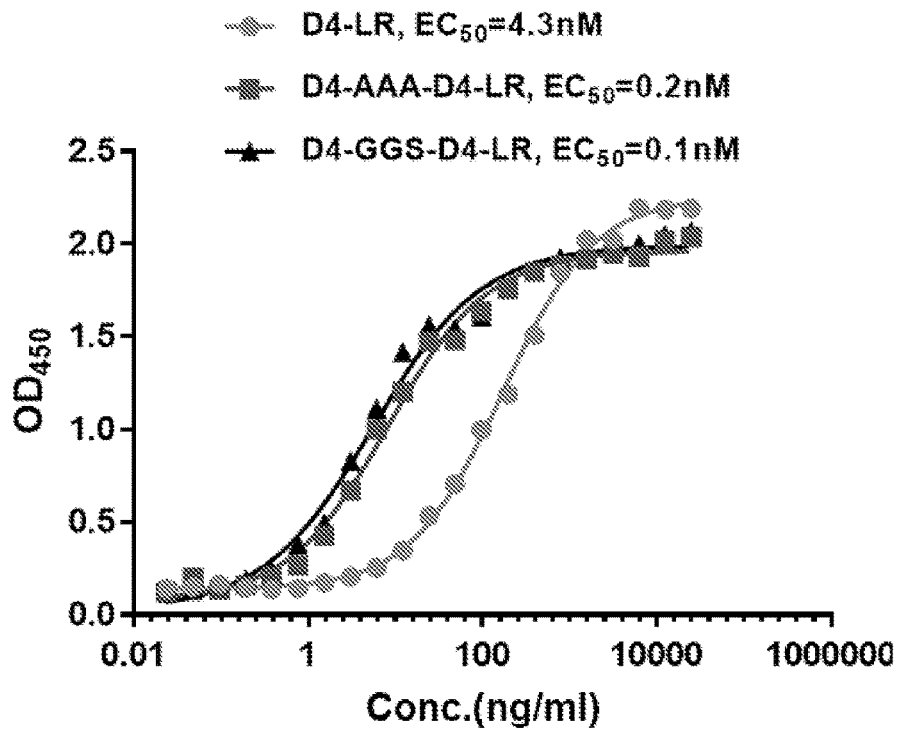
Figure 16C:
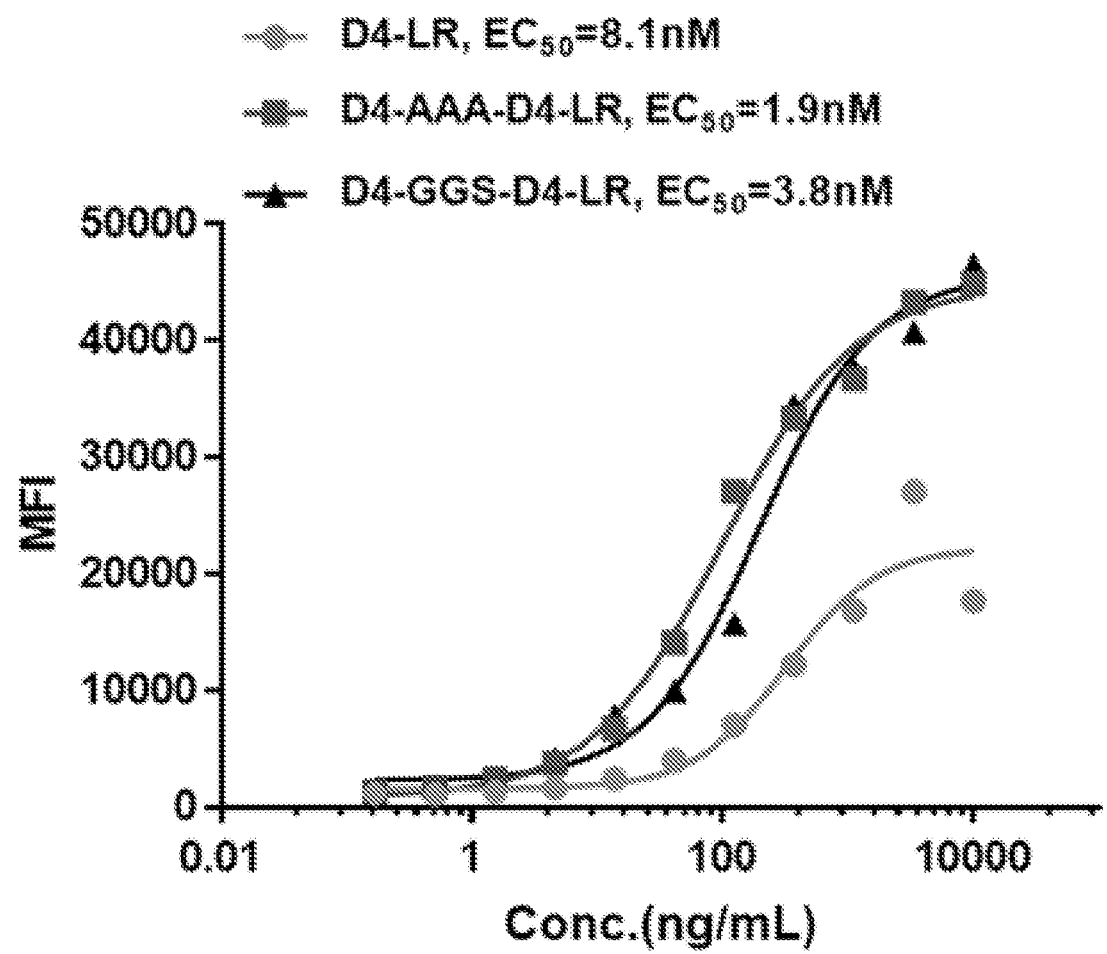

D4-GGS-D4-LR amino acid sequence (SEQ ID NO: 21)

MQVQLVESGGGLVQPGGSLRLSCVASGYSYSIGYMAWFRQAPGKERAWVASRYTGDGG

AVFDDAVKGRFTTSQESAGNTFDLQMDSLKPEDTAMYYCAAKGPGFGRWEYWGRGTQV

TVSSGGSQVQLVESGGGLVQPGGSLRLSCVASGYSYSIGYMAWFRQAPGKERAWVASRY

TGDGGAVFDDAVKGRFTTSQESAGNTFDLQMDSLKPEDTAMYYCAAKGPGFGRWEYWG

RGTQVTVSSKLKASGGRHRQPRGWEQLGGGGGSPTGAEFLGDGGDVSFSTRGTQNWTVE

RLLQAHRQLEERGYVFVGYHGTFLEAAQSIVFGGVRARSQDLDAIWRGFYIAGDPALAYG

YAQDQEPDARGRIRNGALLRVYVPRSSLPGFYRTSLTLAAPEAAGEVERLIGHPLPLRLDAI

TGPEEEGGRLETILGWPLAERTVVIPSAIPTDPRNVGGDLDPSSIPDKEQAISALPDYASQPG

KPPREDLK

Generation and Testing of GPC1-Targeted Immunotoxins

The HM2-LR immunotoxin is comprised of the HM2 VH domain linked to the HM2 VL domain via a $(G_4S)_3$ linker, and a truncated *Pseudomonas* exotoxin A (LR) conjugated to the VL domain. The D4-LR immunotoxin is comprised of the D4 VHH single-domain antibody conjugated to LR. Schematics of the two immunotoxins are shown in FIG. 12A. The purity and molecular weight of HM2-LR and D4-LR are shown in FIG. 12B.

Affinity of HM2-LR and D4-LR for GPC1 was tested using Octet analysis (FIGS. 13A-13B). The results demonstrated that both immunotoxins retained high affinity for GPC1, with a $K_D$ of 6.9 nM (HM2-LR) and 6.3 nM (D4-LR).

The immunotoxins were also tested for their ability to kill GPC1-positive cancer cells in vitro. Cytotoxicity assays were performed on GPC1-positive cell lines H8, 2B9 and T3M4, and GPC1-negative cell line A431 using WST-8 reagent after three days incubation. The D4-LR and HM2-LR immunotoxins efficiently killed GPC1 overexpressing H8 and 2B9 cell lines with IC50 values ranging from 14 to 31 ng/ml (FIGS. 14A and 14B). However, both immunotoxins exhibited inferior cell killing capacity on the native pancreatic cancer cell line T3M4 (FIG. 14C), which has a relatively lower GPC1 expression level. Neither immunotoxin was capable of killing GPC1-negative A431 cells (FIG. 14D), indicating specificity of the immunotoxins for GPC1-expressing cells.

To enhance killing capacity of the D4 immunotoxin, two bivalent D4 immunotoxins (D4-AAA-D4-LR and D4-GGS-D4-LR) were generated and tested. A schematic of the two D4-D4-LR immunotixins is shown in FIG. 15A. The purity and molecular weight of the immunotoxins are shown in FIG. 15B.

Binding affinity of the D4-D4-LR immunotoxins for GPC1 was evaluated using three different assays: Octet (FIG. 16A), ELISA (FIG. 16B) and FACS analysis (FIG. 16C). The results demonstrated that the immunotoxins exhibited improved binding to GPC1 compared to the D4-LR immunotoxin.

Figure 17A:
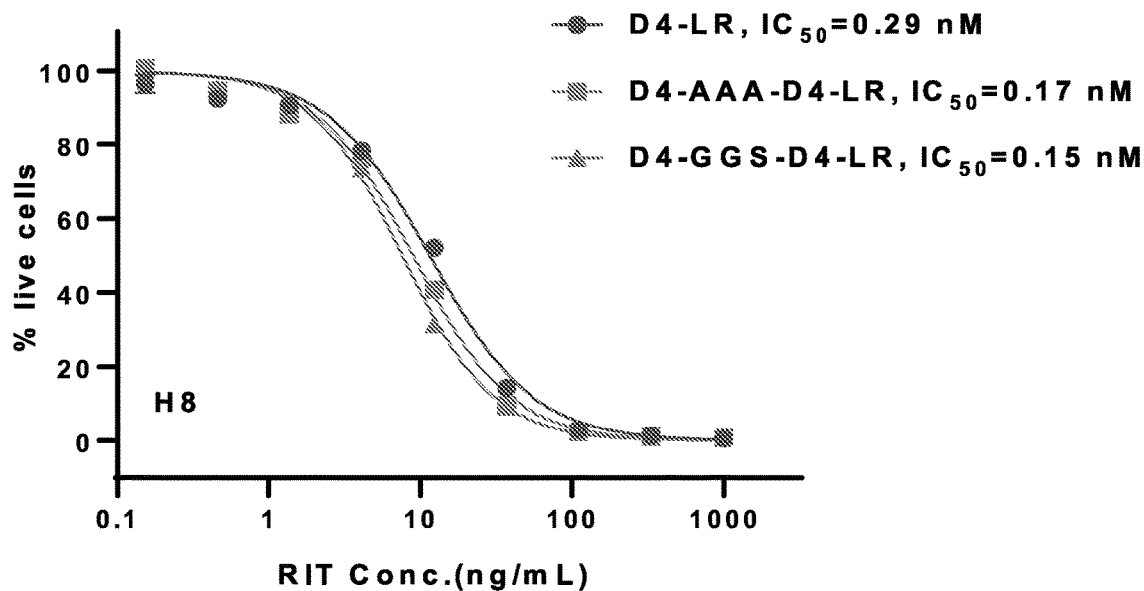
FIGS. 17A-17D: Cell killing curves of anti-GPC1 immunotoxins. Cytotoxicity assays were performed on GPC1-positive (H8, 2B9 and T3M4) and negative (A431) cell lines. Bivalent D4 immunotoxins showed similar efficacy on GPC1-overexpressing cell lines H8 (FIG. 17A) and 2B9 (FIG. 17B), but enhanced cytotoxicity on native pancreatic cancer cell line T3M4 (FIG. 17C), as compared with the D4-LR immunotoxin. All immunotoxins had little cell killing ability on GPC1 negative cell line A431 (FIG. 17D), indicating killing specificity of the immunotoxins.
Figure 17B:
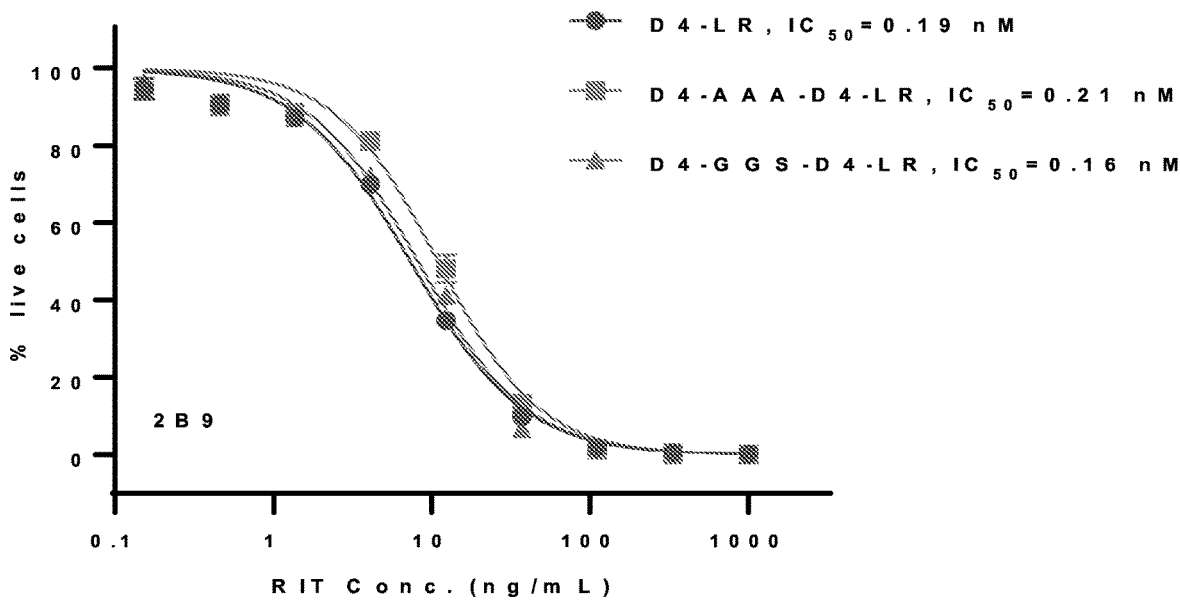
Figure 17C:
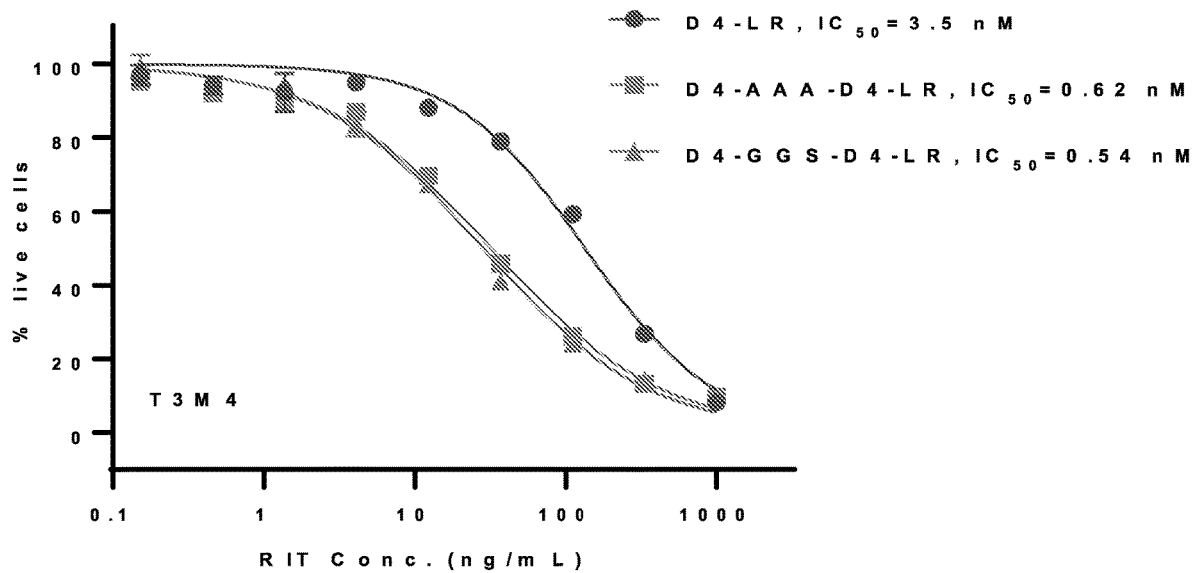
Figure 17D:
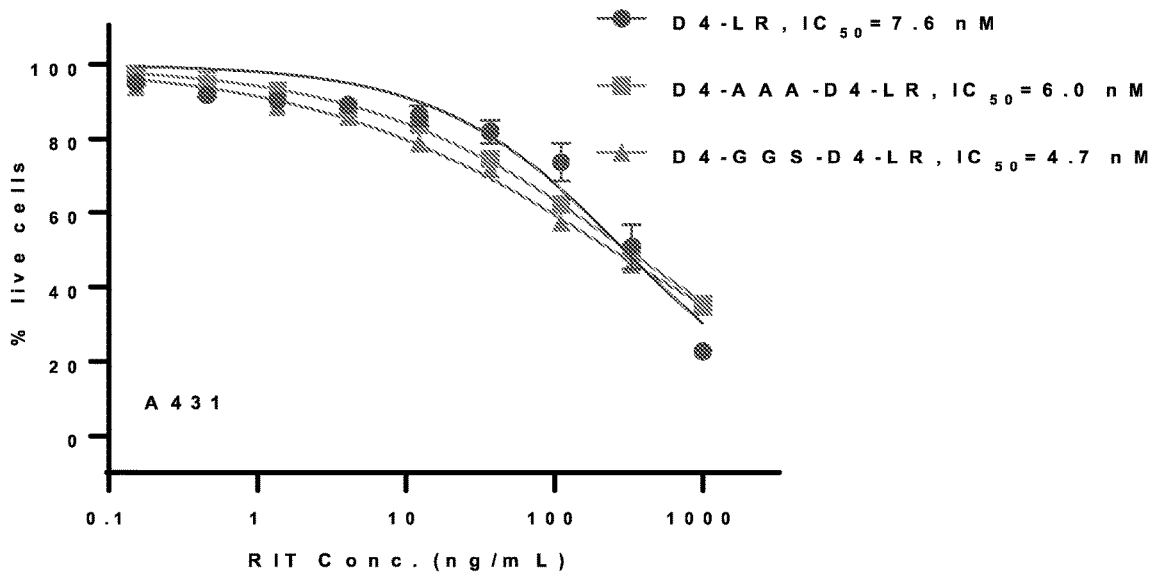

Cytotoxicity assays were performed to determine the ability of the D4-D4-LR immunotoxins to kill GPC1-expressing tumor cells. Assays were performed on GPC1-positive (H8, 2B9 and T3M4) and negative (A431) cell lines. Bivalent D4 immunotoxins showed similar efficacy on GPC1-overexpressing cell lines H8 (FIG. 17A) and 2B9 (FIG. 17B), and enhanced cytotoxicity (approximately 5-fold increased) on native pancreatic cancer cell line T3M4 (FIG. 17C), as compared with the D4-LR immunotoxin. All immunotoxins had little cell killing ability on GPC1 negative cell line A431 (FIG. 17D), indicating killing specificity of the immunotoxins.

Figure 18A:
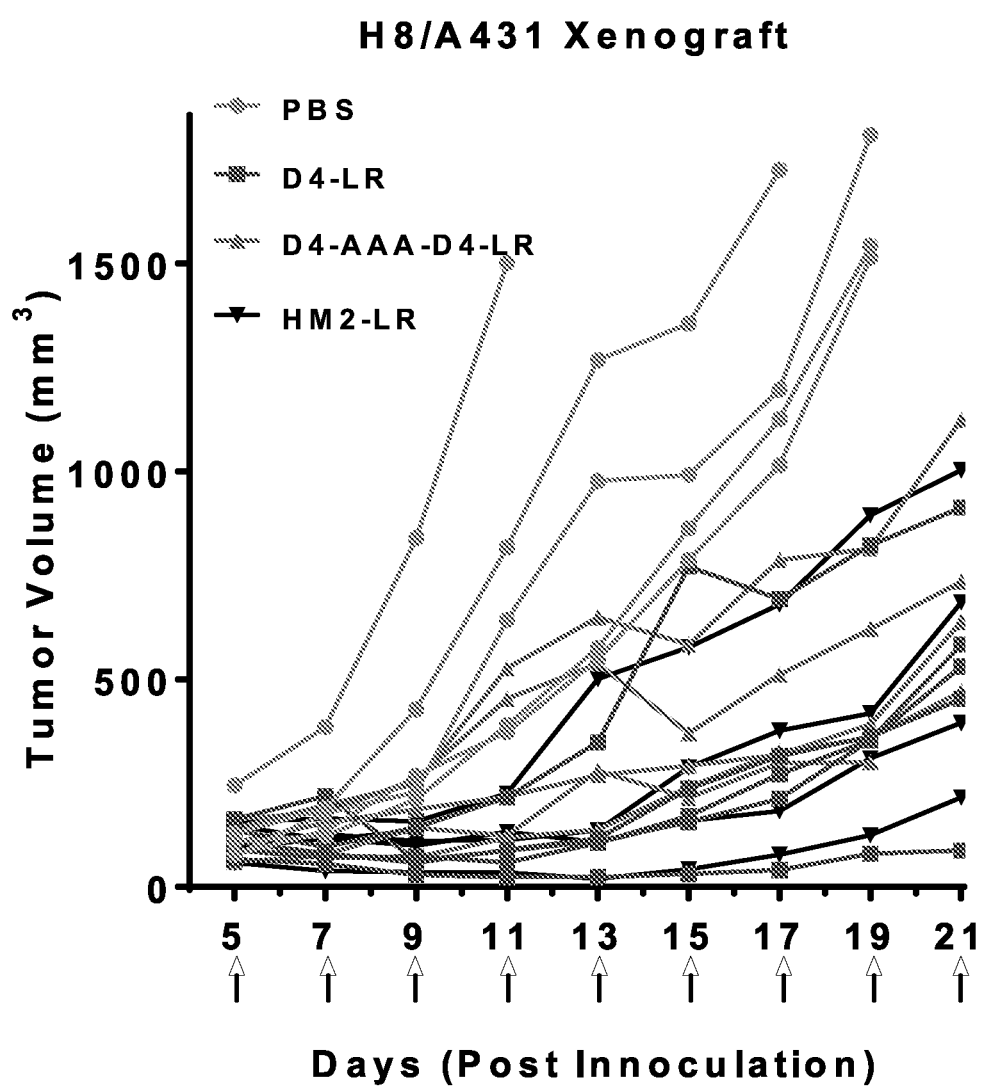
FIGS. 18A-18D: Anti-GPC1 immunotoxins significantly inhibit tumor growth in vivo. Five-week old female athymic nude mice were injected with 5×10$^6$ cells in the right dorsal flank. Mice were treated a total of nine times with D4-LR (5 mg/kg), D4-AAA-D4-LR (3 mg/kg) or HM2-LR (5 mg/kg)
Figure 18B:
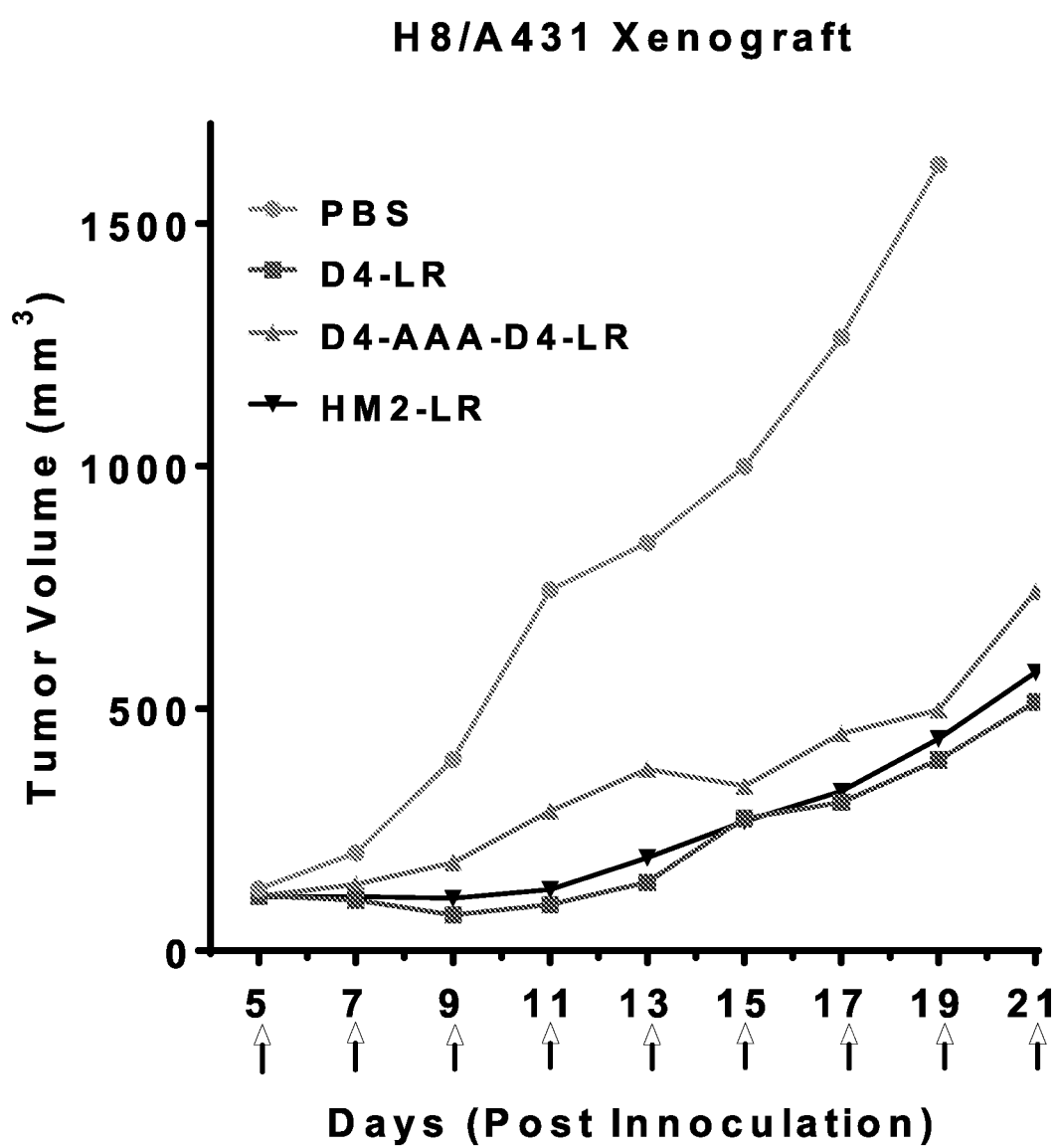
Figure 18C:
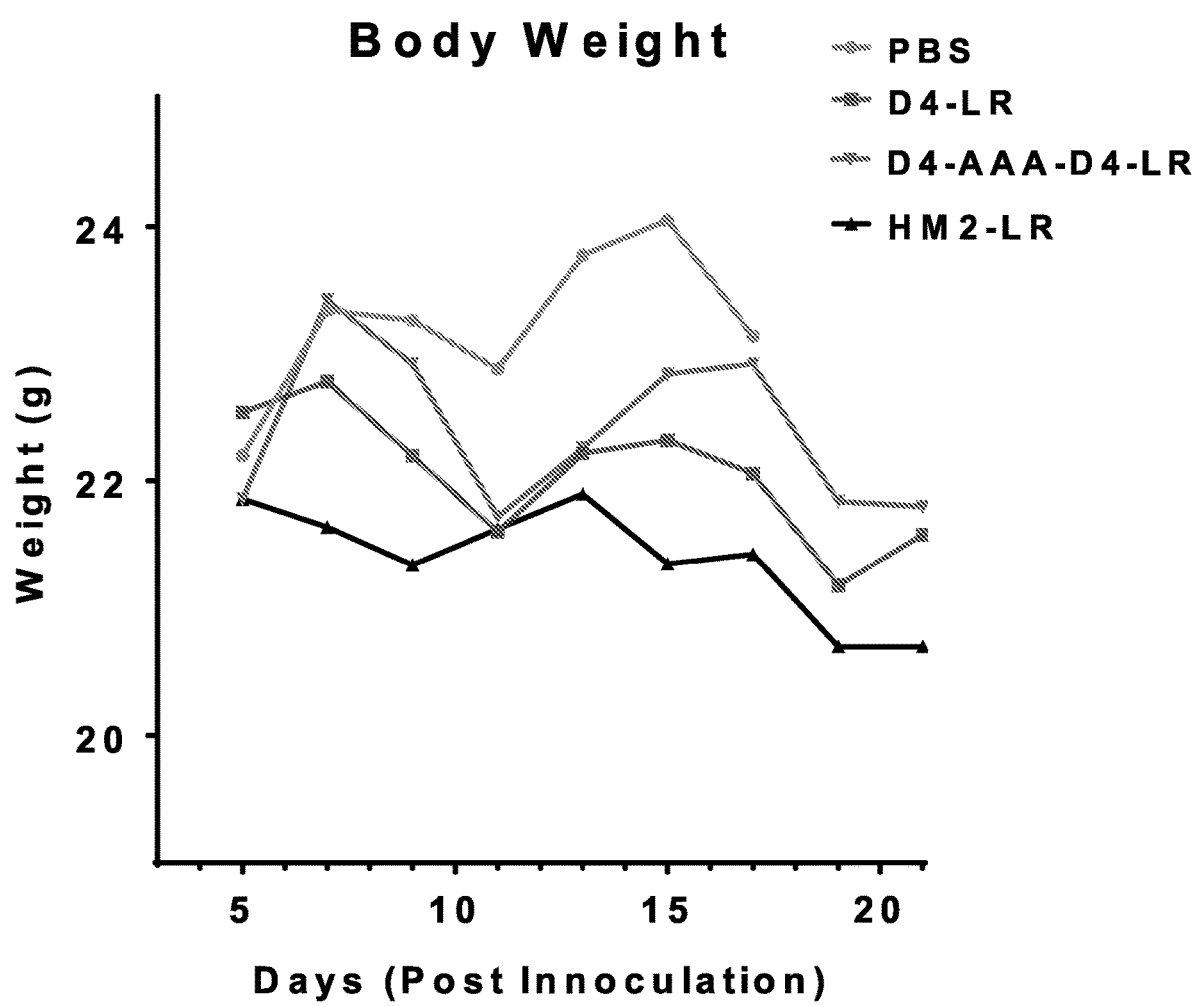
Figure 18D:
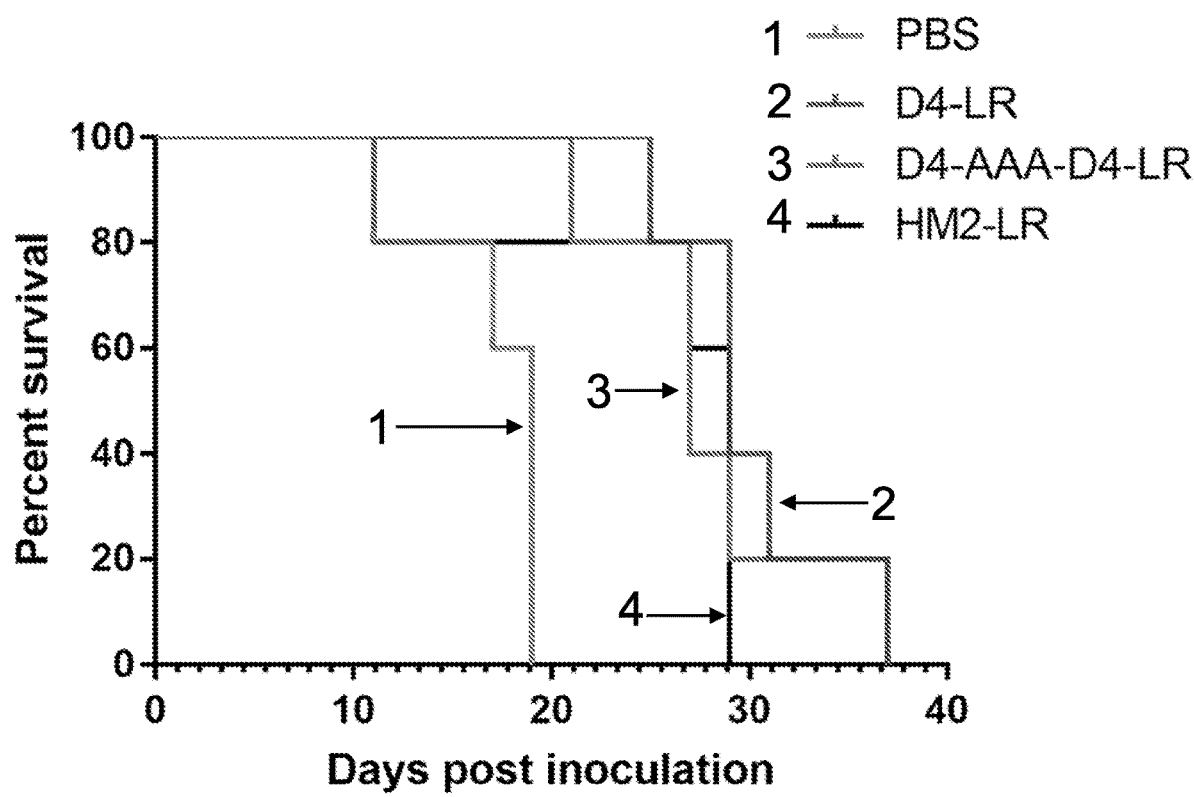

The effect of the D4-LR, D4-AAA-D4-LR and HM2-LR immunotoxins on tumor growth was tested in a mouse H8/A431 subcutaneous xenograft model. Five-week old female athymic nude mice were injected with $5 \times 10^6$ cells in the right dorsal flank. Mice were treated a total of nine times with D4-LR (5 mg/kg), D4-AAA-D4-LR (3 mg/kg) or HM2-LR (5 mg/kg) by tail vein injection on days 5, 7, 9, 11, 13, 15, 17, 19 and 21 post-inoculation. Each experimental group contained five mice. Tumor volume for each mouse and for the average of each experimental group are shown in FIG. 18A and FIG. 18B, respectively. Average body weight of mice during experimental treatment is shown in FIG. 18C. Survival curves of the immunotoxin-treated mice are shown in FIG. 18D. The results demonstrated that treatment with any of the three GPC1-specific immunotoxins significantly decreased tumor volume while having little effect on weight of the mice.

In view of the many possible embodiments to which the principles of the disclosure may be applied, it should be recognized that the illustrated embodiments are only examples and should not be taken as limiting the scope of the disclosure. Rather, the scope of the disclosure is defined by the following claims.

The invention claimed is:

1. A monoclonal antibody that specifically binds glypican 1 (GPC1), wherein:
    (i) the monoclonal antibody comprises a variable heavy (VH) domain and a variable light (VL) domain, wherein the VH domain comprises the complementarity determining region 1 (CDR1), CDR2 and CDR3 sequences of SEQ ID NO: 2 and the VL domain comprises the CDR1, CDR2 and CDR3 sequences of SEQ ID NO: 4; or
    (ii) the monoclonal antibody is a single-domain antibody comprising the CDR1, CDR2 and CDR3 sequences of SEQ ID NO: 6.

2. The monoclonal antibody of claim 1, wherein the CDR sequences are defined using the Kabat, IMGT, or Paratome numbering schemes.

3. The monoclonal antibody of claim 1, wherein the antibody comprises a VH domain and a VL domain, wherein the VH domain CDR1, CDR2 and CDR3 sequences respectively comprise:
    residues 31-35, 50-66 and 99-103 of SEQ ID NO: 2;
    residues 26-33, 51-58 and 97-103 of SEQ ID NO: 2;
    or residues 27-35, 47-61 and 97-103 of SEQ ID NO: 2.

4. The monoclonal antibody of claim 1, wherein the antibody comprises a VH domain and a VL domain, wherein the VL domain CDR1, CDR2 and CDR3 sequences respectively comprise:
    residues 24-39, 55-61 and 94-102 of SEQ ID NO: 4;
    residues 27-37, 55-57 and 94-101 of SEQ ID NO: 4;
    or residues 28-39, 51-61 and 94-102 of SEQ ID NO: 4.

5. The monoclonal antibody of claim 3, wherein:
    the amino acid sequence of the VH domain is at least 90% identical to SEQ ID NO: 2 and comprises the CDR1, CDR2 and CDR3 sequences of SEQ ID NO: 2; and
    the amino acid sequence of the VL domain is at least 90% identical to SEQ ID NO: 4 and comprises the CDR1, CDR2 and CDR3 sequences of SEQ ID NO: 4.

6. The monoclonal antibody of claim 3, wherein:
    the amino acid sequence of the VH domain comprises or consists of SEQ ID NO: 2; and
    the amino acid sequence of the VL domain comprises or consists of SEQ ID NO: 4.

7. The monoclonal antibody of claim 3, wherein the antibody comprises an antigen-binding fragment selected from an Fab fragment, an Fab' fragment, an F(ab)'$_2$ fragment, a single chain variable fragment (scFv) and a disulfide stabilized variable fragment (dsFv).

8. The monoclonal antibody of claim 3, wherein the monoclonal antibody is a mouse antibody, a humanized antibody or a chimeric antibody.

9. The monoclonal antibody of claim 1, wherein the antibody is a single domain antibody, wherein the CDR1, CDR2 and CDR3 sequences respectively comprise:
    residues 31-35, 50-66 and 99-109 of SEQ ID NO: 6;
    residues 26-33, 51-58 and 97-108 of SEQ ID NO: 6;
    or residues 27-33, 47-61 and 97-108 of SEQ ID NO: 6.

10. The monoclonal antibody of claim 9, wherein the amino acid sequence of the monoclonal antibody is at least 90% identical to SEQ ID NO: 6 and comprises the CDR1, CDR2 and CDR3 sequences of SEQ ID NO: 6.

11. The monoclonal antibody of claim 9, wherein the amino acid sequence of the monoclonal antibody comprises or consists of SEQ ID NO: 6.

12. The monoclonal antibody of claim 9, wherein the monoclonal antibody is a camel antibody a humanized antibody or a chimeric antibody.

13. A chimeric antigen receptor (CAR) comprising the monoclonal antibody of claim 1.

14. The CAR of claim 13, further comprising a hinge region, a transmembrane domain, a costimulatory signaling moiety, a signaling domain, or any combination thereof.

15. The CAR of claim 14, wherein;
the hinge region comprises a CD8α hinge region;
the transmembrane domain comprises a CD8α transmembrane domain;
the costimulatory signaling moiety comprises a 4-18B signaling moiety; and/or
the signaling domain comprises a CD3ζ signaling domain.

16. An isolated cell expressing the CAR of claim 13.

17. The isolated cell of claim 16, which is a cytotoxic T lymphocyte (CTL) or a natural killer (NK) cell.

18. An immunoconjugate comprising the monoclonal antibody of claim 1 and an effector molecule.

19. The immunoconjugate of claim 18, wherein the effector molecule is a toxin.

20. The immunoconjugate of claim 19, wherein the toxin is *Pseudomonas* exotoxin or a variant thereof.

21. The immunoconjugate of claim 20, wherein the *Pseudomonas* exotoxin variant is PE-LR.

22. The immunoconjugate of claim 18, wherein the amino acid sequence of the immunoconjugate comprises SEQ ID NO: 15, SEQ ID NO: 17, SEQ ID NO: 19 or SEQ ID NO: 21.

23. An antibody-drug conjugate (ADC) comprising a drug conjugated to the monoclonal antibody of claim 1.

24. A multi-specific antibody comprising the monoclonal antibody of claim 1 and at least one additional monoclonal antibody or antigen-binding fragment thereof.

25. An antibody-nanoparticle conjugate, comprising a nanoparticle conjugated to the monoclonal antibody of claim 1.

26. A fusion protein comprising the monoclonal antibody of claim 1 and a heterologous protein or peptide.

27. An isolated nucleic acid molecule encoding the monoclonal antibody of claim 1.

28. The isolated nucleic acid molecule of claim 27, comprising:
the nucleotide sequence of SEQ ID NO: 1, or a degenerate variant thereof;
the nucleotide sequence of SEQ ID NO: 3, or a degenerate variant thereof;
the nucleotide sequences of SEQ ID NO: 1 and SEQ ID NO: 3, or degenerate variants thereof;
the nucleotide sequence of SEQ ID NO: 5, or a degenerate variant thereof;
the nucleotide sequence of SEQ ID NO: 14, or a degenerate variant thereof;
the nucleotide sequence of SEQ ID NO: 16, or a degenerate variant thereof;
the nucleotide sequence of SEQ ID NO: 18, or a degenerate variant thereof; or
the nucleotide sequence of SEQ ID NO: 20, or a degenerate variant thereof.

29. A vector comprising the nucleic acid molecule of claim 27.

30. A nucleic acid molecule encoding a chimeric antigen receptor (CAR), comprising in the 5' to 3' direction:
a nucleic acid encoding a first granulocyte-macrophage colony stimulating factor receptor signal sequence (GMCSFRss);
a nucleic acid encoding the monoclonal antibody of claim 1;
a nucleic acid encoding an extracellular hinge region;
a nucleic acid encoding a transmembrane domain;
a nucleic acid encoding an intracellular co-stimulatory domain;
a nucleic acid encoding a intracellular signaling domain;
a nucleic acid encoding a self-cleaving 2A peptide;
a nucleic acid encoding a second GMCSFRss; and
a nucleic acid encoding a truncated human epidermal growth factor receptor (huEGFRt).

31. The nucleic acid molecule of claim 30, further comprising a human elongation factor 1α (EF1α) promoter sequence 5' of the nucleic acid encoding the first GMCSFRss.

32. A vector comprising the nucleic acid molecule of claim 30.

33. An isolated host cell comprising the nucleic acid molecule of claim 27.

34. A composition comprising a pharmaceutically acceptable carrier and the monoclonal antibody of claim 1.

35. A method of treating a GPC1-positive cancer in a subject, comprising administering to the subject the monoclonal antibody of claim 1.

36. A method of inhibiting tumor growth or metastasis of a GPC1-positive cancer in a subject, comprising administering to the subject the monoclonal antibody of claim 1.

37. The method of claim 35, wherein the GPC1-positive cancer is a solid tumor.

38. The method of claim 35, wherein the GPC1-positive cancer is a pancreatic cancer, colorectal cancer, liver cancer, glioma, lung cancer, head and neck cancer, thyroid cancer, endometrial cancer, breast cancer or ovarian cancer.

39. A method of detecting expression of GPC1 in a sample, comprising:
contacting the sample with the monoclonal antibody of claim 1; and
detecting binding of the antibody to the sample, thereby detecting expression of GPC1 in the sample.

40. A method of diagnosing a subject as having a GPC1-positive cancer, comprising:
contacting a sample obtained from the subject with the monoclonal antibody of claim 1; and
detecting binding of the antibody to the sample, thereby diagnosing the subject as having a GPC1-positive cancer.

* * * * *